US012571046B2

(12) United States Patent
Huentelman et al.

(10) Patent No.: US 12,571,046 B2
(45) Date of Patent: Mar. 10, 2026

(54) METHODS OF DETECTING AND TREATING MULTIPLE SYSTEM ATROPHY

(71) Applicant: THE TRANSLATIONAL GENOMICS RESEARCH INSTITUTE, Phoenix, AZ (US)

(72) Inventors: Matthew J. Huentelman, Phoenix, AZ (US); Ignazio Piras, Phoenix, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 985 days.

(21) Appl. No.: 17/334,683

(22) Filed: May 28, 2021

(65) Prior Publication Data

US 2021/0381055 A1      Dec. 9, 2021

Related U.S. Application Data

(60) Provisional application No. 63/034,526, filed on Jun. 4, 2020.

(51) Int. Cl.
| | |
|---|---|
| *C12Q 1/68* | (2018.01) |
| *A61K 31/192* | (2006.01) |
| *A61K 45/06* | (2006.01) |
| *A61P 25/28* | (2006.01) |
| *C07H 21/04* | (2006.01) |
| *C12Q 1/6883* | (2018.01) |

(52) U.S. Cl.
CPC .......... *C12Q 1/6883* (2013.01); *A61K 31/192* (2013.01); *A61K 45/06* (2013.01); *A61P 25/28* (2018.01); *C12Q 2600/158* (2013.01)

(58) Field of Classification Search
CPC ..... H04L 67/1001; H04L 43/08; H04L 67/02; H04L 69/22
See application file for complete search history.

(56) References Cited

U.S. PATENT DOCUMENTS

2022/0387393 A1* 12/2022 Hu ........................ A61K 31/192

OTHER PUBLICATIONS

Piras et al. (Acta Neuropathologica Communications, vol. 8, No. 76, Jun. 3, 2020). (Year: 2020).*
Zhou et al. (Journal of Clinical Investigation, vol. 130, No. 5, pp. 2220-2236, Mar. 23, 2020) (Year: 2020).*
Wong et al. (Exp Neurobiology, vol. 23, No. 4, pp. 337-344, Dec. 2014). (Year: 2014).*
Tan, C. K., et al. Expert Opinion on Therapeutic Targets 2017; 21(3): 333-348.
Piras, I. S., et al. Transcriptional profiling of multiple system atrophy cerebellar tissue highlights differences between parkinsonian and cerebellar sub-types of the disease. Acta Neuropathol Commun 2020; 8:76.

Aberg, K., et al. Human QKI, a potential regulator of mRNA expression of human oligodendrocyte-related genes involved in schizophrenia. Proc Natl Acad Sci USA 2006; 103(19):7482-7487.
Al-Chalabi, A., et al. Genetic variants of the alpha-synuclein gene SNCA are associated with multiple system atrophy. PLoS One 2009; 4(9):e7114.
Allen, M., et al. Human whole genome genotype and transcriptome data for Alzheimer's and other neurodegenerative diseases. Sci Data 2016; 3:160089.
Arai, Y., et al. α-Synuclein-positive structures in cases with sporadic Alzheimer's disease: Morphology and its relationship to tau aggregation. Brain Res 2001; 888(2):287-296.
Asi, Y.T., et al. Alpha-synuclein mRNA expression in oligodendrocytes in MSA. Glia 2014; 62(6):964-970.
Atwal, P.S., et al. Molybdenum cofactor deficiency. Mol Genet Metab 2016; 117(1):1-4.
Bennett, D. A., et al. Overview and findings from the religious orders study. Curr Alzheimer Res 2012; 9(6):628-645.
Berryer, M. H., et al. Decrease of SYNGAP1 in GABAergic cells impairs inhibitory synapse connectivity, synaptic inhibition and cognitive function. Nat Commun 2016; 7:13340.
Bettencourt, C., et al. White matter DNA methylation profiling reveals deregulation of HIP1, LMAN2, MOBP, and other loci in multiple system atrophy. Acta Neuropathol 2020; 139(1):135-156.
Bhidayasiri, R., et al. Multiple System Atrophy. Neurologist 2008; 14(4):224-237.
Braak, H., et al. Demonstration of Amyloid Deposits and Neurofibrillary Changes in Whole Brain Sections. Brain Pathol 1991; 1(3):213-216.
Breedveld, G., et al. Novel mutations in three families confirm a major role of COL4A1 in hereditary porencephaly. J Med Genet 2006; 43(6):490-495.
Cescon, M., et al. Lack of collagen VI promotes neurodegeneration by impairing autophagy and inducing apoptosis during aging. Aging (Albany NY) 2016; 8:1083-1101.
Chen, B. J, et al. Characterization of circular RNAs landscape in multiple system atrophy brain. J Neurochem 2016; 139(3):485-496.
Cheng, J. S., et al. Collagen VI protects neurons against Abeta toxicity. Nat Neurosci 2009; 12(2):119-121.

(Continued)

*Primary Examiner* — Jeanine A Goldberg
(74) *Attorney, Agent, or Firm* — FULLER IP LAW LLC; Rodney J. Fuller

(57) ABSTRACT

The present disclosure relates to a method for diagnosing and treating multiple-system atrophy (MSA) in a subject, the method comprising: determining in a subject-derived biological sample an expression level of a gene from the group consisting of: QKI, GGCX, MOCS1, NF1, LINC01572, PRRG3, HMBOX1, PLP1, PPP1CA, C8orf88, TGFB2, MASP1, TIAM1, SYNGAP1, ACTN1, EMP1, NFIL3, GPNMB, PGAM2, ST5, STON1, RFTN1, and MMP14; comparing the subject-derived expression level of the gene with a normal control expression level of the gene obtained from a non-neurodegenerative biological sample; diagnosing the subject as a having MSA by detecting a differential expression of the gene in the subject-derived biological sample as compared to the normal control expression level; and administering a peroxisome proliferator-activated receptor β (PPARβ) agonist or a retinoid X receptor (RXR) agonist to the subject diagnosed as having MSA.

13 Claims, 25 Drawing Sheets
(13 of 25 Drawing Sheet(s) Filed in Color)

(56) References Cited

OTHER PUBLICATIONS

Chong, J. R., et al. Increased transforming growth factor β2 in the neocortex of Alzheimer's disease and dementia with lewy bodies is correlated with disease severity and soluble Aβ 42 load. J Alzheimer's Dis 2017; 56(1):157-166.

Clement, J. P., et al. SYNGAP1 Links the Maturation Rate of Excitatory Synapses to the Duration of Critical-Period Synaptic Plasticity. J Neurosci 2013; 33(25):10447-10452.

Curry-Hyde, A., et al. Multiple System Atrophy: Many Lessons from the Transcriptome. Neuroscientist 2018; 24 (3):294-307.

Darbelli, L., et al. Transcriptome profiling of mouse brains with qkl-deficient oligodendrocytes reveals major alternative splicing defects including self-splicing. Sci Rep 2017; 7(1):7554.

Darbelli, L., et al. Quaking Regulates Neurofascin 155 expression for myelin and axoglial junction maintenance. J Neurosci 2016; 36(14):4106-4120.

Dash, S. K., et al. Abnormalities of white and grey matter in early multiple system atrophy: comparison of parkinsonian and cerebellar variants. Eur Radiol 2019; 29(2):716-724.

Djelloul, M., et al. Alpha-Synuclein Expression in the Oligodendrocyte Lineage: An in Vitro and in Vivo Study Using Rodent and Human Models. Stem Cell Reports 2015; 5(2):174-184.

Dobin, A., et al. STAR: Ultrafast universal RNA-seq aligner. Bioinformatics 2013; 29(1):15-21.

Dubois, B., et al. Revising the definition of Alzheimer's disease: A new lexicon. Lancet Neurol 2010; 9(11):1118-1127.

Duran, R. C. D., et al. Brain region-specific gene signatures revealed by distinct astrocyte subpopulations unveil links to glioma and neurodegenerative diseases. eNeuro 2019; 6(2):ENEURO.0288-18. 2019.

Ewels, P., et al. MultiQC: Summarize analysis results for multiple tools and samples in a single report. Bioinformatics 2016; 32(19):3047-3048.

Fanciulli, A., et al. Multiple-System Atrophy. N Engl J Med 2015; 372(3):249-263.

Goedert, M. Alpha-synuclein and neurodegenerative diseases. Nat Rev Neurosci 2001; 2(7):492-501.

Gómez Ravetti, M., et al. Uncovering molecular biomarkers that correlate cognitive decline with the changes of hippocampus' gene expression profiles in Alzheimer's disease. PLoS One 2010; 5(4):e10153.

Greene, C. S., et al. Understanding multicellular function and disease with human tissue-specific networks. Nat Genet 2015; 47(6):569-576.

Groh, J., et al. Pathogenic inflammation in the CNS of mice carrying human PLP1 mutations. Hum Mol Genet 2016; 25(21):4686-4702.

Hamilton, R. L. Lewy Bodies in Alzheimer's Disease: A Neuropathological Review of 145 Cases Using α-Synuclein Immunohistochemistry. Brain Pathol 2000; 10(3):278-284.

Hardy, J.A., et al. Alzheimer's disease: The amyloid cascade hypothesis. Science 1992; 256(5054):184-185.

Hebert, S. S., et al. Loss of microRNA cluster miR-29a/b-1 in sporadic Alzheimer's disease correlates with increased BACE1/-secretase expression. Proc Natl Acad Sci 2008; 105(17):6415-6420.

Jin, H., et al. Analyses of copy No. and mRNA expression level of the α-synuclein gene in multiple system atrophy. J Med Dent Sci 2008; 55(1):145-153.

Kiely, A.P., et al. Immunohistochemical and molecular investigations show alteration in the inflammatory profile of multiple system atrophy brain. J Neuropathol Exp Neurol 2018; 77(7):598-607.

Langerveld, A.J., et al. Gene expression changes in postmortem tissue from the rostral pons of multiple system atrophy patients. Mov Disord 2007; 22(6):766-777.

Langfelder, P., et al. WGCNA: an R package for weighted correlation network analysis. BMC Bioinformatics 2008; 9:559.

Li, Z., et al. Destabilization and mislocalization of myelin basic protein mRNAs in quaking dysmyelination lacking the QKI RNA-binding proteins. J Neurosci 2000; 20(13):4944-4953.

Liao, Y., et al. FeatureCounts: An efficient general purpose program for assigning sequence reads to genomic features. Bioinformatics 2014; 30(7):923-930.

Lin, C. H., et al. COQ2 gene variants associate with cerebellar subtype of multiple system atrophy in Chinese. Mov Disord 2015; 30(3):436-437.

Lippa, C. F., et al. Lewy bodies contain altered α-synuclein in brains of many familial Alzheimer's disease patients with mutations in presenilin and amyloid precursor protein genes. Am J Pathol 1998; 153(5):1365-1370.

Love, M. I., et al. Moderated estimation of fold change and dispersion for RNA-seq data with DESeq2. Genome Biol 2014; 15(12):550.

May, V. E. L., et al. α-Synuclein impairs oligodendrocyte progenitor maturation in multiple system atrophy. Neurobiol Aging 2014; 35(10):2357-2368.

Mills, J.D., et al. Transcriptome analysis of grey and white matter cortical tissue in multiple system atrophy. Neurogenetics 2015; 16(2):107-122.

Mills, J.D., et al. Strand-specific RNA-sequencing analysis of multiple system atrophy brain transcriptome. Neuroscience 2016; 322:234-250.

Mitsui, J., et al. Mutations in COQ2 in familial and sporadic multiple-system atrophy. N Engl J Med 2013; 369 (3):233-244.

Nirenberg, M. J., et al. Multiple system atrophy in a patient with the spinocerebellar ataxia 3 gene mutation. Mov Disord 2007; 22(2):251-254.

Ordway, G. A., et al. Gene expression analyses of neurons, astrocytes, and oligodendrocytes isolated by laser capture microdissection from human brain: Detrimental effects of laboratory humidity. J Neurosci Res 2009; 87 (11):2430-2438.

Ota, K., et al. Relocation of p25α/tubulin polymerization promoting protein from the nucleus to the perinuclear cytoplasm in the oligodendroglia of sporadic and COQ2 mutant multiple system atrophy. Acta Neuropathol Commun 2014; 2:136.

Paiva, I., et al. Alpha-synuclein deregulates the expression of COL4A2 and impairs ER-Golgi function. Neurobiol Dis 2018; 119:121-135.

Papp, M. I., et al. Glial cytoplasmic inclusions in the CNS of patients with multiple system atrophy (striatonigral degeneration, olivopontocerebellar atrophy and Shy-Drager syndrome). J Neurol Sci 1989; 94(1-3):79-100.

Piper, D. A., et al. Advancing stem cell models of alpha-synuclein gene regulation in neurodegenerative disease. Front Neurosci 2018; 12:199.

Piras, I.S., et al. ESHRD: deconvolution of brain homogenate RNA expression data to identify cell-type-specific alterations in Alzheimer's disease. Aging (Albany NY) 2020; 12(5):4124-4162.

Quinn, N., et al. Multiple system atrophy. Curr Opin Neurol 1995; 8(4):323-326.

Rannikmäe, K., et al. Common variation in COL4A1/COL4A2 is associated with sporadic cerebral small vessel disease. Neurology 2015; 84(9):918-926.

Ritchie, M.E., et al. limma powers differential expression analyses for RNA-sequencing and microarray studies. Nucleic Acids Res 2015; 43(7):e47.

Roncevic, D., et al. Cerebellar and parkinsonian phenotypes in multiple system atrophy: Similarities, differences and survival. J Neural Transm (Vienna) 2014; 121(5):507-512.

Sailer, A., et al. A genome-wide association study in multiple system atrophy. Neurology 2016; 87(15):1591-1598.

Scholz, S.W., et al. SNCA variants are associated with increased risk for multiple system atrophy. Ann Neurol 2009; 65(5):610-614.

Schroder, M. S., et al. survcomp: an R/Bioconductor package for performance assessment and comparison of survival models. Bioinformatics 2011; 27(22):3206-3208.

Shannon, P., et al. Cytoscape: A software Environment for integrated models of biomolecular interaction networks. Genome Res 2003; 13(11):2498-2504.

Shingu, T., et al. Qki deficiency maintains stemness of glioma stem cells in suboptimal environment by downregulating endolysosomal degradation. Nat Genet 2017; 49(1):75-86.

(56)              References Cited

OTHER PUBLICATIONS

Sidman, R. L., et al. Mutant Mice (Quaking And Jimpy) With Deficient Myelination In The Central Nervous System. Science 1964; 144(3616):309-311.

Da Silva, F. L., et al. Vitamins K interact with N-terminus α-synuclein and modulate the protein fibrillization in vitro. Exploring the interaction between quinones and α-synuclein. Neurochem Int 2013; 62(1):103-112.

Song, Y. J. C., et al. p25α relocalizes in oligodendroglia from myelin to cytoplasmic inclusions in multiple system atrophy. Am J Pathol 2007; 171(4):1291-1303.

Stefanova, N., et al. Multiple system atrophy: an update. Lancet Neurol 2009; 8(12):1172-1178.

Stefanova, N., et al. Multiple system atrophy: Emerging targets for interventional therapies. Neuropathol Appl Neurobiol 2016; 42(1):20-32.

Suleiman, L., et al. Protein S: A multifunctional anticoagulant vitamin K-dependent protein at the crossroads of coagulation, inflammation, angiogenesis, and cancer. Crit Rev Oncol Hematol 2013; 88(3):637-654.

Tamai, S., et al. Neuroprotective role of the basic leucine zipper transcription factor NFIL3 in models of amyotrophic lateral sclerosis. J Biol Chem 2014; 289(3):1629-1638.

Twohig, D., et al. α-synuclein in the pathophysiology of Alzheimer's disease. Mol Neurodegener 2019; 14:23.

Um, K., et al. Dynamic Control of Excitatory Synapse Development by a Rac1 GEF/GAP Regulatory Complex. Dev Cell 2014; 29(6):701-715.

Vanacore, N. Epidemiological evidence on multiple system atrophy. J Neural Transm (Vienna) 2005; 112(12):1605-1612.

Wakabayashi, K., et al. α-synuclein immunoreactivity in glial cytoplasmic inclusions in multiple system atrophy. Neurosci Lett 1998; 249(2-3):180-182.

Wang, J., et al. WEB-based GEne SeT Analysis Toolkit (WebGestalt): update 2013. Nucleic Acids Res 2013; 41 (Web Server Issue):W77-W83.

Wang, M., et al. The Mount Sinai cohort of large-scale genomic, transcriptomic and proteomic data in Alzheimer's disease. Sci data 2018; 5:180185.

Zaykin, D. V. Optimally weighted Z-test is a powerful method for combining probabilities in meta-analysis. J Evol Biol 2011; 24(8):1836-1841.

Zhang, Y., et al. An RNA-Sequencing Transcriptome and Splicing Database of Glia, Neurons, and Vascular Cells of the Cerebral Cortex. J Neurosci 2014; 34(36):11929-11947.

Zhao, Q. Z., et al. Association of the COQ2 V393A variant with risk of multiple system atrophy in East Asians: a case-control study and meta-analysis of the literature. Neurol Sci 2016; 37(3):423-430.

Zhong, H., et al. The phosphorylation status of nuclear NF-κB determines its association with CBP/p300 or HDAC-1. Mol Cell 2002; 9(3):625-636.

Zhong, S. C., et al. Expression and subcellular location of alpha-synuclein during mouse-embryonic development. Cell Mol Neurobiol 2010; 30(3):469-482.

Zhou, X., et al. Mature myelin maintenance requires Qki to coactivate PPARβ-RXRα-mediated lipid metabolism. J Clin Invest 2020; 130(5):2220-2236.

Benjamini, Y., et al. Controlling the false discovery rate: a practical and powerful approach to multiple testing. J R Stat Soc B 1995; 57(1):289-300.

Durinck, S., et al. BioMart and Bioconductor: A powerful link between biological databases and microarray data analysis. Bioinformatics 2005; 21(16):3439-3440.

Langfelder, P., et al. Eigengene networks for studying the relationships between co-expression modules. BMC Syst Biol 2007; 1:54.

Langfelder, P., et al. Is my network module preserved and reproducible? PLoS Comput Biol 2011; 7.

Lee, H. K., et al. Coexpression analysis of human genes across many microarray data sets. Genome Res 2004; 14 (6):1085-1094.

Okonechnikov, K., et al. Qualimap 2: Advanced multi-sample quality control for high-throughput sequencing data. Bioinformatics 2015; 32(2):292-294.

Zhang, B., et al. A general framework for weighted gene co-expression network analysis. Stat Appl Genet Mol Biol 2005; 4:Article 17.

Wong, J. H., et al. Exploring myelin dysfunction in multiple system atrophy. Exp Neurobiol 2014; 23(4):337-344.

Schottlaender, L. V., et al. Mutant COQ2 in Multiple-System Atrophy. N Engl J Med 2014; 271(1):81.

* cited by examiner

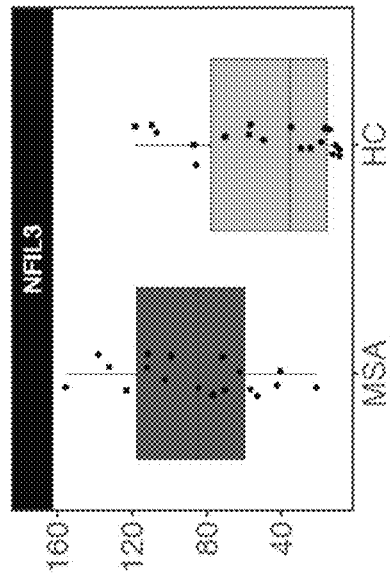
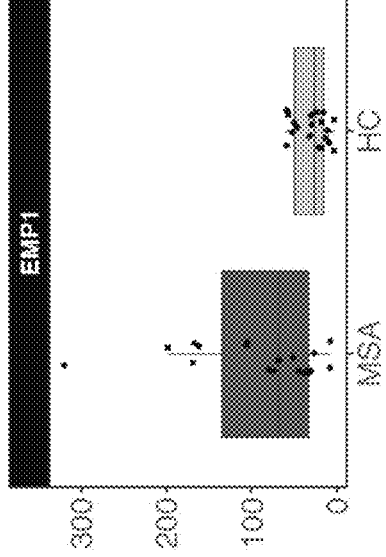
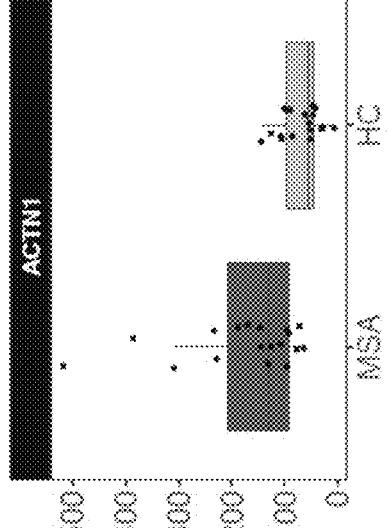
FIG. 2A

Table 2. Top genes for the different MSA subtypes after p-value combination. Downregulated genes are reported in grey.

| Group | Genes Info | | Differential Expression Cohort 1 | | | | Differential Expression Cohort 2 | | | | Combined p-values | | Averaged log2 FC |
|---|---|---|---|---|---|---|---|---|---|---|---|---|---|
| | Symbol | Ensembl ID | Base Mean | log2 (FC) | p | adj p | Base Mean | log2 (FC) | p | adj p | p | adj p | |
| MSA | ACTN1 | ENSG00000072110 | 120.266 | 1.309 | 2.3E-06 | 1.4E-02 | 152.163 | 1.055 | 1.4E-04 | 2.0E-01 | 1.2E-07 | 1.4E-03 | 1.182 |
| | EMP1 | ENSG00000134531 | 59.778 | 1.636 | 7.4E-06 | 1.6E-02 | 240.880 | 1.254 | 7.3E-04 | 4.9E-01 | 5.8E-07 | 3.5E-03 | 1.445 |
| | NFIL3 | ENSG00000165030 | 68.525 | 1.019 | 1.1E-04 | 4.6E-02 | 21.457 | 1.567 | 5.1E-04 | 4.1E-01 | 2.4E-06 | 9.8E-03 | 1.293 |
| | PI15 | ENSG00000137558 | 13.120 | 1.086 | 2.3E-02 | 3.7E-01 | 11.510 | 2.273 | 9.8E-06 | 5.1E-02 | 6.0E-06 | 1.8E-02 | 1.679 |
| | TUBB6 | ENSG00000176014 | 31.136 | 1.426 | 4.5E-06 | 1.5E-02 | 0.696 | 1.885 | 8.8E-02 | 1.0E+00 | 9.0E-06 | 2.2E-02 | 1.656 |
| | VIM | ENSG00000026025 | 297.903 | 0.701 | 7.8E-03 | 2.5E-01 | 1841.955 | 1.240 | 7.0E-05 | 1.5E-01 | 1.1E-05 | 2.2E-02 | 0.971 |
| | COL4A1 | ENSG00000187498 | 94.979 | 1.424 | 1.6E-04 | 5.6E-02 | 71.659 | 1.008 | 4.3E-03 | 7.6E-01 | 1.3E-05 | 2.2E-02 | 1.216 |
| | NFKBIA | ENSG00000100906 | 280.164 | 0.672 | 9.7E-05 | 4.1E-02 | 8.006 | 0.932 | 8.9E-03 | 8.8E-01 | 1.5E-05 | 2.2E-02 | 0.802 |
| | MAT2A | ENSG00000168906 | 766.718 | 0.641 | 6.1E-03 | 2.4E-01 | 1065.143 | 0.902 | 1.6E-04 | 2.0E-01 | 1.6E-05 | 2.2E-02 | 0.771 |
| | AEBP1 | ENSG00000106624 | 238.300 | 1.638 | 2.1E-06 | 1.4E-02 | 14.682 | 0.328 | 4.5E-01 | 1.0E+00 | 1.9E-05 | 2.2E-02 | 0.983 |
| MSA-P | GPNMB | ENSG00000136235 | 87.507 | 1.798 | 1.5E-03 | 3.0E-01 | 34.116 | 1.773 | 2.2E-05 | 7.7E-02 | 1.7E-06 | 2.0E-02 | 1.785 |
| | PGAM2 | ENSG00000164708 | 64.618 | 1.906 | 4.7E-04 | 3.6E-02 | 230.022 | 3.193 | 3.5E-08 | 4.8E-05 | 2.7E-08 | 5.6E-05 | 2.549 |
| | ST5 | ENSG00000166444 | 140.163 | 1.216 | 6.0E-07 | 7.8E-04 | 79.401 | 1.146 | 8.8E-05 | 6.7E-03 | 4.8E-08 | 5.6E-05 | 1.181 |
| | STON1 | ENSG00000243244 | 59.570 | 1.560 | 1.1E-03 | 5.7E-02 | 433.908 | 2.177 | 1.0E-08 | 2.7E-05 | 2.3E-08 | 5.6E-05 | 1.868 |
| | RFTN1 | ENSG00000131378 | 53.043 | 2.423 | 7.5E-07 | 8.6E-04 | 66.900 | 1.345 | 6.2E-05 | 6.0E-03 | 4.5E-08 | 5.6E-05 | 1.884 |
| MSA-C | ACTN1 | ENSG00000072110 | 101.733 | 1.939 | 2.9E-05 | 9.3E-03 | 141.214 | 1.905 | 5.7E-06 | 1.5E-03 | 8.6E-08 | 7.0E-05 | 1.922 |
| | MMP14 | ENSG00000157227 | 68.018 | 1.740 | 1.5E-04 | 2.0E-02 | 270.406 | 2.128 | 1.2E-06 | 5.8E-04 | 9.0E-08 | 7.0E-05 | 1.934 |
| | ITGB4 | ENSG00000132470 | 425.361 | 1.491 | 1.2E-04 | 1.8E-02 | 109.863 | 1.650 | 6.0E-06 | 1.5E-03 | 1.8E-07 | 1.2E-04 | 1.570 |
| | MAPK4 | ENSG00000141639 | 274.832 | 1.561 | 3.6E-09 | 6.0E-05 | 53.534 | 0.402 | 3.6E-01 | 6.5E-01 | 2.9E-07 | 1.7E-04 | 0.981 |
| | OMG | ENSG00000126861 | 431.926 | -1.384 | 2.3E-03 | 8.0E-02 | 56.937 | -2.185 | 2.5E-06 | 9.7E-04 | 6.0E-07 | 2.3E-04 | -1.785 |
| | FAM107A | ENSG00000168309 | 2370.587 | 0.848 | 9.9E-03 | 1.6E-01 | 2751.910 | 1.754 | 3.5E-07 | 2.7E-04 | 4.6E-07 | 2.3E-04 | 1.301 |

FIG. 9

Table 3. Top results of the functional module discovery analysis using the DEGs identified in MSA-C

| CLUSTER (Genes) | TERM_NAME | GO_ID | Q_VALUE | GENE_COUNT | TERM_GENES |
|---|---|---|---|---|---|
| M1 (152) | amyloid-beta formation | GO:0034205 | 5.3E-05 | 6 | ROCK2,DYRK1A,CLU,PSEN1,EFNA1,APP |
| | amyloid precursor protein catabolic process | GO:0042987 | 1.0E-04 | 6 | ROCK2,DYRK1A,CLU,PSEN1,EFNA1,APP |
| | amyloid-beta metabolic process | GO:0050435 | 1.0E-04 | 6 | ROCK2,DYRK1A,CLU,PSEN1,EFNA1,APP |
| | amyloid precursor protein metabolic process | GO:0042982 | 2.8E-04 | 6 | ROCK2,DYRK1A,CLU,PSEN1,EFNA1,APP |
| | amyloid fibril formation | GO:1990000 | 1.0E-03 | 4 | CLU,GSN,APP,PSEN1 |
| M2 (85) | NADH dehydrogenase complex assembly | GO:0010257 | 8.2E-03 | 4 | NDUFA1,NDUFS5,NDUFB3,NDUFB5 |
| | mitochondrial respiratory chain complex I assembly | GO:0032981 | 8.2E-03 | 4 | NDUFA1,NDUFS5,NDUFB3,NDUFB5 |
| | mitochondrion organization | GO:0007005 | 1.6E-02 | 7 | SLC25A5,NDUFB3,NDUFB5,PARP1,PSMD10,N DUFS5,NDUFA1 |
| | mitochondrial respiratory chain complex assembly | GO:0033108 | 1.8E-02 | 4 | NDUFA1,NDUFS5,NDUFB3,NDUFB5 |
| | negative regulation of centriole replication | GO:0046600 | 2.0E-02 | 2 | RBM14,CHMP2A |
| M3 (117) | regulation of cellular protein localization | GO:1903827 | 1.1E-02 | 9 | EZR,IWS1,RDX,GPSM2,NUMB,PICALM,RTN4, BAG3,UHMK1 |
| | regulation of organelle assembly | GO:1902115 | 1.4E-02 | 6 | STAG1,EZR,CCP110,GPSM2,RDX,CHMP5 |
| | sulfur compound biosynthetic process | GO:0044272 | 1.7E-02 | 4 | MTRR,GCLC,MAT2A,PAPSS1 |
| | membrane docking | GO:0022406 | 1.8E-02 | 3 | PDZD8,EZR,ATG14 |
| | regulation of protein export from nucleus | GO:0046825 | 2.3E-02 | 3 | BAG3,IWS1,UHMK1 |
| M4 (12) | negative regulation of multi-organism process | GO:0043901 | 1.3E-02 | 3 | IFITM3,TIMP1,ANXA2 |
| | regulation of multi-organism process | GO:0043900 | 2.8E-02 | 3 | IFITM3,TIMP1,ANXA2 |
| | negative regulation of protein catabolic process | GO:0042177 | 3.3E-02 | 2 | TIMP1,ANXA2 |
| | skeletal system development | GO:0001501 | 3.9E-02 | 2 | CD44,ANXA2 |
| | negative regulation of endopeptidase activity | GO:0010951 | 4.0E-02 | 2 | CD44,TIMP1 |
| M5 (63) | integrin-mediated signaling pathway | GO:0007229 | 2.2E-02 | 3 | FLNA,LAMA5,ZYX |
| | positive regulation of cell development | GO:0010720 | 2.8E-02 | 4 | NSMF,FLNA,ARHGEF2,PLXNB2 |

FIG. 10A

| | GO ID | p-value | count | genes |
|---|---|---|---|---|
| actin cytoskeleton organization | GO:0030036 | 4.0E-02 | 5 | FSCN1,RHOG,FLNA,ZYX,ARHGEF2 |
| actin filament organization | GO:0007015 | 4.1E-02 | 4 | FSCN1,FLNA,ARHGEF2,ZYX |
| supramolecular fiber organization | GO:0097435 | 4.1E-02 | 5 | FSCN1,FLNA,ZYX,B4GALT7,ARHGEF2 |
| M6 (10) calcium ion transport | GO:0006816 | 4.0E-02 | 2 | CDH23,PRKG1 |
| divalent metal ion transport | GO:0070838 | 4.1E-02 | 2 | CDH23,PRKG1 |
| divalent inorganic cation transport | GO:0072511 | 4.1E-02 | 2 | CDH23,PRKG1 |
| M7 (164) synapse organization | GO:0050808 | 4.4E-02 | 3 | CNTN2,NLGN3,SLITRK1 |
| M8 (24) renal system development | GO:0072001 | 4.7E-02 | 2 | COL4A1,ITGB4 |
| urogenital system development | GO:0001655 | 4.9E-02 | 2 | COL4A1,ITGB4 |

FIG. 10B

Table 4. Top genes differentially expressed in oligodendrocytes in MSA vs HC

| Genes | Ensembl Gene Id | Biotype | Base Mean | log2 FC | Stat | p | adj p |
|---|---|---|---|---|---|---|---|
| GGCX | ENSG00000115486 | Protein Coding | 803.4 | 1.691 | 7.072 | 1.5E-12 | 1.1E-08 |
| MOCS1 | ENSG00000124615 | Protein Coding | 405.2 | -1.759 | -6.433 | 1.2E-10 | 4.4E-07 |
| NF1 | ENSG00000196712 | Protein Coding | 775.5 | -1.532 | -6.089 | 1.1E-09 | 2.4E-06 |
| LINC01572 | ENSG00000261008 | lincRNA | 207.2 | -2.010 | -6.063 | 1.3E-09 | 2.4E-06 |
| PRRG3 | ENSG00000130032 | Protein Coding | 269.3 | 1.808 | 5.731 | 1.0E-08 | 1.4E-05 |
| HMBOX1 | ENSG00000147421 | Protein Coding | 124.9 | 2.247 | 5.588 | 2.3E-08 | 2.7E-05 |
| PLP1 | ENSG00000123560 | Protein Coding | 383.7 | -1.744 | -5.494 | 3.9E-08 | 3.5E-05 |
| - | ENSG00000249906 | antisense | 29.0 | 4.224 | 5.495 | 3.9E-08 | 3.5E-05 |
| PPP1CA | ENSG00000172531 | Protein Coding | 458.2 | -1.617 | -5.359 | 8.4E-08 | 6.6E-05 |
| C8orf88 | ENSG00000253250 | Protein Coding | 46.1 | -2.657 | -5.313 | 1.1E-07 | 7.6E-05 |

FIG. 11

Table S1. Differentially expressed genes detected in the cohort 1 and cothort 2 in MSA.

| Cohorts | Genes | Ensembl Gene Id | entreziD | Biotype | Base Mean | log2 Fold Change | SE | Stat | p | p-adj |
|---|---|---|---|---|---|---|---|---|---|---|
| | ACTN1 | ENSG00000072110 | 87 | Protein Coding | 120.3 | 1.309 | 0.277 | 4.727 | 2.3E-06 | 1.4E-02 |
| | AEBP1 | ENSG00000106624 | 165 | Protein Coding | 238.3 | 1.638 | 0.346 | 4.740 | 2.1E-06 | 1.4E-02 |
| | SNED1 | ENSG00000162804 | 25992 | Protein Coding | 130.5 | 1.013 | 0.217 | 4.672 | 3.0E-06 | 1.4E-02 |
| | MAP3K14 | ENSG00000006062 | 9020 | Protein Coding | 50.3 | 0.847 | 0.186 | 4.549 | 5.4E-06 | 1.5E-02 |
| | TUBB6 | ENSG00000176014 | 84617 | Protein Coding | 31.1 | 1.426 | 0.311 | 4.585 | 4.5E-06 | 1.5E-02 |
| | BAG3 | ENSG00000151929 | 9531 | Protein Coding | 515.6 | 1.832 | 0.411 | 4.456 | 8.3E-06 | 1.6E-02 |
| | EMP1 | ENSG00000134531 | 2012 | Protein Coding | 59.8 | 1.636 | 0.365 | 4.483 | 7.4E-06 | 1.6E-02 |
| | PLEKHH3 | ENSG00000068137 | 79990 | Protein Coding | 40.5 | 1.038 | 0.236 | 4.396 | 1.1E-05 | 1.9E-02 |
| | APOL4 | ENSG00000100336 | 80832 | Protein Coding | 10.3 | 3.015 | 0.700 | 4.306 | 1.7E-05 | 2.1E-02 |
| | SEPT9 | ENSG00000184640 | 10801 | Protein Coding | 410.0 | 0.617 | 0.143 | 4.325 | 1.5E-05 | 2.1E-02 |
| | SPRED3 | ENSG00000188766 | 399473 | Protein Coding | 39.0 | 1.212 | 0.282 | 4.298 | 1.7E-05 | 2.1E-02 |
| | SNCG | ENSG00000173267 | 6623 | Protein Coding | 166.7 | -1.115 | 0.264 | -4.228 | 2.4E-05 | 2.7E-02 |
| | IGFBP4 | ENSG00000141753 | 3487 | Protein Coding | 54.4 | 1.328 | 0.316 | 4.202 | 2.6E-05 | 2.8E-02 |
| | CD163 | ENSG00000177575 | 9332 | Protein Coding | 108.6 | 1.831 | 0.439 | 4.169 | 3.1E-05 | 3.0E-02 |
| | COL4A2 | ENSG00000134871 | 1284 | Protein Coding | 85.0 | 1.314 | 0.321 | 4.096 | 4.2E-05 | 3.4E-02 |
| | MAFB | ENSG00000204103 | 9935 | Protein Coding | 52.6 | 1.577 | 0.385 | 4.095 | 4.2E-05 | 3.4E-02 |
| | SNHG3 | ENSG00000242125 | - | Processed Transcript | 37.0 | 1.160 | 0.282 | 4.118 | 3.8E-05 | 3.4E-02 |
| | KIF5C | ENSG00000276734 | 3800 | Protein Coding | 3512.9 | -0.398 | 0.099 | -4.041 | 5.3E-05 | 3.5E-02 |
| Cohort 1 | NOTCH2 | ENSG00000134250 | 4853 | Protein Coding | 394.4 | 0.735 | 0.182 | 4.029 | 5.6E-05 | 3.5E-02 |
| | PCDHGA5 | ENSG00000253485 | 56110 | Protein Coding | 53.7 | 0.906 | 0.225 | 4.033 | 5.5E-05 | 3.5E-02 |
| | RNU11 | ENSG00000274978 | - | snRNA | 552.3 | 1.850 | 0.459 | 4.028 | 5.6E-05 | 3.5E-02 |
| | SSH1 | ENSG00000084112 | 54434 | Protein Coding | 221.4 | 0.641 | 0.159 | 4.035 | 5.5E-05 | 3.5E-02 |
| | BCL6 | ENSG00000113916 | 604 | Protein Coding | 621.3 | 0.838 | 0.209 | 4.001 | 6.3E-05 | 3.6E-02 |
| | MFHAS1 | ENSG00000147324 | 9258 | Protein Coding | 90.8 | 0.901 | 0.226 | 3.989 | 6.6E-05 | 3.6E-02 |
| | SERPINA5 | ENSG00000188488 | 5104 | Protein Coding | 19.4 | 1.870 | 0.470 | 3.981 | 6.9E-05 | 3.6E-02 |
| | SERPINH1 | ENSG00000149257 | 871 | Protein Coding | 237.6 | 2.392 | 0.601 | 3.983 | 6.8E-05 | 3.6E-02 |
| | FLJ45513 | - | - | - | 12.2 | 1.701 | 0.430 | 3.952 | 7.7E-05 | 3.9E-02 |
| | ST5 | ENSG00000166444 | 6764 | Protein Coding | 157.3 | 0.759 | 0.193 | 3.933 | 8.4E-05 | 4.1E-02 |
| | FOSL2 | ENSG00000075426 | 2355 | Protein Coding | 194.4 | 1.471 | 0.376 | 3.909 | 9.3E-05 | 4.1E-02 |
| | NFKBIA | ENSG00000100906 | 4792 | Protein Coding | 280.2 | 0.672 | 0.173 | 3.898 | 9.7E-05 | 4.1E-02 |
| | THBD | ENSG00000178726 | 7056 | Protein Coding | 27.7 | 2.502 | 0.639 | 3.916 | 9.0E-05 | 4.1E-02 |
| | TLE3 | ENSG00000140332 | 7090 | Protein Coding | 135.6 | 0.911 | 0.233 | 3.905 | 9.4E-05 | 4.1E-02 |

FIG. 12A

| Cohorts | Genes | Ensembl Gene Id | entrezID | Biotype | Base Mean | log2 Fold Change | SE | Stat | p | p-adj |
|---|---|---|---|---|---|---|---|---|---|---|
| | NFIL3 | ENSG00000165030 | 4783 | Protein Coding | 68.5 | 1.019 | 0.264 | 3.866 | 1.1E-04 | 4.6E-02 |
| | SHC1 | ENSG00000160691 | 6464 | Protein Coding | 84.4 | 0.861 | 0.223 | 3.859 | 1.1E-04 | 4.6E-02 |
| | ZYX | ENSG00000285443 | 7791 | Protein Coding | 153.5 | 0.608 | 0.158 | 3.852 | 1.2E-04 | 4.6E-02 |
| | IRF2BPL | ENSG00000119669 | 64207 | Protein Coding | 184.4 | 0.678 | 0.177 | 3.841 | 1.2E-04 | 4.7E-02 |
| | ATP2B4 | ENSG00000058668 | 493 | Protein Coding | 527.4 | 0.504 | 0.132 | 3.822 | 1.3E-04 | 4.9E-02 |
| Cohort 2 | MLPH | ENSG00000115648 | 79083 | Protein Coding | 10.3 | 2.575 | 0.442 | 5.828 | 5.6E-09 | 1.2E-04 |
| | DAO | ENSG00000110887 | 1610 | Protein Coding | 9.6 | -1.895 | 0.380 | -4.989 | 6.1E-07 | 6.3E-03 |

FIG. 12B

Table S2. Differentially expressed genes detected in the cohort 1 and cohort 2 in MSA-P

MSA P

| Cohorts | Genes | Ensembl Gene Id | entrezID | Biotype | Base Mean |
|---|---|---|---|---|---|
| Cohort 1 | SEPT9 | ENSG00000184640 | 10801 | Protein Coding | 349.6 |
| | AEBP1 | ENSG00000106624 | 165 | Protein Coding | 191.2 |
| | TTR | ENSG00000118271 | 7276 | Protein Coding | 129.9 |
| | TGFB2 | ENSG00000092969 | 7042 | Protein Coding | 79.0 |
| Cohort 2 | DAO | ENSG00000110887 | 1610 | Protein Coding | 10.2 |
| | MLPH | ENSG00000115648 | 79083 | Protein Coding | 9.7 |

| Cohorts | log2 Fold Change | SE | Stat | p | p-adj |
|---|---|---|---|---|---|
| Cohort 1 | 0.844 | 0.179 | 4.725 | 2.3E-06 | 3.0E-02 |
| | 2.373 | 0.536 | 4.428 | 9.5E-06 | 4.1E-02 |
| | 6.675 | 1.485 | 4.494 | 7.0E-06 | 4.1E-02 |
| | 2.042 | 0.471 | 4.331 | 1.5E-05 | 4.8E-02 |
| Cohort 2 | -2.121 | 0.385 | -5.508 | 3.6E-08 | 4.1E-04 |
| | 2.663 | 0.485 | 5.493 | 4.0E-08 | 4.1E-04 |

FIG. 13

Differential Expression Cohort 1

| Genes Info | | | Base Mean | Log2 (FC) | Log2 (FC) SE | Stat | p | adj p | P_1Tail |
|---|---|---|---|---|---|---|---|---|---|
| Symbol | Ensembl ID | Entrez ID | | | | | | | |
| TMEM101 | ENSG00000091947 | 84336 | 23.811 | -4.505 | 1.151 | -3.913 | 9.1E-05 | 1.5E-01 | 1.0E+00 |
| WWC1 | ENSG00000113645 | 23286 | 223.663 | 0.862 | 0.655 | 1.317 | 1.9E-01 | 1.0E+00 | 9.4E-02 |
| MMP14 | ENSG00000157227 | 4323 | 117.673 | 0.832 | 0.495 | 1.682 | 9.3E-02 | 1.0E+00 | 4.6E-02 |
| OLFML3 | ENSG00000116774 | 56944 | 32.502 | -4.543 | 1.359 | -3.343 | 8.3E-04 | 3.1E-01 | 1.0E+00 |
| CHMP5 | ENSG00000086065 | 51510 | 85.445 | -0.121 | 0.428 | -0.282 | 7.8E-01 | 1.0E+00 | 6.1E-01 |
| FOXP2 | ENSG00000128573 | 93986 | 16.983 | -3.821 | 1.127 | -3.389 | 7.0E-04 | 3.1E-01 | 1.0E+00 |
| HSPB8 | ENSG00000152137 | 26353 | 362.687 | 0.903 | 0.631 | 1.430 | 1.5E-01 | 1.0E+00 | 7.6E-02 |
| PTOV1 | ENSG00000104960 | 53635 | 181.234 | -0.385 | 0.371 | -1.039 | 3.0E-01 | 1.0E+00 | 8.5E-01 |
| PGAM2 | ENSG00000164708 | 5224 | 114.069 | 0.871 | 0.787 | 1.107 | 2.7E-01 | 1.0E+00 | 1.3E-01 |
| HSPA1A | ENSG00000234475 | 3303 | 1549.779 | -0.804 | 0.726 | -1.106 | 2.7E-01 | 1.0E+00 | 8.7E-01 |

Differential Expression Cohort 2

| Genes Info | | | Base Mean | Log2 (FC) | Log2 (FC) SE | Stat | p | adj p | P_1Tail |
|---|---|---|---|---|---|---|---|---|---|
| Symbol | Ensembl ID | Entrez ID | | | | | | | |
| TMEM101 | ENSG00000091947 | 84336 | 27.490 | -0.654 | 0.280 | -2.337 | 1.9E-02 | 3.5E-01 | 9.9E-01 |
| WWC1 | ENSG00000113645 | 23286 | 35.781 | 1.357 | 0.310 | 4.372 | 1.2E-05 | 5.9E-02 | 6.2E-06 |
| MMP14 | ENSG00000157227 | 4323 | 382.463 | 1.406 | 0.372 | 3.784 | 1.5E-04 | 9.4E-02 | 7.7E-05 |
| OLFML3 | ENSG00000116774 | 56944 | 33.004 | -1.309 | 0.617 | -2.123 | 3.4E-02 | 4.1E-01 | 9.8E-01 |
| CHMP5 | ENSG00000086065 | 51510 | 130.493 | -0.796 | 0.188 | -4.224 | 2.4E-05 | 5.9E-02 | 1.0E+00 |
| FOXP2 | ENSG00000128573 | 93986 | 31.597 | -0.736 | 0.376 | -1.956 | 5.0E-02 | 4.6E-01 | 9.7E-01 |
| HSPB8 | ENSG00000152137 | 26353 | 2129.858 | 1.099 | 0.309 | 3.560 | 3.7E-04 | 1.0E-01 | 1.9E-04 |
| PTOV1 | ENSG00000104960 | 53635 | 68.174 | -0.981 | 0.262 | -3.745 | 1.8E-04 | 9.4E-02 | 1.0E+00 |
| PGAM2 | ENSG00000164708 | 5224 | 332.522 | 2.013 | 0.548 | 3.676 | 2.4E-04 | 9.4E-02 | 1.2E-04 |
| HSPA1A | ENSG00000234475 | 3303 | 28.309 | -2.184 | 0.607 | -3.598 | 3.2E-04 | 9.4E-02 | 1.0E+00 |

Combined P values

| Genes Info | | | P_Combined_1Tail | P_Combined | Adj P Combined | Averaged log2 FC |
|---|---|---|---|---|---|---|
| Symbol | Ensembl ID | Entrez ID | | | | |
| TMEM101 | ENSG00000091947 | 84336 | 1.0E+00 | 2.5E-05 | 8.4E-02 | -4.505 |
| WWC1 | ENSG00000113645 | 23286 | 1.6E-05 | 3.2E-05 | 8.4E-02 | 0.862 |
| MMP14 | ENSG00000157227 | 4323 | 6.0E-05 | 1.2E-04 | 2.1E-01 | 0.832 |
| OLFML3 | ENSG00000116774 | 56944 | 1.0E+00 | 2.0E-04 | 2.1E-01 | -4.543 |
| CHMP5 | ENSG00000086065 | 51510 | 1.0E+00 | 2.1E-04 | 2.1E-01 | -0.121 |
| FOXP2 | ENSG00000128573 | 93986 | 1.0E+00 | 2.4E-04 | 2.1E-01 | -3.821 |
| HSPB8 | ENSG00000152137 | 26353 | 1.8E-04 | 3.6E-04 | 2.4E-01 | 0.903 |
| PTOV1 | ENSG00000104960 | 53635 | 1.0E+00 | 3.7E-04 | 2.4E-01 | -0.385 |
| PGAM2 | ENSG00000164708 | 5224 | 2.1E-04 | 4.2E-04 | 2.4E-01 | 0.871 |
| HSPA1A | ENSG00000234475 | 3303 | 1.0E+00 | 5.3E-04 | 2.5E-01 | -0.804 |

FIG. 14

| Darbelli et al. (2017) (QKI Deficient vs QKI Proficient) | | | | | Present Study (Blue module) | | | |
|---|---|---|---|---|---|---|---|---|
| Entrez ID | MGI symbol | log2 FC | p | adj p | Genes | log2 FC | p | adj p |
| 4118 | Mal | -4.557 | 0.00E+00 | 0.00E+00 | MAL | -0.787 | 1.60E-01 | 5.10E-01 |
| 7368 | Ugt8a | -3.869 | 0.00E+00 | 0.00E+00 | UGT8 | -1.111 | 5.10E-02 | 3.20E-01 |
| 51228 | Gltp | -2.372 | 6.06E-304 | 3.41E-300 | GLTP | -0.905 | 6.50E-02 | 3.60E-01 |
| 22933 | Sirt2 | -1.885 | 5.34E-256 | 1.80E-252 | SIRT2 | -0.726 | 7.60E-02 | 3.80E-01 |
| 1267 | Cnp | -2.640 | 1.25E-243 | 3.52E-240 | CNP | -1.049 | 3.80E-02 | 2.90E-01 |
| 8537 | Bcas1 | -2.263 | 1.55E-202 | 2.91E-199 | BCAS1 | -1.520 | 6.30E-03 | 1.30E-01 |
| 133121 | Enpp6 | -2.675 | 2.12E-175 | 3.26E-172 | ENPP6 | -1.008 | 8.70E-02 | 4.00E-01 |
| 5365 | Plxnb3 | -2.876 | 1.63E-160 | 2.30E-157 | PLXNB3 | -0.580 | 1.70E-01 | 5.30E-01 |
| 79152 | Fa2h | -3.444 | 2.56E-121 | 2.88E-118 | FA2H | -0.850 | 1.60E-01 | 5.10E-01 |
| 5354 | Plp1 | -4.144 | 1.21E-105 | 1.07E-102 | PLP1 | -1.064 | 6.30E-02 | 3.50E-01 |
| 23446 | Slc44a1 | -1.934 | 5.68E-95 | 4.00E-92 | SLC44A1 | -0.834 | 5.10E-02 | 3.30E-01 |
| 29956 | Cers2 | -1.301 | 2.23E-84 | 1.45E-81 | CERS2 | -0.529 | 2.00E-01 | 5.60E-01 |
| 57471 | Ermn | -2.897 | 1.04E-70 | 5.17E-68 | ERMN | -1.356 | 1.70E-02 | 2.00E-01 |
| 4155 | Mbp | -3.603 | 3.06E-68 | 1.44E-65 | MBP | -1.378 | 3.90E-02 | 2.90E-01 |
| 64834 | Elovl1 | -1.524 | 3.72E-68 | 1.70E-65 | ELOVL1 | -1.233 | 1.40E-02 | 1.80E-01 |
| 2760 | Gm2a | -1.238 | 7.56E-68 | 3.36E-65 | GM2A | -0.440 | 2.20E-01 | 5.80E-01 |
| 6285 | S100b | -1.895 | 3.56E-63 | 1.31E-60 | S100B | -0.698 | 9.60E-02 | 4.20E-01 |
| 6319 | Scd2 | -1.054 | 6.12E-62 | 2.15E-59 | SCD | -0.864 | 7.70E-02 | 3.80E-01 |
| 285800 | Prr18 | -1.477 | 8.96E-59 | 2.80E-56 | PRR18 | -1.019 | 8.20E-02 | 3.90E-01 |
| 7018 | Trf | -1.765 | 1.53E-55 | 4.69E-53 | TF | -1.026 | 5.70E-02 | 3.40E-01 |
| 57165 | Gjc2 | -2.753 | 2.75E-55 | 8.14E-53 | GJC2 | -0.996 | 8.70E-02 | 4.00E-01 |
| 9514 | Gal3st1 | -1.738 | 3.40E-51 | 8.85E-49 | GAL3ST1 | -1.073 | 9.20E-02 | 4.10E-01 |
| 57475 | Plekhh1 | -1.497 | 7.71E-49 | 1.92E-46 | PLEKHH1 | -1.165 | 1.90E-01 | 2.20E-01 |
| 2065 | Erbb3 | -2.769 | 7.73E-48 | 1.81E-45 | ERBB3 | -1.273 | 1.90E-01 | 2.10E-01 |
| 10507 | Sema4d | -0.963 | 2.81E-45 | 6.08E-43 | SEMA4D | -0.970 | 6.00E-02 | 3.50E-01 |
| 2934 | Gsn | -1.901 | 3.01E-44 | 6.36E-42 | GSN | -0.603 | 1.40E-01 | 4.80E-01 |
| 118738 | Zfp488 | -1.420 | 6.80E-44 | 1.40E-41 | ZNF488 | -1.118 | 4.00E-02 | 2.90E-01 |
| 83700 | Jam3 | -1.026 | 7.34E-42 | 1.48E-39 | JAM3 | -1.034 | 2.80E-02 | 2.50E-01 |
| 2861 | Gpr37 | -1.140 | 1.40E-39 | 2.63E-37 | GPR37 | -1.316 | 2.50E-02 | 2.40E-01 |
| 3996 | Llgl1 | -0.953 | 4.56E-37 | 7.94E-35 | LLGL1 | -0.819 | 6.80E-02 | 3.60E-01 |
| 3916 | Lamp1 | -0.630 | 4.93E-34 | 7.71E-32 | LAMP1 | -0.476 | 1.60E-01 | 5.00E-01 |
| 60481 | Elovl5 | -0.753 | 3.04E-33 | 4.47E-31 | ELOVL5 | -0.343 | 2.90E-01 | 6.40E-01 |
| 57556 | Sema6a | -0.776 | 8.93E-33 | 1.27E-30 | SEMA6A | -0.688 | 4.70E-02 | 3.10E-01 |
| 745 | Myrf | -1.687 | 1.20E-32 | 1.66E-30 | MYRF | -1.064 | 6.00E-02 | 3.50E-01 |
| 9507 | Adamts4 | -1.690 | 9.94E-32 | 1.33E-29 | ADAMTS4 | -0.821 | 1.20E-01 | 4.40E-01 |
| 4336 | Mobp | -3.675 | 9.48E-30 | 1.20E-27 | MOBP | -1.699 | 4.40E-03 | 1.10E-01 |
| 6663 | Sox10 | -1.248 | 1.64E-29 | 2.04E-27 | SOX10 | -0.712 | 1.80E-01 | 5.30E-01 |
| 348938 | Nipal4 | -2.142 | 1.45E-26 | 1.62E-24 | NIPAL4 | -1.252 | 5.20E-02 | 3.30E-01 |
| 5010 | Cldn11 | -2.599 | 4.77E-26 | 5.23E-24 | CLDN11 | -0.411 | 4.10E-01 | 7.40E-01 |
| 6558 | Slc12a2 | -0.641 | 8.63E-26 | 9.28E-24 | SLC12A2 | -0.960 | 9.30E-03 | 1.50E-01 |
| 1902 | Lpar1 | -1.092 | 2.59E-25 | 2.72E-23 | LPAR1 | -1.574 | 3.60E-03 | 9.90E-02 |
| 9341 | Vamp3 | -0.740 | 1.36E-24 | 1.40E-22 | VAMP3 | -0.674 | 6.30E-02 | 3.50E-01 |
| 23187 | Phldb1 | -0.778 | 3.07E-24 | 3.09E-22 | PHLDB1 | -0.585 | 1.30E-01 | 4.70E-01 |
| 84061 | Magt1 | -1.154 | 2.31E-23 | 2.27E-21 | MAGT1 | -0.687 | 6.10E-02 | 3.50E-01 |
| 4864 | Npc1 | -0.753 | 3.77E-23 | 3.67E-21 | NPC1 | -0.544 | 2.40E-01 | 6.00E-01 |
| 64399 | Hhip | -0.979 | 5.17E-23 | 4.99E-21 | HHIP | -1.585 | 2.90E-03 | 8.70E-02 |
| 11240 | Padi2 | -1.352 | 8.66E-22 | 7.91E-20 | PADI2 | -0.798 | 1.10E-01 | 4.40E-01 |
| 11226 | Galnt6 | -1.734 | 8.76E-22 | 7.96E-20 | GALNT6 | -0.930 | 1.30E-01 | 4.60E-01 |
| 10110 | Sgk2 | -2.152 | 3.86E-21 | 3.31E-19 | SGK2 | -0.766 | 1.60E-01 | 5.10E-01 |
| 23241 | Pacs2 | -0.572 | 9.64E-21 | 8.10E-19 | PACS2 | -0.537 | 1.90E-01 | 5.50E-01 |
| 4099 | Mag | -2.536 | 1.09E-19 | 8.53E-18 | MAG | -0.944 | 8.80E-02 | 4.00E-01 |
| 6271 | S100a1 | -0.707 | 5.25E-19 | 3.98E-17 | S100A1 | -0.509 | 2.90E-01 | 6.50E-01 |
| 54893 | Mtmr10 | -0.634 | 2.46E-18 | 1.80E-16 | MTMR10 | -0.592 | 1.40E-01 | 4.80E-01 |

FIG. 15A

| Darbelli et al. (2017) (QKI Deficient vs QKI Proficient) | | | | Present Study (Blue module) | | | |
|---|---|---|---|---|---|---|---|
| Entrez ID | MGI symbol | log2 FC | p | adj p | Genes | log2 FC | p | adj p |

| Entrez ID | MGI symbol | log2 FC | p | adj p | Genes | log2 FC | p | adj p |
|---|---|---|---|---|---|---|---|---|
| 92521 | Specc1 | -0.504 | 6.78E-18 | 4.87E-16 | SPECC1 | -0.541 | 3.80E-02 | 2.90E-01 |
| 2581 | Galc | -0.602 | 8.24E-18 | 5.90E-16 | GALC | -0.545 | 7.50E-02 | 3.80E-01 |
| 116173 | Cmtm5 | -0.686 | 1.12E-17 | 7.93E-16 | CMTM5 | -1.367 | 9.10E-03 | 1.50E-01 |
| 1573 | Cyp2j9 | -0.907 | 1.18E-17 | 8.32E-16 | CYP2J2 | -1.022 | 3.30E-03 | 9.40E-02 |
| 5588 | Prkcq | -1.126 | 4.52E-17 | 3.12E-15 | PRKCQ | -1.061 | 7.50E-02 | 3.80E-01 |
| 9037 | Sema5a | -0.447 | 1.01E-16 | 6.90E-15 | SEMA5A | -0.661 | 1.10E-01 | 4.40E-01 |
| 28996 | Hipk2 | -0.790 | 4.25E-16 | 2.76E-14 | HIPK2 | -0.948 | 3.40E-02 | 2.70E-01 |
| 4642 | Myo1d | -1.037 | 5.02E-16 | 3.24E-14 | MYO1D | -1.023 | 2.90E-02 | 2.60E-01 |
| 5337 | Pld1 | -0.896 | 6.02E-16 | 3.87E-14 | PLD1 | -1.355 | 7.50E-03 | 1.40E-01 |
| 58473 | Plekhb1 | -0.770 | 6.85E-16 | 4.35E-14 | PLEKHB1 | -0.776 | 6.40E-02 | 3.50E-01 |
| 847 | Cat | -0.513 | 9.28E-16 | 5.81E-14 | CAT | -0.572 | 1.80E-01 | 5.40E-01 |
| 85377 | Micall1 | -0.622 | 1.23E-15 | 7.66E-14 | MICALL1 | -0.598 | 1.60E-01 | 5.00E-01 |
| 26030 | Plekhg3 | -0.857 | 2.16E-15 | 1.32E-13 | PLEKHG3 | -1.133 | 1.70E-02 | 2.00E-01 |
| 23239 | Phlpp1 | -0.453 | 2.32E-15 | 1.41E-13 | PHLPP1 | -0.596 | 1.60E-01 | 5.00E-01 |
| 80303 | Efhd1 | -1.137 | 7.02E-15 | 4.15E-13 | EFHD1 | -0.746 | 1.70E-01 | 5.20E-01 |
| 114793 | Fmnl2 | -0.517 | 9.64E-15 | 5.64E-13 | FMNL2 | -0.859 | 4.00E-02 | 2.90E-01 |
| 2346 | Folh1 | -1.724 | 5.92E-14 | 3.31E-12 | FOLH1 | -1.445 | 9.10E-03 | 1.50E-01 |
| 5638 | Prrg1 | -1.083 | 8.09E-14 | 4.50E-12 | PRRG1 | -1.080 | 4.50E-02 | 3.10E-01 |
| 1371 | Cpox | -0.565 | 1.45E-13 | 7.89E-12 | CPOX | -1.045 | 1.20E-02 | 1.70E-01 |
| 122060 | Slain1 | -0.451 | 2.06E-13 | 1.10E-11 | SLAIN1 | -0.743 | 4.40E-02 | 3.00E-01 |
| 159195 | Usp54 | -0.565 | 2.39E-13 | 1.26E-11 | USP54 | -0.823 | 5.10E-02 | 3.20E-01 |
| 2549 | Gab1 | -0.712 | 2.63E-13 | 1.37E-11 | GAB1 | -0.920 | 3.20E-02 | 2.70E-01 |
| 55619 | Dock10 | -0.769 | 3.58E-13 | 1.83E-11 | DOCK10 | -1.254 | 1.10E-02 | 1.60E-01 |
| 94015 | Ttyh2 | -0.581 | 4.82E-13 | 2.44E-11 | TTYH2 | -1.143 | 3.20E-02 | 2.70E-01 |
| 11342 | Rnf13 | -0.462 | 1.17E-12 | 5.82E-11 | RNF13 | -1.002 | 6.80E-03 | 1.30E-01 |
| 57458 | Tmcc3 | -0.785 | 1.44E-12 | 7.12E-11 | TMCC3 | -0.624 | 2.40E-01 | 5.90E-01 |
| 54820 | Nde1 | -0.592 | 1.57E-12 | 7.66E-11 | NDE1 | -1.419 | 1.10E-02 | 1.70E-01 |
| 56957 | Otud7b | -0.621 | 1.58E-12 | 7.72E-11 | OTUD7B | -0.613 | 6.00E-02 | 3.50E-01 |
| 60484 | Hapln2 | -2.027 | 2.88E-12 | 1.37E-10 | HAPLN2 | -0.878 | 8.00E-02 | 3.90E-01 |
| 2824 | Gpm6b | -0.511 | 3.96E-12 | 1.88E-10 | GPM6B | -0.418 | 2.60E-01 | 6.20E-01 |
| 84886 | 310022B05R | -0.587 | 7.86E-12 | 3.57E-10 | C1orf198 | -0.488 | 3.00E-01 | 6.50E-01 |
| 79905 | Tmc7 | -0.577 | 8.26E-12 | 3.73E-10 | TMC7 | -1.049 | 5.20E-03 | 1.20E-01 |
| 1595 | Cyp51 | -0.421 | 1.01E-11 | 4.47E-10 | CYP51A1 | -0.381 | 2.80E-01 | 6.40E-01 |
| 9728 | Secisbp2l | -0.523 | 1.31E-11 | 5.76E-10 | SECISBP2L | -0.927 | 7.60E-03 | 1.40E-01 |
| 5412 | Ubl3 | -0.374 | 1.76E-11 | 7.64E-10 | UBL3 | -0.643 | 1.80E-02 | 2.10E-01 |
| 9802 | Dazap2 | -0.407 | 2.01E-11 | 8.70E-10 | DAZAP2 | -0.276 | 3.30E-01 | 6.80E-01 |
| 9061 | Papss1 | -0.393 | 2.25E-11 | 9.70E-10 | PAPSS1 | -0.658 | 7.70E-02 | 3.80E-01 |
| 23313 | 331439G07R | -0.368 | 3.89E-11 | 1.63E-09 | KIAA0930 | -0.506 | 2.00E-01 | 5.50E-01 |
| 23258 | Dennd5a | -0.363 | 8.88E-11 | 3.58E-09 | DENND5A | -0.693 | 1.00E-02 | 1.60E-01 |
| 117584 | Rffl | -0.600 | 8.90E-11 | 3.58E-09 | RFFL | -0.774 | 1.10E-01 | 4.40E-01 |
| 5129 | Cdk18 | -0.633 | 2.82E-10 | 1.11E-08 | CDK18 | -0.846 | 2.10E-01 | 5.70E-01 |
| 2339 | Fnta | -0.455 | 3.90E-10 | 1.52E-08 | FNTA | -0.803 | 1.80E-02 | 2.10E-01 |
| 5962 | Rdx | -0.453 | 7.14E-10 | 2.71E-08 | RDX | -0.877 | 1.70E-02 | 2.00E-01 |
| 2705 | Gjb1 | -1.557 | 8.11E-10 | 3.06E-08 | GJB1 | -1.292 | 8.40E-02 | 4.00E-01 |
| 84890 | Ado | -0.392 | 8.28E-10 | 3.12E-08 | ADO | -0.540 | 1.50E-01 | 4.90E-01 |
| 9444 | Qk | 0.325 | 1.05E-09 | 3.92E-08 | QKI | -0.747 | 7.40E-02 | 3.80E-01 |
| 55032 | Slc35a5 | -0.428 | 1.33E-09 | 4.89E-08 | SLC35A5 | -0.420 | 3.00E-01 | 6.50E-01 |
| 9448 | Map4k4 | -0.404 | 1.48E-09 | 5.44E-08 | MAP4K4 | -1.166 | 4.90E-03 | 1.20E-01 |
| 9725 | Tmem63a | -0.692 | 1.88E-09 | 6.71E-08 | TMEM63A | -1.092 | 6.00E-02 | 3.50E-01 |
| 2047 | Ephb1 | -0.420 | 2.43E-09 | 8.55E-08 | EPHB1 | 1.121 | 6.40E-02 | 3.50E-01 |
| 4340 | Mog | -2.116 | 4.56E-09 | 1.56E-07 | MOG | -1.042 | 6.50E-02 | 3.60E-01 |
| 5046 | Pcsk6 | -0.673 | 6.67E-09 | 2.24E-07 | PCSK6 | -0.801 | 1.40E-01 | 4.80E-01 |
| 256435 | St6galnac3 | -0.740 | 6.75E-09 | 2.26E-07 | T6GALNAC | -0.907 | 1.70E-02 | 2.00E-01 |

FIG. 15B

| Darbelli et al. (2017) (QKI Deficient vs QKI Proficient) | | | | Present Study (Blue module) | | | |
|---|---|---|---|---|---|---|---|
| Entrez ID | MGI symbol | log2 FC | p | adj p | Genes | log2 FC | p | adj p |
| 65125 | Wnk1 | -0.353 | 8.35E-09 | 2.76E-07 | WNK1 | -0.790 | 3.70E-02 | 2.90E-01 |
| 6856 | Sypl | -0.430 | 9.72E-09 | 3.17E-07 | SYPL1 | -0.997 | 2.70E-02 | 2.50E-01 |
| 94274 | Ppp1r14a | -1.543 | 9.76E-09 | 3.18E-07 | PPP1R14A | -1.205 | 3.80E-02 | 2.90E-01 |
| 1495 | Ctnna1 | -0.324 | 1.11E-08 | 3.60E-07 | CTNNA1 | -0.347 | 3.40E-01 | 6.90E-01 |
| 54443 | Anln | -0.593 | 1.50E-08 | 4.71E-07 | ANLN | -1.311 | 2.10E-02 | 2.20E-01 |
| 79957 | Paqr6 | -1.229 | 1.54E-08 | 4.80E-07 | PAQR6 | -1.144 | 3.90E-02 | 2.90E-01 |
| 30812 | Sox8 | -0.413 | 1.97E-08 | 6.05E-07 | SOX8 | -0.861 | 1.10E-01 | 4.40E-01 |
| 53637 | S1pr5 | -1.177 | 2.04E-08 | 6.24E-07 | S1PR5 | -0.843 | 1.50E-01 | 4.90E-01 |
| 387 | Rhoa | -0.266 | 2.34E-08 | 7.07E-07 | RHOA | -0.228 | 4.30E-01 | 7.50E-01 |
| 91369 | Ankrd40 | -0.337 | 2.34E-08 | 7.07E-07 | ANKRD40 | -0.793 | 3.00E-02 | 2.60E-01 |
| 56062 | Klhl4 | -0.491 | 5.57E-08 | 1.59E-06 | KLHL4 | -1.166 | 2.10E-02 | 2.20E-01 |
| 333 | Aplp1 | -0.253 | 6.20E-08 | 1.76E-06 | APLP1 | -0.987 | 4.60E-02 | 3.10E-01 |
| 6888 | Taldo1 | -0.411 | 6.27E-08 | 1.78E-06 | TALDO1 | -0.597 | 3.70E-02 | 2.80E-01 |
| 55861 | Dbndd2 | -0.306 | 8.20E-08 | 2.30E-06 | DBNDD2 | -1.308 | 1.10E-02 | 1.60E-01 |
| 3306 | Hspa2 | -0.331 | 8.51E-08 | 2.38E-06 | HSPA2 | -0.830 | 1.50E-01 | 5.00E-01 |
| 83641 | Fam107b | -0.432 | 1.53E-07 | 4.12E-06 | FAM107B | -1.042 | 8.80E-03 | 1.50E-01 |
| 93643 | Tjap1 | -0.626 | 1.88E-07 | 4.97E-06 | TJAP1 | -0.854 | 7.70E-02 | 3.80E-01 |
| 1287 | Col4a5 | 0.528 | 1.99E-07 | 5.23E-06 | COL4A5 | -1.065 | 3.80E-02 | 2.90E-01 |
| 219654 | Zcchc24 | -0.404 | 3.21E-07 | 8.16E-06 | ZCCHC24 | -0.662 | 1.10E-01 | 4.40E-01 |
| 7456 | Wipf1 | -0.420 | 4.26E-07 | 1.07E-05 | WIPF1 | -0.782 | 1.20E-01 | 4.50E-01 |
| 51114 | Zdhhc9 | -0.321 | 6.24E-07 | 1.53E-05 | ZDHHC9 | -1.261 | 3.40E-03 | 9.50E-02 |
| 8549 | Lgr5 | 0.825 | 6.36E-07 | 1.56E-05 | LGR5 | -1.016 | 1.00E-01 | 4.20E-01 |
| 25938 | Heatr5a | -0.458 | 7.39E-07 | 1.80E-05 | HEATR5A | -0.374 | 2.30E-01 | 5.90E-01 |
| 5523 | Ppp2r3a | -0.403 | 9.12E-07 | 2.18E-05 | PPP2R3A | -0.750 | 4.20E-02 | 3.00E-01 |
| 20 | Abca2 | -0.232 | 9.93E-07 | 2.35E-05 | ABCA2 | -0.756 | 1.20E-01 | 4.50E-01 |
| 83543 | Aif1l | 0.665 | 1.00E-06 | 2.36E-05 | AIF1L | -1.168 | 1.10E-02 | 1.60E-01 |
| 150356 | Chadl | -0.484 | 1.11E-06 | 2.61E-05 | CHADL | -1.044 | 5.60E-02 | 3.40E-01 |
| 9717 | Sec14l5 | -1.305 | 1.44E-06 | 3.29E-05 | SEC14L5 | -1.263 | 3.10E-02 | 2.60E-01 |
| 10435 | Cdc42ep2 | -0.483 | 1.78E-06 | 4.02E-05 | CDC42EP2 | -0.526 | 3.00E-01 | 6.60E-01 |
| 203190 | Lgi3 | -0.478 | 1.84E-06 | 4.14E-05 | LGI3 | -0.836 | 3.30E-02 | 2.70E-01 |
| 3688 | Itgb1 | -0.282 | 1.88E-06 | 4.21E-05 | ITGB1 | -0.488 | 1.10E-01 | 4.30E-01 |
| 84504 | Nkx6-2 | -0.805 | 2.05E-06 | 4.56E-05 | NKX6-2 | -0.581 | 3.20E-01 | 6.70E-01 |
| 950 | Scarb2 | -0.358 | 3.74E-06 | 8.01E-05 | SCARB2 | -0.774 | 1.00E-02 | 1.60E-01 |
| 55314 | Tmem144 | -0.707 | 5.63E-06 | 1.16E-04 | TMEM144 | -0.931 | 7.00E-02 | 3.70E-01 |
| 51097 | Sccpdh | -0.330 | 7.06E-06 | 1.41E-04 | SCCPDH | -0.500 | 1.90E-01 | 5.40E-01 |
| 220296 | Hepacam | -0.357 | 7.10E-06 | 1.42E-04 | HEPACAM | -0.364 | 3.60E-01 | 7.00E-01 |
| 286827 | Trim59 | -0.456 | 8.80E-06 | 1.73E-04 | TRIM59 | -1.873 | 1.70E-03 | 7.00E-02 |
| 11076 | Tppp | -0.336 | 9.70E-06 | 1.89E-04 | TPPP | -0.641 | 7.40E-02 | 3.70E-01 |
| 26022 | Tmem98 | -0.586 | 1.77E-05 | 3.30E-04 | TMEM98 | -0.932 | 6.10E-02 | 3.50E-01 |
| 158747 | Mospd2 | -0.402 | 1.77E-05 | 3.30E-04 | MOSPD2 | -1.002 | 1.10E-02 | 1.60E-01 |
| 22875 | Enpp4 | -0.358 | 2.59E-05 | 4.70E-04 | ENPP4 | -0.758 | 4.50E-02 | 3.10E-01 |
| 85414 | Slc45a3 | -1.162 | 4.85E-05 | 8.28E-04 | SLC45A3 | -1.015 | 9.90E-02 | 4.20E-01 |
| 23232 | Tbc1d12 | -0.403 | 4.92E-05 | 8.38E-04 | TBC1D12 | -0.845 | 2.00E-02 | 2.20E-01 |
| 5101 | Pcdh9 | -0.244 | 5.25E-05 | 8.86E-04 | PCDH9 | -0.945 | 7.00E-03 | 1.40E-01 |
| 23677 | Sh3bp4 | -0.426 | 5.56E-05 | 9.35E-04 | SH3BP4 | -0.760 | 8.30E-02 | 3.90E-01 |
| 256987 | Serinc5 | -0.342 | 6.47E-05 | 1.07E-03 | SERINC5 | -0.553 | 2.30E-01 | 5.90E-01 |
| 9265 | Cyth3 | 0.254 | 6.52E-05 | 1.08E-03 | CYTH3 | 0.249 | 4.40E-01 | 7.50E-01 |
| 6801 | Strn | -0.357 | 6.86E-05 | 1.13E-03 | STRN | -0.750 | 9.20E-03 | 1.50E-01 |
| 118442 | Gpr62 | -0.458 | 8.48E-05 | 1.36E-03 | GPR62 | -0.939 | 9.20E-02 | 4.10E-01 |
| 6299 | Sall1 | 0.394 | 8.89E-05 | 1.42E-03 | SALL1 | -0.712 | 1.40E-01 | 4.80E-01 |
| 22795 | Nid2 | 0.398 | 9.46E-05 | 1.51E-03 | NID2 | -0.370 | 5.70E-01 | 8.30E-01 |
| 10397 | Ndrg1 | -0.526 | 1.09E-04 | 1.72E-03 | NDRG1 | -0.608 | 2.40E-01 | 6.00E-01 |
| 1793 | Dock1 | -0.374 | 1.14E-04 | 1.78E-03 | DOCK1 | -0.796 | 5.70E-02 | 3.40E-01 |

FIG. 15C

| Darbelli et al. (2017) (QKI Deficient vs QKI Proficient) | | | | | Present Study (Blue module) | | | |
|---|---|---|---|---|---|---|---|---|
| Entrez ID | MGI symbol | log2 FC | p | adj p | Genes | log2 FC | p | adj p |
| 928 | Cd9 | -0.343 | 1.21E-04 | 1.87E-03 | CD9 | -0.590 | 1.30E-01 | 4.70E-01 |
| 123606 | Nipa1 | -0.276 | 1.30E-04 | 1.98E-03 | NIPA1 | -0.952 | 9.90E-03 | 1.60E-01 |
| 2123 | Evi2a | -0.488 | 1.96E-04 | 2.84E-03 | EVI2A | -0.950 | 8.70E-02 | 4.00E-01 |
| 3759 | Kcnj2 | -0.391 | 2.20E-04 | 3.13E-03 | KCNJ2 | -0.979 | 8.60E-02 | 4.00E-01 |
| 79789 | Clmn | -0.458 | 2.26E-04 | 3.19E-03 | CLMN | -0.793 | 1.20E-01 | 4.40E-01 |
| 154215 | Nkain2 | -0.306 | 2.48E-04 | 3.45E-03 | NKAIN2 | -1.066 | 1.50E-02 | 1.90E-01 |
| 54894 | Rnf43 | 0.570 | 2.49E-04 | 3.46E-03 | RNF43 | 2.115 | 4.10E-03 | 1.10E-01 |
| 91775 | Nxpe3 | 0.277 | 3.55E-04 | 4.67E-03 | NXPE3 | -0.544 | 1.10E-01 | 4.30E-01 |
| 8496 | Ppfibp1 | -0.285 | 3.98E-04 | 5.16E-03 | PPFIBP1 | -0.746 | 1.30E-01 | 4.60E-01 |
| 79817 | Mob3b | -0.615 | 4.13E-04 | 5.34E-03 | MOB3B | -0.739 | 8.20E-02 | 3.90E-01 |
| 7444 | Vrk2 | 0.494 | 4.41E-04 | 5.65E-03 | VRK2 | -0.864 | 1.40E-01 | 4.80E-01 |
| 9625 | Aatk | -0.234 | 4.69E-04 | 5.95E-03 | AATK | -0.422 | 3.20E-01 | 6.70E-01 |
| 57571 | Carns1 | -0.470 | 6.05E-04 | 7.45E-03 | CARNS1 | -1.404 | 1.20E-02 | 1.70E-01 |
| 57636 | Arhgap23 | -0.176 | 6.97E-04 | 8.38E-03 | ARHGAP23 | -0.409 | 3.00E-01 | 6.60E-01 |
| 9053 | Map7 | -0.284 | 7.11E-04 | 8.52E-03 | MAP7 | -0.518 | 6.20E-02 | 3.50E-01 |
| 10157 | Aass | 0.799 | 8.10E-04 | 9.53E-03 | AASS | -0.653 | 3.00E-02 | 2.60E-01 |
| 5334 | Plcl1 | -0.282 | 8.61E-04 | 1.00E-02 | PLCL1 | -1.190 | 7.90E-03 | 1.40E-01 |
| 58478 | Enoph1 | -0.206 | 1.10E-03 | 1.24E-02 | ENOPH1 | -0.286 | 4.80E-01 | 7.80E-01 |
| 5879 | Rac1 | -0.151 | 1.10E-03 | 1.25E-02 | RAC1 | -0.377 | 1.30E-01 | 4.60E-01 |
| 9026 | Hip1r | -0.210 | 1.14E-03 | 1.27E-02 | HIP1R | -0.693 | 1.20E-01 | 4.50E-01 |
| 6242 | Rtkn | -0.309 | 1.22E-03 | 1.35E-02 | RTKN | -0.854 | 6.00E-02 | 3.50E-01 |
| 51128 | Sar1b | -0.202 | 1.38E-03 | 1.50E-02 | SAR1B | -0.554 | 6.80E-02 | 3.60E-01 |
| 23632 | Car14 | -0.434 | 1.41E-03 | 1.52E-02 | CA14 | -0.887 | 1.30E-01 | 4.60E-01 |
| 56895 | Agpat4 | -0.191 | 1.45E-03 | 1.56E-02 | AGPAT4 | -1.153 | 7.60E-03 | 1.40E-01 |
| 112399 | Egln3 | 0.311 | 1.50E-03 | 1.60E-02 | EGLN3 | -0.661 | 1.10E-01 | 4.40E-01 |
| 25777 | Sun2 | 0.216 | 1.62E-03 | 1.71E-02 | SUN2 | -0.431 | 2.50E-01 | 6.00E-01 |
| 6642 | Snx1 | -0.186 | 1.70E-03 | 1.77E-02 | SNX1 | -0.610 | 5.20E-02 | 3.30E-01 |
| 138639 | Ptpdc1 | -0.250 | 1.87E-03 | 1.91E-02 | PTPDC1 | -0.699 | 3.10E-02 | 2.60E-01 |
| 10396 | Atp8a1 | -0.241 | 2.68E-03 | 2.59E-02 | ATP8A1 | -1.011 | 3.90E-03 | 1.00E-01 |
| 55858 | Tmem165 | -0.193 | 3.32E-03 | 3.11E-02 | TMEM165 | -0.666 | 1.20E-01 | 4.40E-01 |
| 220965 | Fam13c | -0.156 | 3.54E-03 | 3.27E-02 | FAM13C | -1.101 | 1.00E-02 | 1.60E-01 |
| 64788 | Lmf1 | -0.273 | 3.95E-03 | 3.57E-02 | LMF1 | -0.636 | 1.80E-01 | 5.30E-01 |
| 399694 | Shc4 | -0.381 | 3.95E-03 | 3.57E-02 | SHC4 | -1.050 | 2.40E-02 | 2.40E-01 |
| 50859 | Spock3 | -0.238 | 4.36E-03 | 3.87E-02 | SPOCK3 | -1.307 | 1.50E-03 | 6.60E-02 |
| 9420 | Cyp7b1 | -0.261 | 4.66E-03 | 4.11E-02 | CYP7B1 | -1.286 | 3.50E-03 | 9.80E-02 |
| 58476 | Trp53inp2 | -0.181 | 4.99E-03 | 4.35E-02 | TP53INP2 | -1.343 | 5.20E-02 | 3.30E-01 |
| 9517 | Sptlc2 | -0.224 | 5.04E-03 | 4.38E-02 | SPTLC2 | -0.818 | 6.40E-02 | 3.50E-01 |
| 214 | Alcam | -0.257 | 5.08E-03 | 4.41E-02 | ALCAM | -1.054 | 3.40E-02 | 2.70E-01 |
| 5151 | Pde8a | -0.369 | 5.66E-03 | 4.82E-02 | PDE8A | -0.929 | 4.70E-02 | 3.10E-01 |

FIG. 15D

METHODS OF DETECTING AND TREATING MULTIPLE SYSTEM ATROPHY

CROSS REFERENCE TO RELATED APPLICATIONS

This application claims the benefit of U.S. Provisional Patent Application No. 63/034,526, filed Jun. 4, 2020, titled "Methods for Detecting and Treating Multiple System Atrophy," the entirety of which is hereby incorporated herein by this reference.

FIELD

The present invention is related to compositions and methods of detecting and treating disease, and more particularly, compositions and methods of detecting and treating neurodegenerative disease.

BACKGROUND

Multiple-system atrophy (MSA) is a rare neurodegenerative disorder characterized by autonomic dysfunction, ataxia, and parkinsonism. The prevalence is estimated to be between 1.9 to 4.9 per 100,000 [10, 67]. The disease affects both sexes equally with onset typically in the sixth decade of life and with an average survival after diagnosis of less than ten years [67]. There are no effective long-term therapeutic options for the MSA patient, and no cure.

MSA as a unifying diagnostic terminology was developed to encapsulate three neurological entities: striatonigral degeneration, olivopontocerebellar atrophy, and Shy-Drager syndrome [28, 55, 73, 74]. Two different clinical subtypes have been described based on the predominating motor features noted during the early stages of the disease: the MSA-P subtype (dominated by parkinsonism) and the MSA-C subtype (dominated by cerebellar ataxia). However, in the later stages of the disease, the phenotypic characteristics of both subtypes are typically noted in the patient [18]. A definitive diagnosis of MSA is obtained through autopsy confirmation of a high density of α-synuclein-containing protein aggregates, known as glial cytoplasmic inclusion (GCI) bodies, in oligodendrocytes along with striatonigral degeneration and/or olivopontocerebellar atrophy [10, 52, 67].

GCIs are primarily comprised of aggregated α-synuclein, therefore MSA can be classified as an oligodendroglial α-synucleinopathy, which is a point of distinction compared to neuronal α-synucleinopathies like Parkinson's disease. Interestingly, work investigating the earliest molecular changes associated with MSA has suggested that oligodendrocyte intracellular accumulation of p25α, a protein associated with myelination, may be altered before α-synuclein aggregation is observed [67]. The aggregation of α-synuclein is thought to lead to a disruption of the role of the oligodendrocyte in the process of neuronal myelination leading to microglial activation and subsequent release of mis-folded α-synuclein by the increasingly dysfunctional oligodendrocytes. Neighboring neurons may uptake this extracellular α-synuclein and it could thereby initiate new aggregation inside the neuronal cell. Additionally, the toxic α-synuclein species may spread to neurons in other synaptically-connected brain regions in a prion-like fashion. The lack of effective oligodendrocyte support for the local neurons, and the neuronal effects of the α-synuclein inclusions, eventually results in axonal dysfunction, neuronal cell death, and a reactive astrogliosis [18].

The cause of MSA is not known, however it is generally believed to be sporadic. Several genomic studies have been performed to shed light on the molecular pathogenesis of the disease. Three single nucleotide polymorphisms (SNPs) located in the α-synuclein gene (SCNA) have been associated with the risk of developing MSA [60]. In an independent study conducted by evaluating 32 SNPs in the SNCA gene, one SNP associated with MSA and one haplotype associated with the MSA-C subgroup were noted [2]. Whole genome sequencing analysis identified COQ2 genetic variants associated with both sporadic and familial MSA [47], and this finding was replicated in other Asian cohorts [41, 79]. In another GWAS, including MSA patients and healthy controls, several SNPs located in different genes (FBX047, ELOVL7, EDN1, and MAPT) were found to be potentially associated, but were not significant after multiple test correction [59]. Finally, the presence of an expansion of one allele in SCA3 (a gene associated with spinocerebellar ataxia) was observed in a patient showing clinical features consistent with MSA-C [48]. Recently, epigenetic modifications, such as DNA methylation changes, have also been identified in neurodegenerative diseases. A recent study reported white matter tissue DNA methylation changes associated with MSA, including changes in HIP1, LMAN2 and MOBP [9].

Three different gene expression profiling studies conducted on neuropathologically verified human brain samples have been reported to date. The first study [45] utilized transcriptome profiling by RNA-sequencing of the white and grey matter of the frontal cortex from 6 MSA patients and 6 controls. In the grey matter they detected 5 genes differentially expressed (HLA-A, HLA-B, HLA-C, TTR and LOC389831). In the white matter they identified 7 genes, including the 3 HLA genes detected in the grey matter. The additional genes were: HBA1, HBA2, HBB and IL1RL1. The SNCA gene was detected to be upregulated in both comparisons, but it was not statistically significant. They also compared the white matter versus the grey matter in patients, detecting a total of 1,910 differentially expressed genes. A second study was conducted using the same 12 samples, but using strand-specific RNA-sequencing [46], detecting a total of 123 differentially expressed genes. Most detected genes were lincRNAs or un-annotated transcripts. Some of the genes found in the previous study [45] were confirmed; HBB, IL1RL1, TTR and LOC389831. Finally, a study determining the differential expression of circular RNA (circRNA) in the MSA frontal cortex was conducted [14], identifying 5 circRNAs produced by backsplicing of the precursor mRNAs from the IQCK, EFCAB11, DTNA, MAP4K3, and MCTP1 genetic loci. No other RNA sequencing studies have been conducted thus far.

SUMMARY

A need exists for a diagnostic and therapeutic strategy for treatment of neurodegenerative diseases, including multiple-system atrophy (MSA). The present disclosure includes methods for diagnosing and treating a patient or a subject having MSA. The present disclosure has identified diagnostic targets for MSA, as well as compositions and methods for treating a subject having MSA. The treatment or therapeutic agent may include a peroxisome proliferator-activated receptor β (PPARβ) agonist and/or a retinoid X receptor (RXR) agonist.

The current method of identifying MSA in a patient relies on the process of elimination where other neurodegenerative conditions are slowly ruled out eventually leaving MSA as the ultimate diagnosis. This process wastes valuable time and limits the efficacy of any treatments that might be administered to the subject suffering from MSA. The present disclosure addresses these limitations by allowing earlier identification of MSA. Comparing the subject-derived expression level of one or more genes identified herein with a normal control expression level of the gene(s) provides early detection of MSA in the subject. Moreover, the disclosed methods allow for the differentiation of MSA from other synucleinopathies including Parkinson's disease (PD) and dementia with Lewy bodies (DLB) based on the unique molecular mechanisms underlying the pathologies in MSA (e.g., QKI deficiency-induced demyelination). This differentiation of MSA from other synucleinopathies based on the unique molecular mechanisms underlying its pathologies also allows for tailored treatment of MSA with a peroxisome proliferator-activated receptor β (PPARβ) agonist and/or a retinoid X receptor (RXR) agonist.

In certain aspects, the disclosure provides a method of diagnosing and treating a neurodegenerative disease, MSA, in a subject may comprise the steps of determining in a subject-derived biological sample an expression level of a gene from the group consisting of QKI, GGCX, MOCS1, NF1, LINC01572, PRRG3, HMBOX1, PLP1, PPP1CA, C8orf88, TGFB2, MASP1, TIAM1, SYNGAP1, ACTN1, EMP1, NFIL3, GPNMB, PGAM2, ST5, STON1, RFTN1, ACTN1, and MMP14. The MSA may be parkinsonian MSA (MSA-P) or cerebellar MSA (MSA-C). The method may further include the steps of comparing the subject-derived expression level of the gene with a normal control expression level of the gene obtained from non-neurodegenerative biological sample, diagnosing the subject as a having MSA by detecting a differential expression of the gene in the a subject-derived biological sample as compared to the normal control expression level, and administering a peroxisome proliferator-activated receptor β (PPARβ) agonist and/or a retinoid X receptor (RXR) agonist to the subject diagnosed as having MSA.

The RXR agonist may include Bexarotene, CD 3254, Docosahexaenoic acid, Fluorobexarotene, LG 100268, Retinoic acid, SR 11237, LG100754, and Magnolol or a combination thereof. The PPARβ agonist may include Ertiprotafib, GW0742, GW610742, Retinoic acid, and KD3010 or a combination thereof.

In one aspect, where the differentially expressed gene is QKI, the expression level of QKI in the subject-derived biological sample being downregulated as compared to the normal control expression level indicates the subject has MSA.

In another aspect, where the differentially expressed gene is ACTN1, the expression level of ACTN1 in the subject-derived biological sample being upregulated as compared to the normal control expression level indicates the subject has MSA.

In another aspect, where the differentially expressed gene is EMP1, the expression level of EMP1 in the subject-derived biological sample being upregulated as compared to the normal control expression level indicates the subject has MSA.

In another aspect, where the differentially expressed gene is NFIL3, the expression level of NFIL3 in the subject-derived biological sample being upregulated as compared to the normal control expression level indicates the subject has MSA.

In another aspect, where the differentially expressed gene is GPNMB, the expression level of GPNMB in the subject-derived biological sample being upregulated as compared to the normal control expression level indicates the subject has MSA.

In another aspect, where the differentially expressed gene is TGFB2, the expression level of TGFB2 in the subject-derived biological sample being upregulated as compared to the normal control expression level indicates the subject has MSA.

In another aspect, where the differentially expressed gene is TIAM1, the expression level of TIAM1 in the subject-derived biological sample being upregulated as compared to the normal control expression level indicates the subject has MSA.

In another aspect, where the differentially expressed gene is SYNGAP1, the expression level of SYNGAP1 in the subject-derived biological sample being upregulated as compared to the normal control expression level indicates the subject has MSA.

In another aspect, where the differentially expressed gene is PGAM2, and the expression level of PGAM2 in the subject-derived biological sample is upregulated as compared to the normal control expression level.

In another aspect, where the differentially expressed gene is ST5, and the expression level of ST5 in the subject-derived biological sample is upregulated as compared to the normal control expression level.

In another aspect, where the differentially expressed gene is STON1, and the expression level of STON1 in the subject-derived biological sample is upregulated as compared to the normal control expression level.

In another aspect, where the differentially expressed gene is RFTN1, and the expression level of RFTN1 in the subject-derived biological sample is upregulated as compared to the normal control expression level.

In another aspect, where the differentially expressed gene is MMP14, and the expression level of MMP14 in the subject-derived biological sample is upregulated as compared to the normal control expression level.

In another aspect, where the differentially expressed gene is GGCX, and the expression level of GGCX in the subject-derived biological sample is upregulated as compared to the normal control expression level.

In another aspect, where the differentially expressed gene is MOCS1, and the expression level of GGCX in the subject-derived biological sample is downregulated as compared to the normal control expression level.

In another aspect, where the differentially expressed gene is NF1, and the expression level of NF1 in the subject-derived biological sample is downregulated as compared to the normal control expression level.

In another aspect, where the differentially expressed gene is LINC01572, and the expression level of LINC01572 in the subject-derived biological sample is downregulated as compared to the normal control expression level.

In another aspect, where the differentially expressed gene is PRRG3, and the expression level of PRRG3 in the subject-derived biological sample is downregulated as compared to the normal control expression level.

In another aspect, where the differentially expressed gene is PLP1, and the expression level of PLP1 in the subject-derived biological sample is downregulated as compared to the normal control expression level.

In another aspect, where the differentially expressed gene is MASP1, and the expression level of MASP1 in the subject-derived biological sample is upregulated as compared to the normal control expression level.

In some aspects, the expression level of the gene is downregulated and the expression level of the gene in the subject-derived biological sample is decreased by at least 10%, at least 20%, at least 30%, at least 40%, at least 50%, at least 60%, at least 70%, at least 80%, or at least 90% as compared to the normal control expression level indicating the subject has MSA.

In other aspects, the expression level of the gene is upregulated and the expression level of the gene in the subject-derived biological sample is increased by at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, or at least 3 fold as compared to the normal control expression level indicating the subject has MSA.

In certain aspects, the disclosure provides a method for diagnosing and treating a neurodegenerative disease in a subject, the method comprising: determining in a subject-derived biological sample an expression level of a gene from the group consisting of: QKI, GGCX, MOCS1, NF1, LINC01572, PRRG3, HMBOX1, PLP1, PPP1CA, C8orf88, TGFB2, MASP1, TIAM1, SYNGAP1, ACTN1, EMP1, NFIL3, GPNMB, PGAM2, ST5, STON1, RFTN1, ACTN1, and MMP14; comparing the subject-derived expression level of the gene with a normal control expression level of the gene obtained from a non-neurodegenerative biological sample; diagnosing the subject as a having the neurodegenerative disease by detecting a differential expression of the gene in the a subject-derived biological sample as compared to the normal control expression level; and administering a peroxisome proliferator-activated receptor β (PPARβ) agonist and/or a retinoid X receptor (RXR) agonist to the subject diagnosed as having the neurodegenerative disease.

In some aspects, the neurodegenerative disease is selected from the group consisting of Alzheimer's disease, progressive supranuclear palsy, multiple system atrophy, olivopontocerebellar atrophy (OPCA), Shy-Drager syndrome, striatonigral degeneration, Huntington's disease, amyotrophic lateral sclerosis (ALS), essential tremor, cortico-basal ganglionic degeneration, Pick's disease, cerebral ischemia, and cerebral infarction.

In one aspect, the biological sample comprises whole blood, red blood cells, plasma, serum, peripheral blood mononuclear cells (PBMCs), urine, saliva, tears, buccal swabs, cerebrospinal fluid (CSF), central nervous system (CNS) microdialysate, or nerve tissue.

In some aspects, the disclosure provides a method of treating a subject having multiple-system atrophy (MSA), the method comprising the step of administering to the subject a therapeutically effective amount of a peroxisome proliferator-activated receptor β (PPARβ) agonist and/or a retinoid X receptor (RXR) agonist.

In yet another aspect, the administration is oral, parenteral, rectal or transdermal administration. In one aspect, the method of treatment further comprises administration of adjunctive therapy including, but not limited to, levodopa, dopamine agonists, glutamine antagonists, orthostatic hypotension therapeutics, or anticholinergics.

The foregoing features and elements may be combined in various combinations without exclusivity, unless expressly indicated otherwise. These features and elements as well as the operation thereof will become more apparent in light of the following description. It should be understood, however, the following description is intended to be exemplary in nature and non-limiting.

BRIEF DESCRIPTION OF THE FIGURES

The patent or application file contains at least one drawing executed in color. Copies of this patent or patent application publication with color drawing(s) will be provided by the Office upon request and payment of the necessary fee.

Illustrative and exemplary embodiments of the invention are shown in the drawings in which:

FIG. 1A shows MSA; FIG. 1B shows MSA-P; FIG. 1C shows MSA-C; FIG. 1D shows LCM Oligodendrocytes;

FIGS. 2A and 2B illustrate differentially expressed genes found in MSA (FIG. 2A) and MSA-C (FIG. 2B);

FIG. 6A shows a cluster dendrogram showing the 9 coexpression modules detected in MSA-C(C1); FIG. 6B shows a volcano plot representing the results of the differential expression of the eigengene modules between MSA-C vs HC;

FIG. 7A shows a network for the yellow module, upregulated in MSA-C, edges are represented with weight ≥0.05; FIG. 7B shows a network for the blue module, downregulated in MSA-C, edges are represented with weight ≥0.20; FIG. 7C shows a network for the brown module, upregulated in MSA-C, edges are represented with weight ≥0.20; FIG. 7D shows a network for the green module, upregulated in MSA-C, edges are represented with weight ≥0.01;

FIG. 8A shows comparison between log 2 FC of the overlapping 196 genes (ρ=0.311; 8.0E-06); rge results do not change significantly after removing the two genes showing extreme log 2 FC in our data (ρ=0.300; ρ=1.9E-05); FIG. 8B shows gene-set enrichment analysis conducted to investigate the enrichment of QKI module genes in the list of DEGs from [19]; we detected a significant enrichment across downregulated genes (Enrichment Score=−0.627; p=1.07E-05);

FIG. 9 illustrates top genes for the different MSA subtypes after p-value combination; downregulated genes are reported in grey;

FIGS. 10A and 10B illustrate top results of the functional module discovery analysis using the DEGs identified in MSA-C;

FIG. 11 illustrates top genes differentially expressed in oligodendrocytes in MSA vs HC;

FIGS. 12A and 12B illustrate differentially expressed genes detected in the cohort 1 and cohort 2 in MSA;

FIG. 13 illustrates differentially expressed genes detected in the cohort 1 and cohort 2 in MSA-P;

FIG. 14 illustrates top 10 results after p value combination of the differential expression results (MSA-C vs MSA-P) from the two MSA-C cohorts; no genes showed significance after multiple test correction;

FIGS. 15A-15D illustrate comparison between the differentially expressed genes obtained in the study from Darbelli et al. (2017) involving mice with excised QKI-exon 2 (QKI deficient) versus QKI-proficient.

DETAILED DESCRIPTION

Figure 1B:
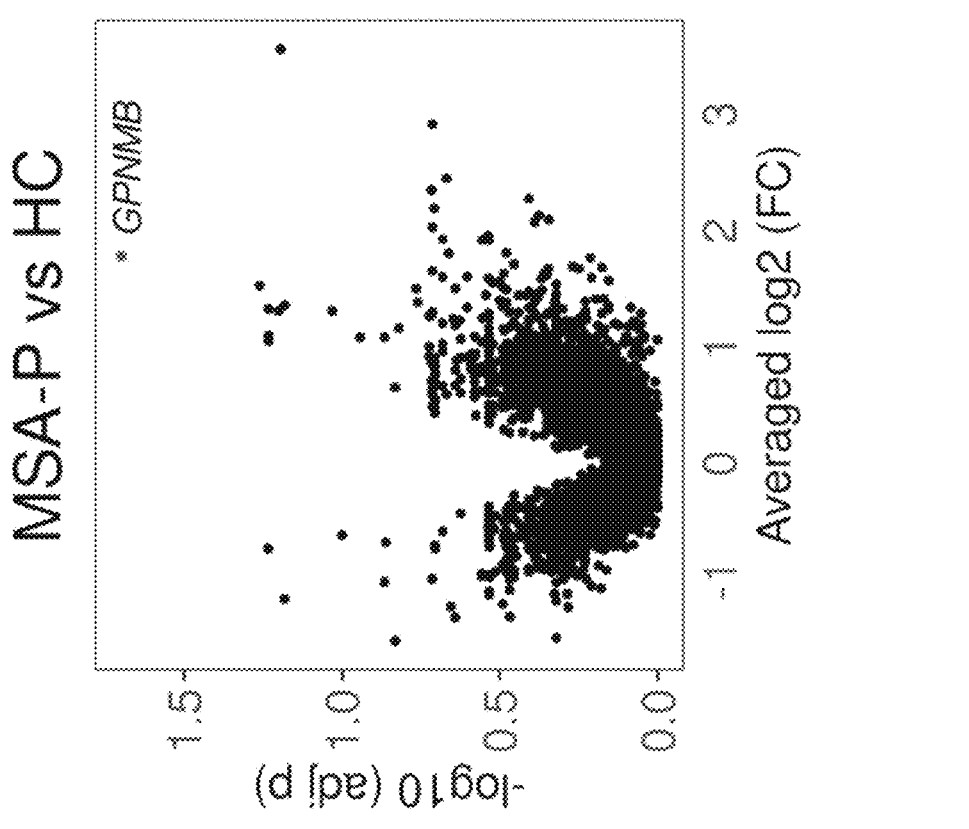
FIGS. 1A-1D illustrate volcano plots representing the differential expression results after p-value combination (excluding LCM dataset). Upregulated genes are greater than zero and downregulated genes are less than zero for log 2 (FC), respectively. The top 5 genes symbols ranked by p-values are shown.

Multiple system atrophy (MSA) is a rare adult-onset neurodegenerative disease of unknown cause, with no effective therapeutic options, and no cure. Limited work to date has attempted to characterize the transcriptional changes associated with the disease, which presents as either predominating parkinsonian (MSA-P) or cerebellar (MSA-C) symptoms. We report here the results of RNA expression profiling of cerebellar white matter (CWM) tissue from two independent cohorts of MSA patients (n=66) and healthy controls (HC; n=66). RNA samples from bulk brain tissue and from oligodendrocytes obtained by laser capture microdissection (LCM) were sequenced. Differentially expressed genes (DEGs) were obtained and were examined before and after stratifying by MSA clinical sub-type.

We detected the highest number of DEGs in the MSA-C group (n=747) while only one gene was noted in MSA-P, highlighting the larger dysregulation of the transcriptome in the MSA-C CWM. Results from both bulk tissue and LCM analysis showed a downregulation of oligodendrocyte genes and an enrichment for myelination processes with a key role noted for the QKI gene. Additionally, we observed a significant upregulation of neuron-specific gene expression in MSA-C and enrichment for synaptic processes. A third cluster of genes was associated with the upregulation of astrocyte and endothelial genes, two cell types with a key role in inflammation processes. Finally, network analysis in MSA-C showed enrichment for β-amyloid related functional classes, including the known Alzheimer's disease (AD) genes, APP and PSEN1.

This is the largest RNA profiling study ever conducted on post-mortem brain tissue from MSA patients. We were able to define specific gene expression signatures for MSA-C highlighting the different stages of the complex neurodegenerative cascade of the disease that included alterations in several cell-specific transcriptional programs. Finally, several results suggest a common transcriptional dysregulation between MSA and AD-related genes despite the clinical and neuropathological distinctions between the two diseases.

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

As used herein, "biological sample" refers to any bodily fluid or tissue obtained from a patient or subject. A biological sample can include, but is not limited to, whole blood, red blood cells, plasma, serum, peripheral blood mononuclear cells (PBMCs), urine, saliva, tears, buccal swabs, CSF, CNS microdialysate, and nerve tissue. In one embodiment, the biological sample is CSF, serum or plasma. In certain embodiments, the biological sample is CSF.

As used herein, "synucleinopathies" refer to neurodegenerative diseases characterized by the abnormal accumulation of aggregates of alpha-synuclein protein in neurons, nerve fibers or glial cells. There are three main types of synucleinopathy: Parkinson's disease (PD), dementia with Lewy bodies (DLB), and multiple system atrophy (MSA).

In the present disclosure, the term "normal control expression level" is to be understood as a predefined value or range of values (reference interval) of a given molecular marker or a combination of the given molecular markers, which is derived from the levels of said molecular marker or markers in a sample or group of samples. If the level of expression is determined at the protein level, then the "normal control expression level" is a predefined value of protein quantity, whereas if the level of expression is determined at the mRNA level, then the "normal control expression level" is a predefined value of mRNA quantity. The samples are taken from a subject or group of subjects wherein the presence, absence, stage, histological subtype or grade, or course of the disease has been properly performed previously. This "normal control expression level" is also useful for determining whether the subject has to initiate a medical regimen and how effective the regimen is. The subject or subjects from whom the "normal control expression level" is derived includes subject(s) wherein the condition is absent. The skilled person in the art, making use of the general knowledge, is able to choose the subject or group of subjects more adequate for obtaining the "normal control expression level" for each of the methods of the present invention. Methods for obtaining the "normal control expression level" from the group of subjects selected are well-known in the state of the art (Burtis C. A. et al., 2008, Chapter 14, section "Statistical Treatment of Reference Values"). In a particular case, "normal control expression level" is a cut-off value defined by means of a conventional ROC analysis (Receiver Operating Characteristic analysis). As the skilled person will appreciate, optimal cut-off values will be defined according to the particular applications of the diagnostic or prognostic method: purpose, target population for the diagnosis or prognosis, balance between specificity and sensibility, etc.

In this disclosure, RNA sequencing was used to characterize the cerebellar white matter transcriptome from neuropathologically verified MSA cases and controls using two independent sample sets and two different profiling technologies. Two different cohorts were used that were each assessed by different gene expression analysis chemistries that we propose increases the robustness of DEG and co-expression network detection.

The main findings of this study are the multiple evidence of oligodendrocyte gene downregulation associated with the loss of myelination. We detected the QKI gene as a master regulator of this associated gene network. Additionally, we showed an upregulation of neuronal-specific gene expression possibly as a consequence of the initial accumulation of monomeric α-synuclein in neurons, with TIAM1 and SYNGAP1 as top hubs in the two networks. An additional coexpression network highlighted the later stages of the neurodegenerative cascade with activation of microglia and astrocytes. Finally, our results suggest a common transcriptional background between MSA and AD, potentially through APP-mediated mechanisms.

Generally, some embodiments of the present invention can be used to develop treatments for disease. Among the various aspects of the present invention is the provision of one or more compositions for treating the neurodegenerative disease multiple-system atrophy (MSA). In one example, the present invention can be used to develop treatments based on the targets identified for MSA.

A target or a marker may be represented by the sequence of one or more strands of a nucleic acid from which it may be derived. Specifically in this invention, a target may be represented by a nucleic acid sequence. Alternatively, a target may be the protein or peptide or the fragments thereof encoded by the nucleic acid sequence. Examples of such nucleic acids include both single stranded and double stranded nucleic acid sequences including miRNA, tRNA, siRNA, mRNA, cDNA, or genomic DNA sequences including complimentary sequences. The concept of a marker is not limited to the products of the exact nucleic acid sequence or protein sequence by which it may be represented. Rather, a marker encompasses all molecules that may be detected by a method of assessing the expression of the marker. Examples of molecules encompassed by a marker include point mutations, silent mutations, deletions, frameshift mutations, translocations, alternative splicing derivatives, differentially methylated sequences, differentially modified protein sequences, truncations, soluble forms of cell membrane associated markers, and any other variation that results in a product that may be identified as the marker. A marker may also be called a target and the terms are used interchangeably.

In one embodiment, the term "target" encompasses a gene or a gene allele thereof, whose expression or activity is directly or indirectly associated with a particular phenotype or cellular condition, or physiological characteristic. The presence or absence of an allele may be detected through the use of any process known in the art, including using primers and probes designed according to a specific allele for PCR, sequencing, hybridization, immunohistochemical analyses.

As used herein, the term "sample" is used in its broadest sense and can be obtained from any source. A sample may refer to a bodily sample obtained from a subject (e.g., a human). A "sample" may be any cell source from which DNA, including genomic, somatic, and germline DNA, RNA (i.e., any form of RNA), and/or protein may be obtained. A sample can include a "clinical sample", i.e., a sample derived from a subject. Samples may include, but are not limited to, peripheral bodily fluids, which may or may not contain cells, e.g., blood, urine, plasma, and serum. Samples may include, but are not limited to, archival samples with known diagnosis, treatment and/or outcome history. Samples may include, but are not limited to, tissue or fine needle biopsy samples, and/or sections of tissues, such as frozen sections taken for histological purposes. For example, in some forms of cancer, a sample may be obtained from the local site of the tumor and may include tissue adjacent to the tumor. Thus, a sample may contain both tumor and non-tumor cells. The term "sample" may also encompass any material derived by processing the sample. Derived materials can include, but are not limited to, cells (or their progeny) isolated from the biological sample and proteins extracted from the sample. Processing of the biological sample may involve one or more of, filtration, distillation, extraction, concentration, fixation, inactivation of interfering components, addition of reagents, and the like.

As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient or subject is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions.

As used herein, the terms "administration" and "administering" of an agent to a subject include any route of introducing or delivering the agent to a subject to perform its intended function. Administration can be carried out by any suitable route, including intravenously, intramuscularly, intraperitoneally, or subcutaneously. Administration includes self-administration and the administration by another.

The term "effective amount" or "therapeutically effective amount" refers to that amount of an agent or combination of agents as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells. The specific dose will vary depending on the particular agents chosen, the dosing regimen to be followed, whether the agent is administered in combination with other agents, timing of administration, the tissue to which it is administered, and the physical delivery system in which the compound is carried.

The terms "treatment," "treating," "treat," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

Some embodiments of the invention may comprise the administration of one or more pharmaceutical compositions to the subject that has been previously diagnosed with a neurodegenerative disease, such as MSA. For example, in some embodiments, the subject has been previously diagnosed with MSA by one skilled in the art (e.g., a physician) such that a therapeutic treatment is warranted by the diagnosis.

In some aspects, the disclosed methods comprise administering an RXR agonist to a subject. In one aspect, the RXR agonist is a stilbene rexinoid. In another aspect, the RXR agonist is a PPAR/RXR heterodimer-selective agonist. In another aspect, the RXR agonist is a natural product selected from the group consisting of valerenic acid, dehydroabietic acid, isopimaric acid, and mimetics thereof.

The RXR agonist can be a retinoid, a rexinoid, a diarylamine, or an indenoisoquinoline. In one aspect, the RXR agonist is a retinoid selected from the group consisting of 9-cis-retinoic acid (9cRA), all trans-retinoic acid (ATRA), retinol, retinal, acyclic retinoid, and 13-cis-retinoic acid. In another aspect, the RXR agonist is a rexinoid selected from the group consisting of bexarotene (also known as LGD1069), LG100268, LG100754, LG101506, LG101305, LG100364, MX-6054, BMS749, AGN194204, UAB 8, 9cUAB30, 4-methyl-UAB30, 5-methyl-UAB30, 6-methyl-UAB30, 7-methyl-UAB30, PA024, HX531, and HX630. In another aspect, the RXR agonist is the indenoisoquinoline AM6-36. Additional RXR agonists are identified in Rodrigues de Almeida et al., Med Res Rev. 2019 July; 39(4): 1372-1397; and Yamada et al., Expert Opin Ther Pat. 2014 April; 24(4):443-52.

In other aspects, the disclosed methods comprise administering a PPARβ agonist to a subject. In certain aspects, PPARβ agonist is a PPARβ/δ agonist, PPARα/(β/δ) agonist, PPAR(β/δ)/γ agonist, or pan-PPAR agonist. In one aspect, the PPARβ agonist is a PPARβ/δ agonist selected from the group consisting of 95EEAI, GW0742 (also known as GW610742), L165041, picrasidine N, MBX8025, KD3010, retinoic acid, and GW501516. In another aspect, the PPARβ agonist is a PPARα(β/δ) agonist selected from the group consisting of γ-mangostin, ertiprotafib, and elafibranor (also known as GFT505). In another aspect, the PPARβ agonist is a PPAR(β/δ)/γ agonist (e.g., punicic acid). In another aspect, the PPARβ agonist is a pan-PPAR agonist selected from the group consisting of bavachinin, CNX-013-B2, GW4148, GW9135, isoflavone, Lyso-7, LY465608, PLX134, ZBH201102, DRL11605, GW625019, IV A337, indeglitazar (also known as PLX204 and PPM204), netoglitazone/isaglitazone (also known as PGX510 and MC555), sipoglitazar, sodelglitazar (also known as GW677954), tetradecylthio-acetic acid (TTA), chiglitazar, bezafibrate, and telmisartan.

In some aspects, the PPARβ agonist is selected from the group consisting of ertiprotafib, GW0742 (also known as GW610742), retinoic acid, and KD3010. In other aspects, the PPARβ agonist is selected from the group consisting of 95EEAI, GW0742 (also known as GW610742), L165041, picrasidine N, MBX8025, KD3010, retinoic acid, GW501516, γ-mangostin, ertiprotafib, elafibranor (also known as GFT505), punicic acid, bavachinin, CNX-013-B2, GW4148, GW9135, isoflavone, Lyso-7, LY465608, PLX134, ZBH201102, DRL11605, GW625019, IV A337, indeglitazar (also known as PLX204 and PPM204), netoglitazone/isaglitazone (also known as PGX510 and MC555), sipoglitazar, sodelglitazar (also known as GW677954), tetradecylthio-acetic acid (TTA), chiglitazar, bezafibrate, and telmisartan. Additional PPARβ agonists that can be used in the methods disclosed herein are outlined in Tan, C. K., et al. (2017). Expert Opinion on Therapeutic Targets, 21(3), 333-348.

The following examples are given for illustrative and non-limiting purposes of the present invention.

Examples

This invention identifies one or more targets or markers, or combination thereof, for diagnosing the neurological disease multiple-system atrophy (MSA). This invention further identifies one or more composition, or combination thereof, for treating MSA.

Material and Methods

Human Samples

We analyzed two independent cohorts of postmortem brains (cerebellum white matter). The cohort 1 (C1) was obtained from both the New South Wales (NSW) Brain Banks (Sydney, AU; n=20) and from the Brain and Body Donation Program (BBDP) (Sun City, AZ; n=18), including 19 MSA pathologically proven cases and 19 Healthy Controls (HC). Specimens were obtained from deep cerebellar white matter lateral to the dentate nucleus (BBDP). The number of samples for each brain bank was matched between MSA and HC (NSW=10; BBDP=9 in each group). All the sample characteristics and the comparison between groups are reported in Table 1A. The samples were matched for age (10 males and 9 females in each group), and there were not significant differences for postmortem interval PMI (t=−0.311; p=0.757) and age (W=175, p=0.884). Among the patients, five were clinically diagnosed as MSA-P and other five were clinically diagnosed as MSA-C. The remaining patients were not attributed to a specific clinical subtype. The MSA-P and MSA-C subgroups compared with HC did not show any significant difference in age, sex and PMI distribution. The C2 was obtained from the Queen Square Brain Bank for Neurological Disorders, (London, UK), including 48 patients and 47 HC. Specimens were obtained from the cerebellar hemisphere. All the sample characteristics and the comparisons between groups are reported in Table 1B. There was not significant difference in the gender distribution (p=0.402) and PMI (W=1172; p=0.746), but the age in HC was significantly higher than in MSA cases (W=159.5; p=5.6E-13). Among the patients, 37 were MSA-P, whereas the remaining (n=11) were clinically diagnosed as MSA-C. The clinical subgroups compared with HC showed a significant difference for age, but not for PMI and gender distributions. The same patients from C2 were classified by neuropathological examination for: striato-nigral degeneration (SND; n=16), olivo ponto-cerebellar atrophy (OPCA; n=15) and mixed (SND/OPCA; n=17). Finally, a subsample of the C1 was selected to conduct Laser Capture Microdissection (LCM) on Oligodendrocytes (6 MSA and 6 HC). There were not significant differences in age (t=−0.469; p=0.650), PMI (W=26.5; p=0.199) or biological sex (p=0.547). Three MSA cases were clinically diagnosed as MSA-C, one as MSA-P, and the remaining could not be diagnosed to the subtypes MSA-P or MSA-C (Table 1C).

Table 1A, Table 1B, and Table 1C show sample characteristics of the different cohorts analyzed. Differences in age and PMI between cases and controls were assessed using t-test or Wilcoxon test, according to the data distribution. Sex distribution was assessed using the Fisher's Exact test.

TABLE 1A

| A (Cohort 1) | | MSA (n = 19) | HC (n = 19) | P |
|---|---|---|---|---|
| | Age | 70.2 ± 7.4 | 69.6 ± 6.5 | t = −0.311; p = 0.757 |
| | PMI | 10.6 ± 10.1 | 12.0 ± 10.8 | W = 175, p = 0.884 |
| | Males | 10 | 10 | p = 1.000 |
| | Females | 9 | 9 | |
| | | MSA-P (n = 5) | HC (n = 19) | P |
| | Age | 66.8 ± 5.8 | 69.6 ± 6.5 | t = −1.168; p = 0.255 |
| | PMI | 15.2 ± 5.9 | 12.0 ± 10.8 | W = 60.5; p = 0.374 |
| | Males | 3 (60.0) | 10 (52.6) | p = 1.000 |

US 12,571,046 B2

13

TABLE 1A-continued

| | | | |
|---|---|---|---|
| Females | 2 (40.0) | 9 (47.4) | |

| | MSA-C (n = 5) | HC (n = 19) | P |
|---|---|---|---|
| Age | 72.2 ± 6.6 | 69.6 ± 6.5 | t = 0.366; p = 0.718 |
| PMI | 19.4 ± 13.2 | 12.0 ± 10.8 | W = 66.5; p = 0.188 |
| Males | 4 (80.0) | 10 (52.6) | p = 0.356 |
| Females | 1 (20.0) | 9 (47.4) | |

TABLE 1B

| B (Cohort 2)* | MSA (48) | HC (47) | P |
|---|---|---|---|
| Age | 64.5 ± 8.0 | 84.2 ± 9.1 | W = 159.5; p = 5.6E-13 |
| PMI | 61.7 ± 24.0 | 59.9 ± 28.2 | W = 1172; p = 0.746 |
| Males (%) | 21 (43.8) | 16 (34.0) | p = 0.402 |
| Females (%) | 27 (56.3) | 31 (66.0) | |

| | MSA_P (37) | HC (47) | P |
|---|---|---|---|
| Age | 64.8 ± 8.5 | 84.2 ± 9.1 | W = 129.5; p = 2.6E-11 |
| PMI | 63.2 ± 24.6 | 59.9 ± 28.2 | W = 930; p = 0.589 |
| Males (%) | 14 (37.8) | 16 (34.0) | 0.820 |
| Females (%) | 23 (62.1) | 31 (66.0) | |

| | MSA_C (11) | HC (47) | P |
|---|---|---|---|
| Age | 63.5 ± 6.4 | 84.2 ± 9.1 | W = 30; p = 6.0E-06 |
| PMI | 56.9 ± 22.2 | 59.9 ± 28.2 | W = 242; p = 0.751 |
| Males (%) | 7 (63.6) | 16 (34.0) | 0.093 |
| Females (%) | 4 (36.4) | 31 (66.0) | |

In Table 1B, One MSA-P sample was removed after the PCA analysis (Final sample size: MSA=47; MSA-P=36; MSA-C=11; HC=47).

TABLE 1C

| C (Cohort 1 - LCM)** | MSA (n = 6) | HC (n = 6) | P |
|---|---|---|---|
| Age | 70.0 ± 7.7 | 72.0 ± 7.0 | t = −0.469; p = 0.650 |
| PMI | 16.3 ± 14.4 | 9.4 ± 11.0 | W = 26.5; p = 0.199 |
| Males | 4 | 2 | p = 0.547 |
| Females | 2 | 4 | |

In Table 1C, Two MSA and one HC samples were removed after PCA analysis (Final sample size: MSA=4; HC=5).

RNA Extraction and RNA Sequencing

For the C1, total RNA was extracted using the Qiagen miRNAeasy kit (#217004), and DNAse-treated (Qiagen). Quality was assessed by Bioanalyzer (Agilent). Sequencing libraries were prepared with 250 ng of total RNA using Truseq RNA Sample Preparation Kit v2 (Illumina, Inc) following the manufacturer's protocol. In brief, poly-A containing mRNA molecules were purified using poly-T oligo attached magnetic beads. The mRNA was then thermally fragmented and converted to double-stranded cDNA. The cDNA fragments were end-repaired, a single "A" nucleotide was incorporated, sequencing adapters were ligated, and fragments were enriched with 15 cycles of PCR. Final PCR-enriched fragments were validated on a 2200 TapeStation (Agilent Technologies) and quantitated via qPCR using Kapa's Library Quantification Kit (Kapa Biosystems) on the QuantStudio 6 Flex Instrument (ThermoFisher). The final library was sequenced by 50 bp paired-end sequencing on a HiSeq 2500.

For the C2, total DNAse-treated RNA was extracted in TRI Reagent (Zymo, #R2050) from ~ 5 mg of tissue using Rino Tubes (Next Advance, #13503) with one 0.1 mL scoop of Stainless Steel Beads 0.9-2.0 mm blend RNase Free (Next Advance, #SSB14B), Bullet Blender Gold (Next Advance, model BB24-AU), and Zymo Direct-zol-96 RNA (#R2054) utilizing the kit's DNase I digestion step. Extracted RNA was then assayed on an Agilent TapeStation 4200 and Agilent RNA ScreenTape (#5067-5576). The mean RNA integrity number equivalent (RINe) and concentration for MSA cases were 3.42 and 77.6 ng/µl, and Control cases were 3.59 and 64.76 ng/µl, respectively. Following TempO-Seq Assay User Guide (version 2.0), 1 µl of the extracted RNA from each of the 96 samples processes separately into the TempO-Seq Human Whole Transcriptome Assay (Bio-Sypder, index set C, #200615). This assay is based on a proprietary 3' mRNA capture protocol, using probes for protein-coding mRNA. Thus, extracted RNA was not rRNA depleted or poly(A)-selected. A total of sixteen cycles of PCR, on a QuantStudio 6 Flex Instrument (ThermoFisher), were used to amplify the 96 ligated samples. The 96 samples were pooled into one library and then purified using Nucleo-Spin Gel and PCR clean-up kit (Macherey-Nagel, #740609). The final library was sequenced according to the TempO-Seq Assay User Guide (version 2.0, 50 bp read1×9 bp index1×9 bp index2) on the NextSeq 500/550 High Output v2 kit (Illumina, 75 cycles, #FC-404-2005) on a NextSeq 500 (Illumina), at a final concentration of 1.6 pM with 2% PhiX. For sequencing, the BioSpyder TempO-Seq Custom Index 1 Sequencing Primer was used at 0.3 µM final concentration diluted in HT1 buffer (illumina, see nextseq-custom-primers-guide-15057456-01). Final library concentration was determined via the mean of three replicates using the Qubit dsDNA BR Assay (Invitrogen, #Q32853) on a Qubit 2 Fluorometer (Invitrogen).

Laser Capture Microdissection (LCM)

Twelve samples (6 MSA, 6 HC) from the C1 were used for Laser Capture Microdissection of Oligodendrocytes in the cerebellar white matter. Fresh frozen brains were sectioned on a cryostat at 10 µm thickness, mounted on PEN membrane glass slides (Applied Biosystems) and stored immediately at −80° C. until use. Before sectioning and between each tissue block, the knife holder and antiroll plate were wiped carefully with 100% ethanol to avoid cross-contamination. Oligodendrocytes were stained by using a modified H&E staining protocol adapted from Ordway et al. [49]. A total of 300 oligodendrocytes per sample were captured using Arcturus CapSure Macro LCM Caps (Applied Biosystems) with the following settings: UV speed at 676 um/s and UV current at 2%. RNA was extracted immediately after cell capture using the Arcturus PicoPure RNA Isolation Kit (Applied Biosystems). RNA quality was tested with the Agilent BioAnalyzer and RIN's averaged at 5.5 after extraction. For library preparation the SMARTer® Stranded Total RNA-Seq Kit—Pico Input (Clontech/Takara) was used, with integrated removal of cDNAs derived from rRNA using probes specific to mammalian rRNA and some mitochondrial RNA. Libraries were validated on a 4200 TapeStation (Agilent Technologies) and quantitated via qPCR using Kapa's Library Quantification Kit (Kapa Biosystems) on the QuantStudio 6 Flex Instrument (ThermoFisher). Samples were sequenced (2×75 bp paired-end run) on the Illumina HiSeq2500.

Data Analysis

Differential expression analysis: The normal distribution of age, and PMI in MSA cases and HC was assessed using the Shapiro-Wilk test. The means between groups were compared using the t-test or Wilcoxon rank-sum test, depending by the data distribution. The distribution of age was compared using the Fisher's Exact test. All these analysis were conducted using the R v3.3.1 software [89].

Raw sequencing data were demultiplexed and converted to FASTQ files using bcl2fastq Conversion Software v2.17 (Illumina, San Diego, CA). Quality controls on FASTQ files were conducted using MultiQC v0.9 software [26]. The reads were aligned to the human reference genome (GRCh37) using the STAR software v2.5 [23] and summarized as gene-level counts using featureCounts v1.4.4 [40]. For both datasets (C1 and C2) PCA analysis was used to assess the presence of outliers and to detect any batch effects. Outliers and batch effects detection were conducted through Principal Component Analysis (PCA), using R software v3.3.1 [89], and quality reports were generated using FastQC v0.11. and Qualimap v2.1.3 [88]. Four samples were deemed to be outliers and were removed (detailed below in Results).

Gene expression differential analyses between MSA cases and controls were conducted using the R package DESeq2 v1.14.1[43], including age, gender, PMI as covariates in all the comparison (except for gender in the C1 differential analysis including all samples because completely matched). The sample origin (Brain Bank) was included as covariate in the C1 analysis (including the LCM data), with the exception of the total sample analyzed because the samples were matched between cases and controls. The method implemented in DESeq2 fits a generalized linear model (GLM) for each gene, modeling reads counts following a negative binomial distribution. The Logarithmic Fold Change (FC), expressed as Log 2 Fold Change, is estimated with an Empirical Bayes procedure, whereas the significance is assessed with a Wald Test [43]. The p-values were corrected for multiple testing using the False Discovery Rate (FDR) method [84], considering as significant all the genes with adjusted p-value (adj p)<0.05.

P-value combination: The results from the two cohorts were combined using a meta-analysis approach based on the weighted-Z method [77] as implemented in the R-package survcomp [61]. The input consisted of the p-values obtained from the differential expression analysis. Since the Z-Weighted test assumes 1-tailed p-values, we converted the 2-tailed nominal p-value to 1-tailed p-value using the following formula when the Log 2 Fold Change was >0: $p_{1 Tailed}=p_{2-Tailed}/2$. Otherwise, we used the following formula: $p_{1 Tailed}=1-(_{P2Tailed/2})$. The uncorrected p-values were weighted using the sample sizes of the two datasets, and combined using the combine.test function with the "log it" option included in the R-package survcomp [20]. Finally, the combined 1-tailed p-values were converted in 2-tailed p-values and adjusted for multiple testing with the FDR method.

Cell Specific Expression

We classified the genes detected in the differential expression analysis using an external database of expression values from different types of cells isolated from mouse cerebral cortex [78]. We computed an enrichment score for each cell type and gene, assigning each gene to a specific cell type according to the relative expression in the other cell types. The method used to generate the enrichment score was described in our previous study, and was used to classify RNA profiling data from human bulk tissue isolated from 7 different brain regions to identify cell specific functional processes in Alzheimer's Disease [54]. The enrichment of cell specific genes was investigated across DEGs and co-expression modules using a hypergeometric test as implemented in the R function phyper. Results were adjusted with the FDR method.

Enrichment and Functional Network Analysis

Lists of DEGs were analyzed for Gene Ontology (GO) enrichment using the R-package anRichmentMethods, adjusting the p-value with the FDR method. The same gene lists were also analyzed using HumanBase, constructing tissue-specific functional networks [30].

The enrichment of Alzheimer's disease genes in MSA was conducted using the data from the Accelerated Medicine Partnership-Alzheimer's Disease (AMP-AD) portal. We downloaded the differential expression results from 7 different brain regions from the Mayo, Mount Sinai and ROSMAP cohorts [3, 7, 76]. Specifically, the brain regions included were: temporal cortex (TCX), cerebellum (CBE), dorsolateral pre-frontal cortex (DLPFC), inferior frontal gyrus (IFG), frontal pole (FP), parahippocampal gyrus (PHC), and superior temporal gyrus (STG). The DEGs from these 7 brain regions were used as gene set references for the list of MSA-C genes ranked by log 2 FC. The analysis was conducted using R-package fgsea adjusting the p-values with the FDR method.

Weighted Correlation Network Analysis

We conducted Weighted Correlation Network Analysis (WGCNA) in the MSA-C cohorts with the aim of identifying modules of co-expressed genes associated with the disease and enriched for specific biological processes [38]. We computed the co-expression networks using the data from C1 and then we estimated the module preservation in C2, using only MSA-C and HC. The analysis was conducted using the WGCNA R-package [38]. Genes for both C1 and C2 with less than 10 average counts were filtered out due to low expression and data were normalized using the vst function of the DESeq2 package [43]. The matrix of expression values was adjusted for age, sex, source and PMI using the function removeBatchEffect as implemented in the limma R-package [57]. Finally, we filtered out the 50% of genes having lower Median Absolute Deviation (MAD). We generated a signed co-expression network for C1 using the function blockwiseModules, with the option mergeCutHeight=0.25. Then, we computed the module eigengenes and we investigated their relationship with disease status using a linear model as implemented in the limma package. We calculated the module membership and gene-trait significance (MSA-C disease status) with the goal of ranking genes in each co-expression modules. Modules associated with disease status were further investigated using GO enrichment analysis. The enrichment for genes expressed in specific cell types was conducted using as reference gene sets the gene specifically expressed in the 5 cell types from Zhang et al. [78] (see previous section "Cell specific Expression") and as a test set all of the genes ranked by module memberships for the module associated with disease status. Finally, we checked the module preservation in C2 using the modulePreservation function with 1,000 permutations. Relevant coexpression networks were exported and visualized using Cytoscape v3.7.2 [62]. Results from relevant modules were compared with published data from Darbelli et al. [19], intersecting the lists of genes and conducting an enrichment analysis using the R-package fgsea.

Results

Quality Controls

For C1 (Illumina), we sequenced a total of 470 Million (M) reads (average: 12.4 M; range: 3.8-32.6 M) with a 76.7% average mapping rate. PCA analysis did not show the presence of outliers. For C2 (TempO-Seq) we sequenced a total of 162 M reads (average: 1.7 M; range: 0.1-3.8 M), with a 90.2% average mapping rate. PCA analysis showed the presence of one outlier in the C2 group and it was removed from all subsequent analyses. The final sample size was: MSA=47 and HC=47. For the LCM sample (a sub-sample from C1) we sequenced a total of 353 M reads (average: 29.4 M; range: 23.4-33.3 M) with an average 64.4% mapping rate. We detected the presence of three outliers that were also removed. The final sample size used for the differential analysis from the LCM dataset was: MSA=4 and HC=5.

Differential expression results: bulk tissue human samples (MSA, MSA-P and MSA-C vs HC)

Differentially expressed genes (DEGs) were obtained by combining the results from both cohorts using a meta-analysis approach. Details about the specific results for each cohort are reported in FIGS. 12A, 12B, and 13. The comparisons of the log 2 FC obtained in the differential analyses for the two independent cohorts for MSA, MSA-P and MSA-C were statistically significant ($\rho$ range=0.204-0.456; $p<2.2E-16$). The largest correlation coefficient ($\rho=0.456$) was obtained for the MSA-C subtype probably due to the larger significance and effect size of the genes detected.

Figure 1A:
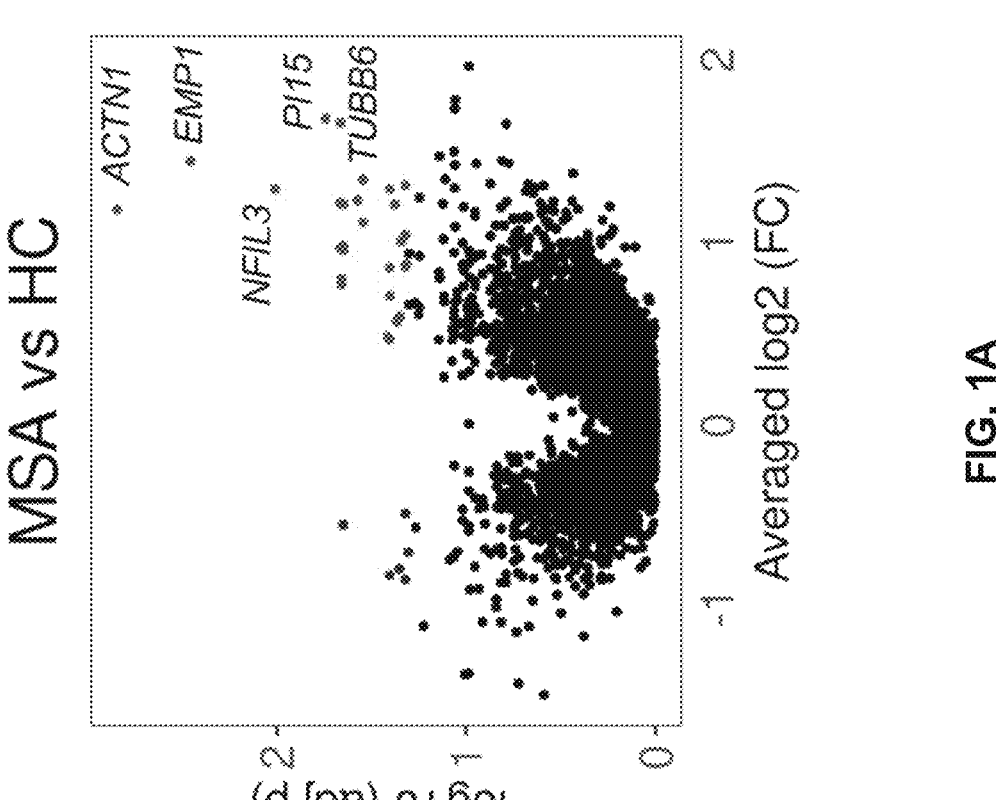
Figure 1D:
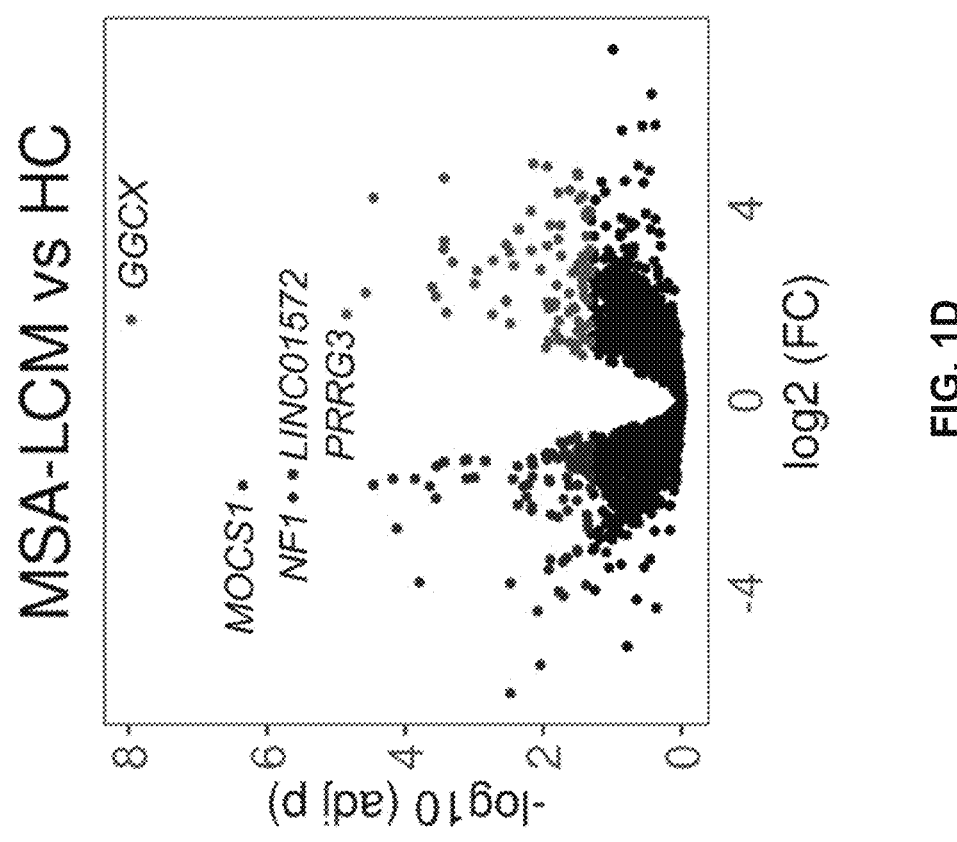
Figure 1C:
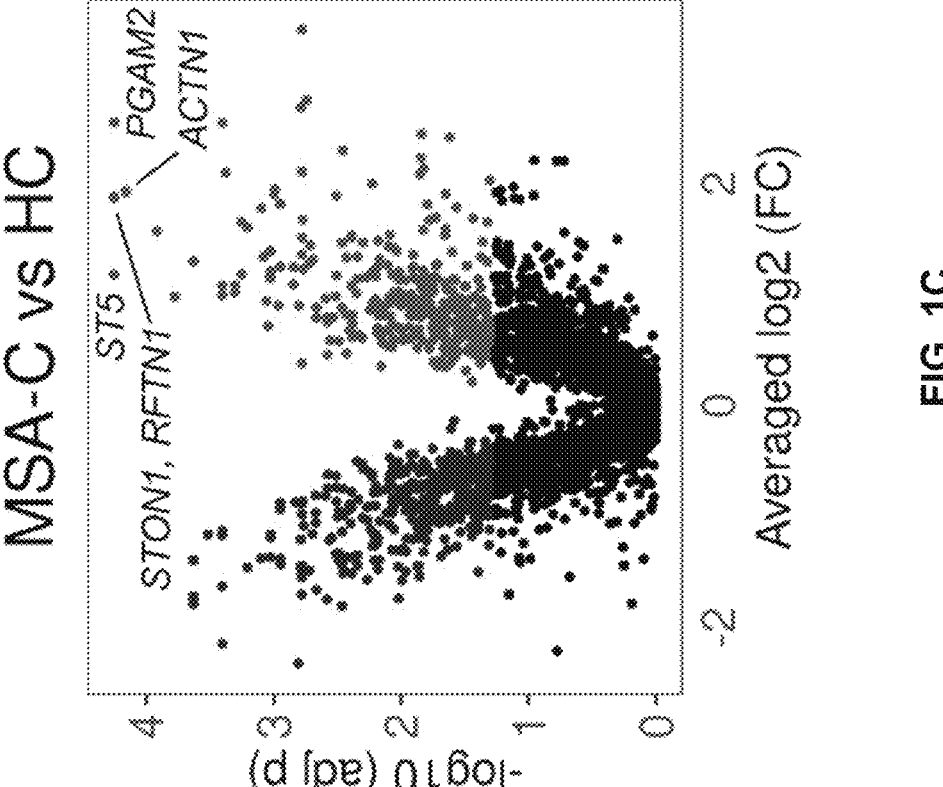
Figure 2B:
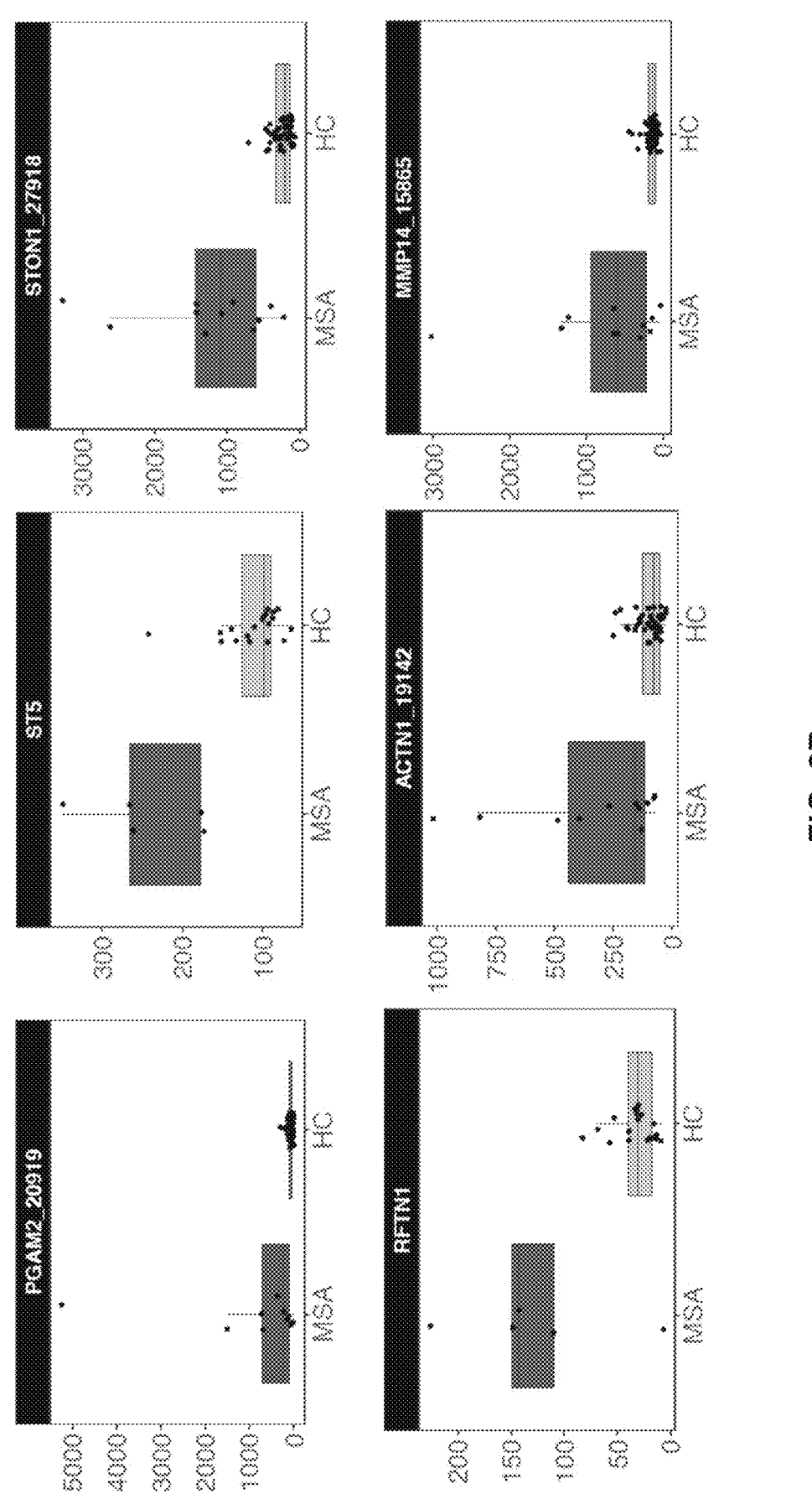

After p-value combination, we obtained a set of DEGs ranging from 1 (MSA-P) to 747 (MSA-C) depending on the MSA clinical sub-type (FIGS. 1A-1C). The top 3 DEGs for MSA in general were ACTN1, EMP1 and NFIL3 (adj $p<0.01$; all upregulated). In the MSA-P clinical sub-type we detected only one DEG (GPNMB), whereas in MSA-C the top genes were: PGAM2, ST5, STON1, RFTN1, ACTN1 and MMP14 (adj $p<1.0E-04$; all upregulated) (FIG. 9; FIG. 2). We explored the differential expression between SND vs HC, and OPCA vs HC, detecting a total of 7 and 58 genes, respectively. MLPH, detected in SND, was also detected when analyzing the clinical subtype MSA-P in C2, whereas a total of 47 genes detected in OPCA were also observed in the MSA-C clinical subtype in C2. Correlation of the log 2 FC between the differential analysis for clinical and neuropathological classification criteria were $\rho=0.622$ (MSA-P/SND) and $\rho=0.830$ (MSA-C/OPCA) (both $p<2.2E-16$).

Figure 3:
FIG. 3 illustrates results of the functional network analysis on MSA-C DEGs. Module 1 was enriched for amyloid-β metabolism (q=5.3E-05) including key AD genes as: APP, PSEN1, CLU, ROCK2 and DYRK1.
Figure 4:
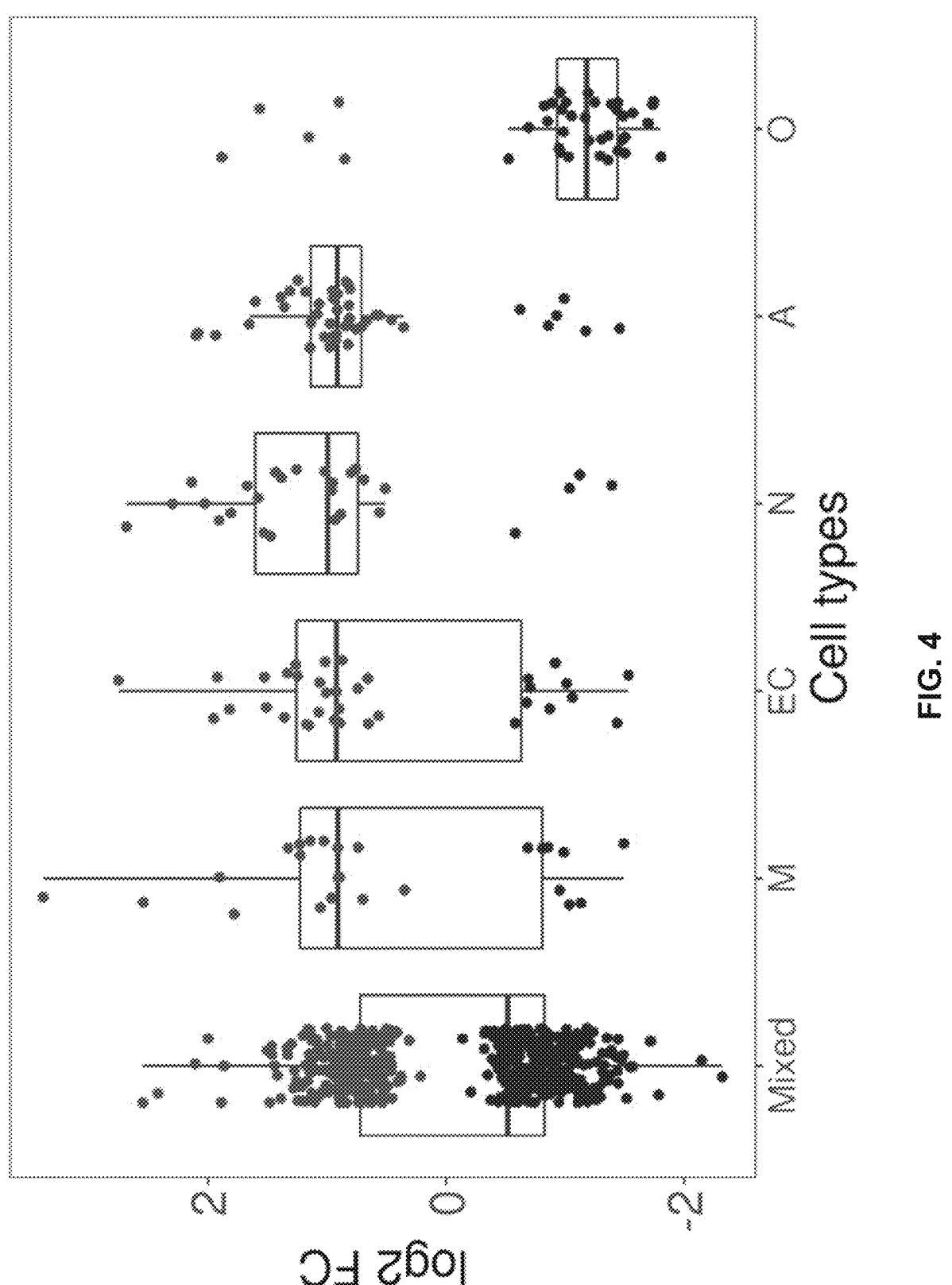
FIG. 4 illustrates DEGs Log 2 FC distribution across the cell-specific genes classes; upregulated genes are greater than zero and downregulated genes are less than zero for log 2 (FC) in MSA-C, respectively.

We explored the functional significance of the DEGs by applying a functional network analysis specific for the cerebellum and a GO enrichment analysis. Using the 35 MSA DEGs we detected a small network with 2 modules enriched for "cell-cell adhesion" (SELL and BCL6 genes) and "angiogenesis" (COL4A1 and COL4A2 genes) (both $q<0.01$). The GO analysis yielded significant enrichment of the Biological Process "collagen-activated signaling pathway" (adj $p=0.030$; genes: COL4A1, COL4A2, ITGA11). Using all of the 747 MSA-C DEGs we detected a large network including 9 different modules (FIG. 3). We observed the highest enrichment significance in module 1 (M1) which was amyloid-$\beta$ metabolism (top GO process: $q=5.3E-05$), including the Alzheimer's disease (AD) relevant genes: APP, PSEN1, CLU, ROCK2 and DYRK1. The central role of APP was confirmed by a separate protein-protein interaction analysis showing this gene as the most important hub in a network that included 30% of the DEGs generated using WEBGESTALT [75]. The second highest significance was reached in module 2 (M2) for respiratory chain complex assembly (top GO process: $q=8.2E-03$)

(FIGS. 10A and 10B). With the GO analysis we detected 625 significant functional classes, mostly related to cellular and cytoplasmic components, neuro and gliogenesis.

Differential Expression Analysis: Bulk Tissue Human Samples (MSA-C Vs MSA-P, OPCA vs SND)

We ran the comparison MSA-C vs MSA-P in C1 and C2, obtaining 1 DEG in C1. After p-value combination we did not detect any remaining significant genes after multiple test correction. The top 10 genes ranked by p-value are reported in FIG. 14. Finally, in the comparison of OPCA vs SND in C2 we obtained 156 DEGs. The gene detected in MSA-C vs MSA-P (PDZRN4) was not detected in the OPCA vs SND analysis. The GO enrichment for these DEGs showed top processes being "nervous system development" and "neurogenesis".

Enrichment of AD Genes in MSA-C

After we observed the presence of the AD-related process (amyloid-$\beta$ metabolism) and AD-related genes in MSA-C, we tested the enrichment of AD genes in MSA-C. We used data from AMP-AD, running an enrichment analysis by brain region using as reference sets the DEGs from each brain region. The results showed a significant enrichment of TCX (adj $p=7.4E-05$) and PHG (adj $p=2.0E-02$) AD DEGs among upregulated MSA-C genes which were also confirmed when we used more conservative cutoffs to select AD genes (adj $p<0.01$, $<0.001$, and $<0.0001$). As further validation, we used the less variable genes between AD and non-demented controls (ND) (adj $p>0.950$). As expected, we did not observe any significant enrichment of TCX or PHG AD DEGs genes. We compared the DEGs detected in MSA-C, with the DEGs detected in TCX and PHG, only selecting genes having the same log 2 FC direction, considering the comparison: affected vs non-affected. We detected 243 genes in TCX, 166 in PHG and 126 common between both regions TCX, PHG and MSA-C.

Differential Expression in LCM Oligodendrocytes

We detected a total of 187 differentially expressed genes in oligodendrocytes (90 upregulated and 97 downregulated) (FIG. 1D). The top 4 significant genes (adj $p<1.0E-05$) were: GGCX, MOCS1, NF1 and LINC01572 (FIG. 11). Using functional module discovery analysis, we detected a network including 4 modules (72 genes in total) enriched for telomere maintenance (M1: $q=1.9E-03$; genes: PTGES3 and WRAP53) and ncRNA processing (M2: $q=0.0025$; genes: DIMT1, INTS8, and MTREX). Modules 3 and 4 are weakly enriched for immune processes and cell growth ($q<0.05$). Using the GO analysis in the complete gene list, we detected a significant enrichment in the myelination process mostly due to downregulated genes.

Bioinformatic-Based Cell Specific Expression Profiling

Figure 5:
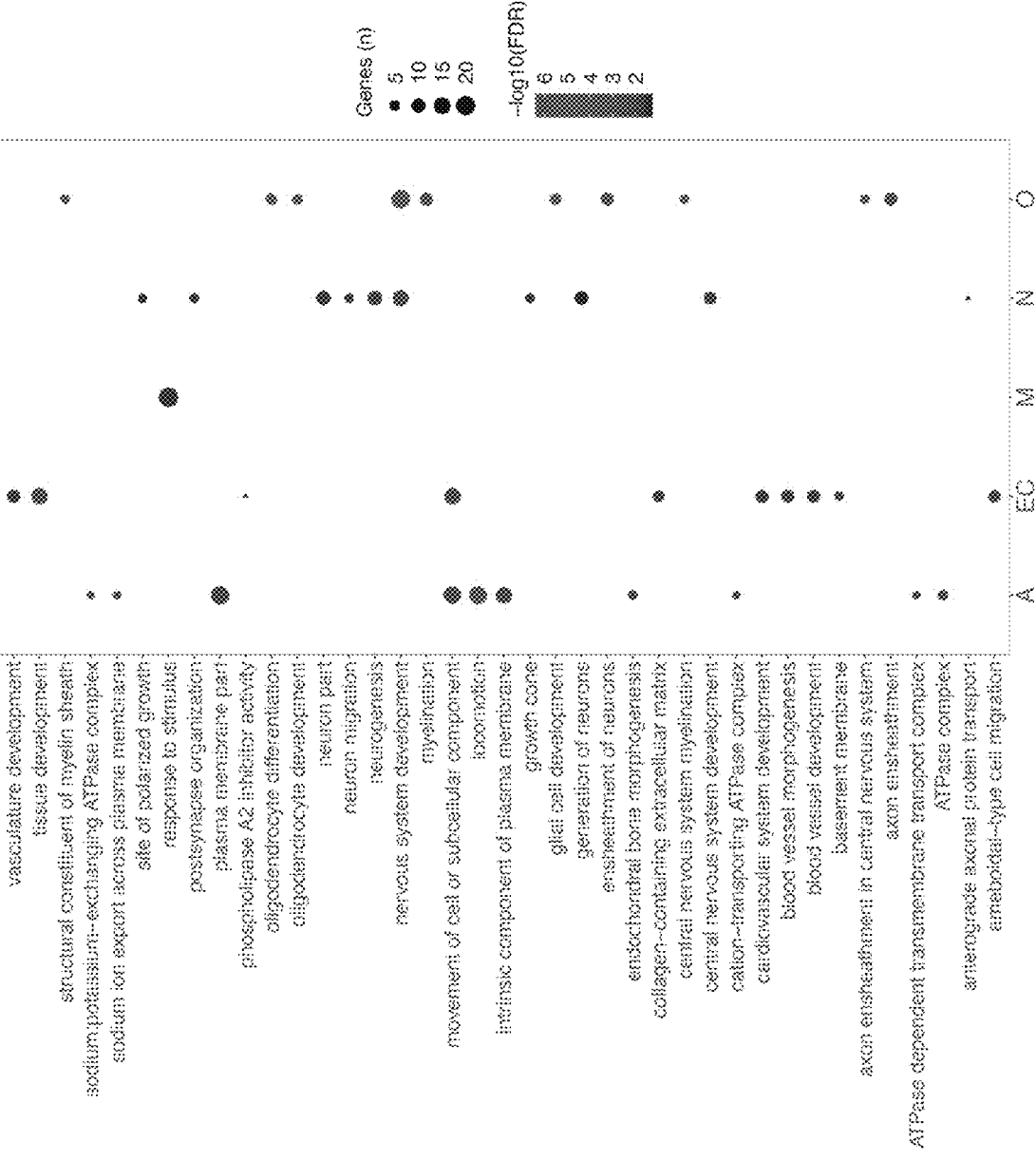
FIG. 5 illustrates dot plot reporting the top 10 GO functional classes enriched in each cell-specific gene class.

We classified the DEGs obtained in the MSA-C group according to their expression in five brain cell types [54, 78]. We selected only the MSA-C results because the large number of DEGs makes it possible to identify robust cell-specific upregulation/downregulation trends. Most of the DEGs were not cell specific ("mixed": 74.7% of the total DEGs), whereas the remaining genes were: astrocyte (6.6%), oligodendrocyte (5.8%), endothelial cell (5.1%), neuron (4.1%) and microglia (3.7%) specific. We found a significant overrepresentation of astrocyte and oligodendrocyte genes (both: adj $p=2.9E-04$). We observed a strong downregulation of oligodendrocyte genes and upregulation of microglia, neuron and astrocyte genes. To investigate if these patterns are disease specific, we compared the log 2 FC of genes differentially expressed (adj $p<0.05$) with those non-differentially expressed (adj $p>0.05$) for each cell type. We observed the highest significance for oligodendrocyte (downregulated in MSA) and neuronal genes (upregulated in MSA) (p<0.001). Similar results were obtained when we relaxed the gene inclusion cutoff to adj p<0.10. We conducted GO enrichment analysis on the cell-specific DEGs. The highest significance was reached for oligodendrocyte genes, enriched for myelination and oligodendrocyte development processes. Astrocytes were enriched for transport of ion across the membrane, plasma membrane components, and ATPase complex (FDR<0.01). Endothelial cell genes were enriched for cell migration and angiogenesis. Neuronal genes were enriched for neurogenesis and post-synapse organization (FIG. 5).

WGCNA Analysis

Figure 6A:
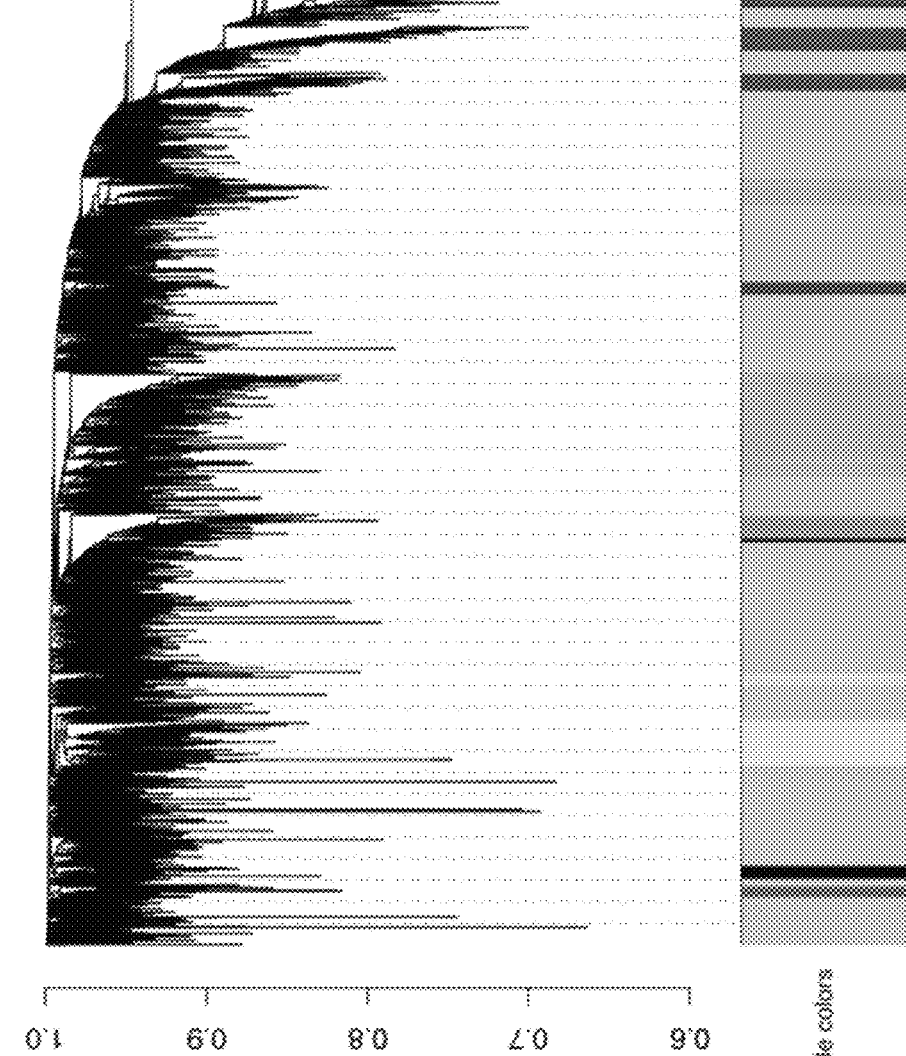
FIGS. 6A and 6B illustrate WGCNA analysis.
Figure 6B:
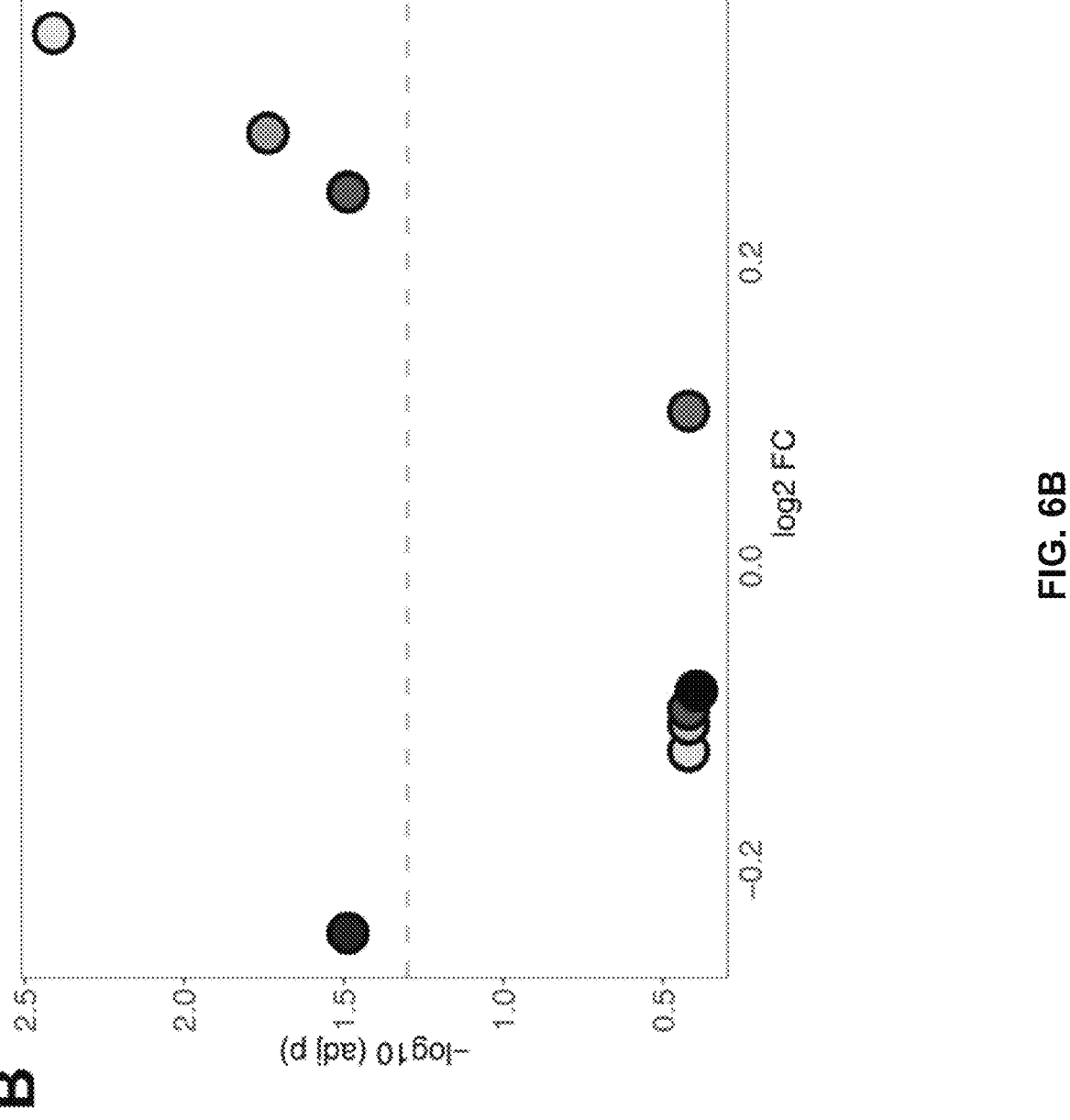
Figures 7A, 7B:
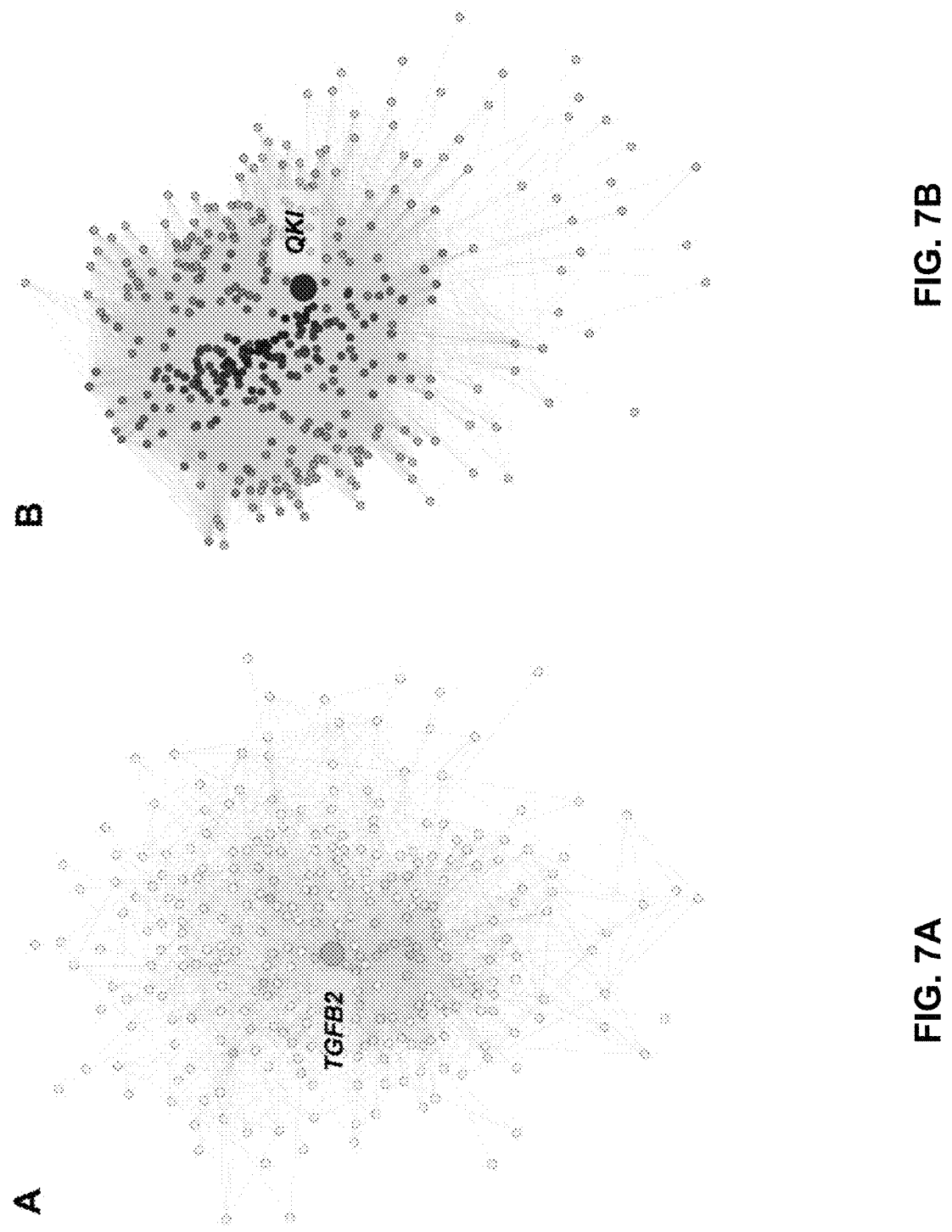
FIGS. 7A-7D illustrate coexpression networks generated from the significant coexpression modules visualized with Cytoscape; the hub genes are the larger nodes; the color intensity of each node is proportional to the number of connections.
Figures 7C, 7D:
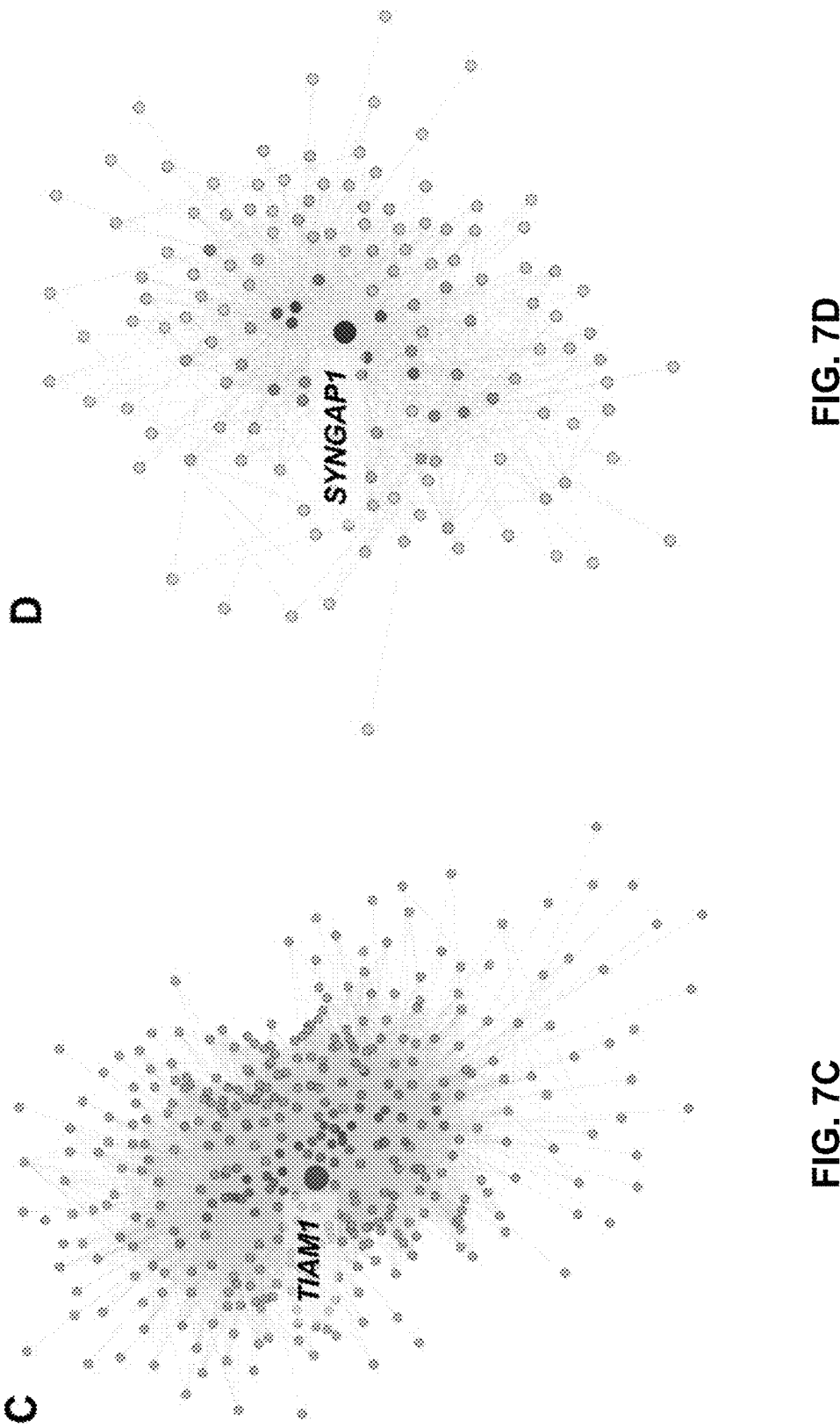

Considering the large number of DEGs for the MSA-C subtype, we further investigated this group using WGCNA analysis. We computed a coexpression network using the data from C1 and validated the results in C2 by means of the module preservation analysis. After gene filtering (see Methods), a network was generated using the 7,650 genes with larger MAD using "9" as threshold power. We obtained nine co-expression modules in total including 2,675 genes (35.0% of the genes), whereas the remaining were not significantly co-expressed and then were included in the grey module (FIG. 6A). The number of the genes in each module ranged from 78 to 917. A total of 4 modules (yellow, green, brown, and blue) were associated with disease status, all showing an increase in MSA-C with the exception of the blue module (FIG. 6B). The number of genes in these 4 modules ranged from 160 to 485. Two of the significant modules were highly correlated with each other. We computed the module membership (correlation of each gene with the module eigengenes), and the gene-trait significance (correlation with disease status). As expected, the gene-trait significance was highly correlated with the log 2 FC (r=0.846; p<2.2E-16). We represented the correlation of the module membership with gene-trait significance in scatterplots. As expected, we detected a significant positive correlation for the 4 modules associated with MSA but not for the others. The genes for these 4 significant modules are ranked by module membership p-value. The most important hubs for the 4 modules were: TGFB2 (yellow; FIG. 7A), SYNGAP1 (green; FIG. 7D), TIAM1 (brown; FIG. 7C) and QKI (blue; FIG. 7B). These networks are represented in FIGS. 7A-7D.

We conducted GO enrichment analysis using the gene modules as input and observed the most significant and specific enrichment in the brown and blue modules. The yellow module (upregulated) showed a heterogeneous enrichment, including immune response but also tissue and organ development and response to stress. The green module (upregulated) was enriched for membrane proteins, ribosome and translation. The brown module (upregulated) was enriched for synaptic functional classes (top class: FDR=1.2E-33), and the blue module (downregulated) was enriched for myelination and oligodendrocyte classes (top class: FDR=3. 1E-09).

We explored the enrichment for specific brain cell types gene expression using the data from Zhang et al. [54, 78]. Accordingly with the GO enrichment we observed, we found a significant enrichment of astrocyte (adj p=3.3E-19) and endothelial genes (adj p=2.8E-04) in the yellow module (upregulated, enriched for immunity and organ development), and a significant enrichment of neuronal genes (adj p=2.5E-60) in the brown module (upregulated, enriched for synaptic processes). Furthermore, we detected a significant enrichment of oligodendrocyte genes (adj p=7.7E-33) in the blue module (downregulated, enriched for myelination).

We validated the results conducting module preservation analysis, using C2 as the test sample. We observed strong evidence of preservation for the blue (myelination) and brown (synapse) modules, and moderate evidence of preservation in the green module (translation). No evidence of preservation was detected for the yellow module.

Figure 8A:
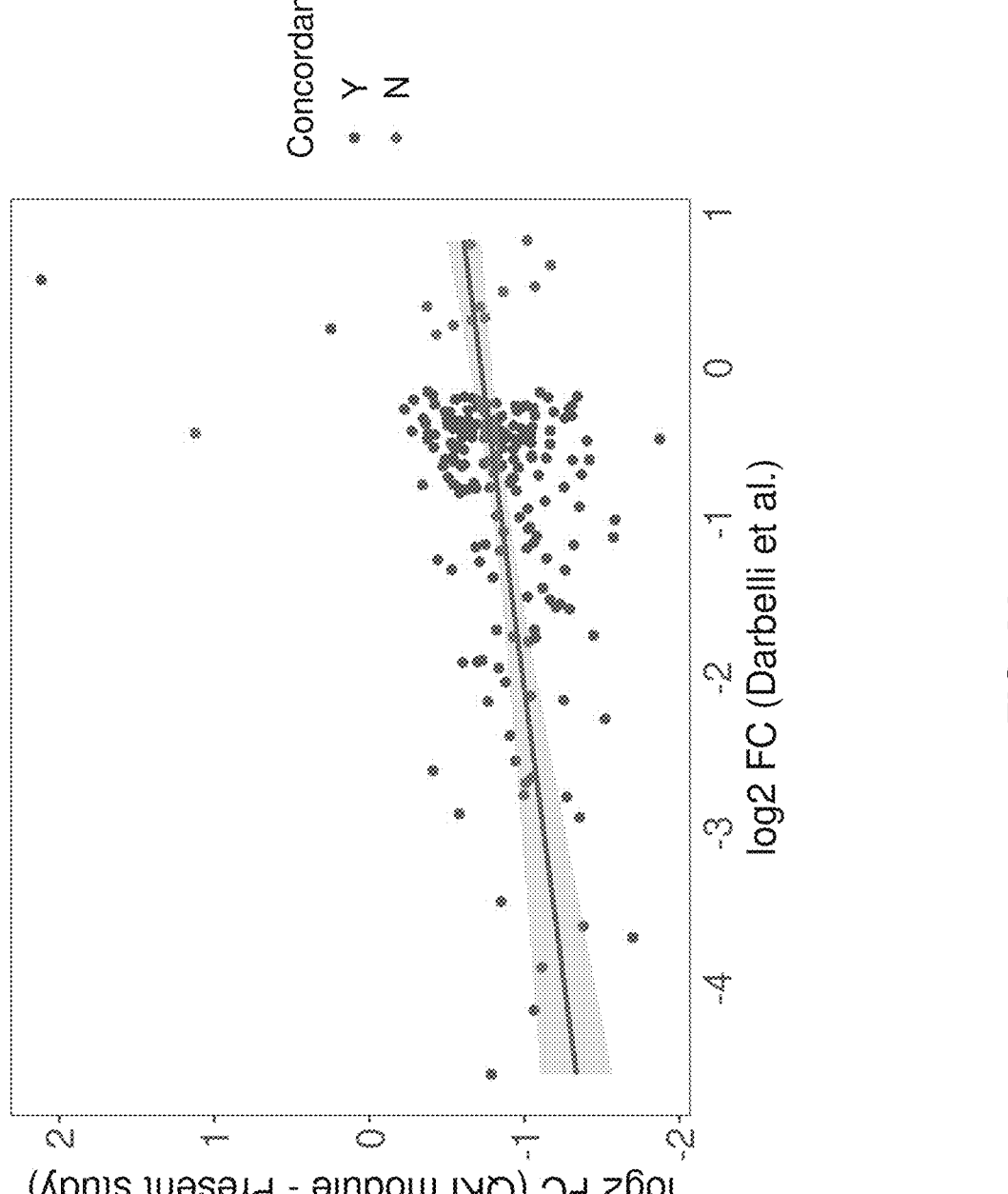
FIGS. 8A and 8B illustrate comparison between differentially expressed genes from the QKI-KO study from [19] and genes detected in the QKI module, downregulated in MSA-C, enriched for both oligodendrocyte genes and myelination processes.
Figure 8B:
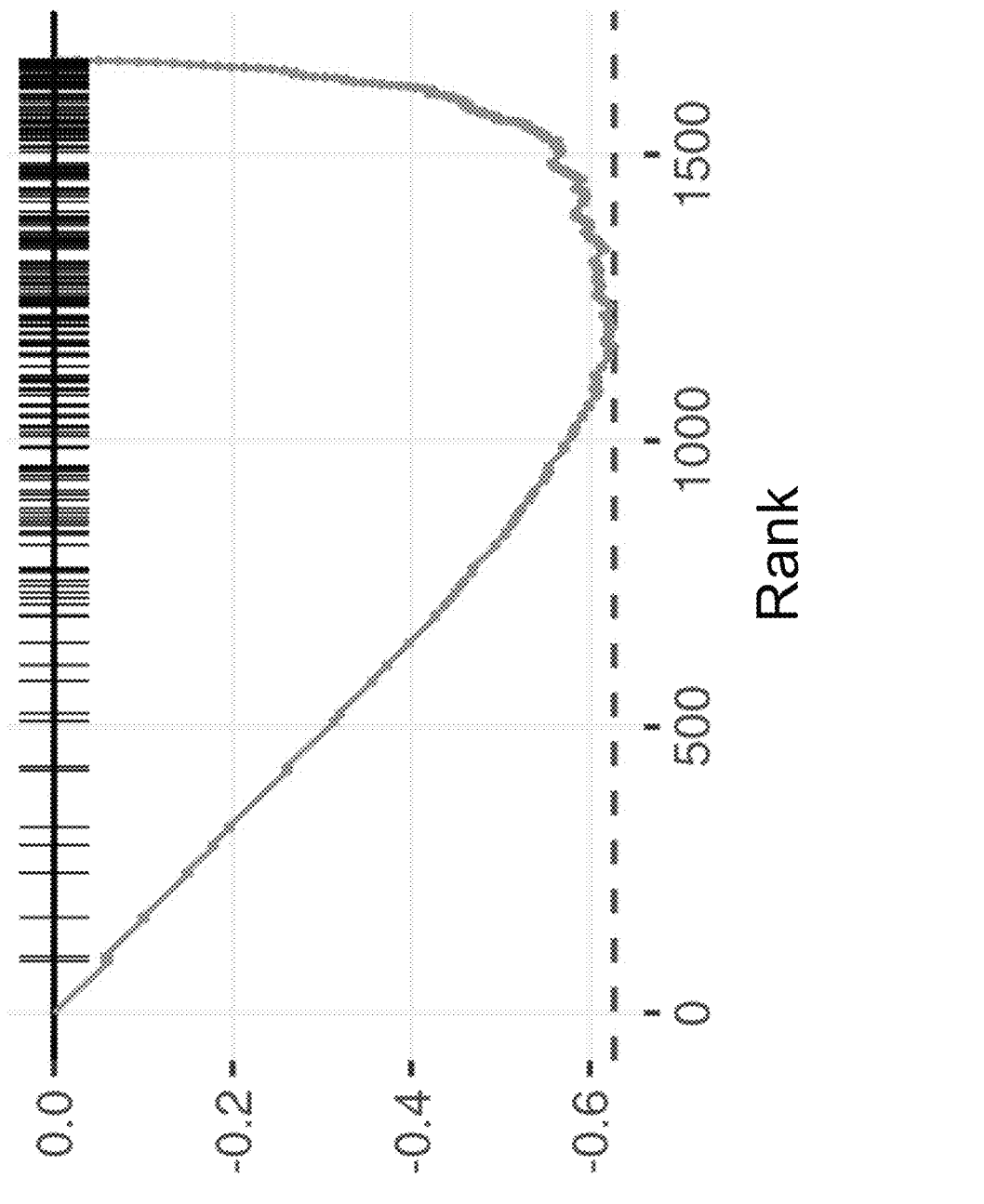

Finally, we conducted a cross-comparison between the genes in the blue module (QKJ) with the data from Darbelli et al. [19], containing a list of 1,899 differentially expressed genes after comparison of oligodendrocyte-specific QKI-deficient mice vs controls. After intersecting the two lists we detected 40.8% (n=198) of the 485 genes in the blue module shared with the QKI-deficient DEGs (FIGS. 15A-15D). Additionally, 93.9% of the shared genes showed a concordant log 2 FC (downregulation), with a significant positive correlation between the two datasets (p=0.311; p=8.0E-06) (FIG. 8A). We estimated the enrichment of QKI module genes in the QKI-deficient list by GSEA, detecting a significant enrichment across the downregulated genes Enrichment score=−0.627; p=1.07E-05) (FIG. 8B).

Discussion

Overview

We conducted a genome-wide expression profiling study using cerebellar white matter (CWM) homogenates and LCM purified oligodendrocytes from MSA patients and healthy controls (HC). Two independent cohorts were analyzed using different expression profiling approaches and the differentially expressed genes were prioritized using meta-analysis techniques. WGCNA was applied to find clusters of genes functionally related and associated with the disease. This is the largest RNA profiling study conducted on post-mortem brain samples from MSA patients to date.

Differential Dysregulation in MSA Subtypes Demonstrates More CWM Transcriptional Changes in MSA-C than in MSA-P After p-value combination, we obtained the largest number of DEGs in the MSA-C subgroup comparison (n=747). Only one gene was noted to be differentially expressed in the MSA-P sub-type analysis. Of note, the majority of the MSA-P patients had demonstrable GCIs in the CWM and 35 DEGs were identified when the MSA cohort was utilized as a single group in a case/control analysis (MSA-C plus MSA-P vs. HC). Of note, the ratio of MSA-P:MSA-C was 2.6:1 therefore the decreased number of DEGs noted in the combined MSA analysis is likely due to the higher number of MSA-P patients in our study. These results agree with the larger involvement of CWM alterations in MSA-C compared to MSA-P during the early stages of the disease [21, 58]. It is possible that due to the early involvement of CWM in MSA-C there is a longer time for the disease-related transcriptional changes to develop in the CWM in these patients. Roncevic et al. [58] found more cerebellar and pontine involvement in MSA-C compared to MSA-P. Dash et al. [21] used voxel-based morphometry (VBM) and diffusion tensor imaging (DTI) to assess the WM and GM changes in the two MSA subtypes and healthy controls. In comparison to controls, MSA-C showed widespread WM changes in supratentorial and infratentorial regions, whereas MSA-P only showed the involvement of association tracts. Their comparison between MSA-C and MSA-P confirmed a greater prevalence of cerebellar changes in MSA-C patients.

Oligodendrocyte Genes are Downregulated and Enriched for Myelination Processes

Results from multiple analyses in our study (bulk tissue and LCM RNA sequencing) converge on strong evidence of the dysregulation of oligodendrocyte genes in MSA-C. WGCNA analysis conducted using bulk tissue expression data showed the presence of a coexpression module (blue, n=485 genes) negatively associated with disease status in MSAC, enriched for myelination processes, and showing a significant enrichment of oligodendrocyte expressed genes in comparison to the other modules. Additionally, this module showed a strong preservation in the independent C2 dataset. The top hub gene in this blue coexpression network was QKI. This gene (downregulated in MSA-C) encodes for an RNA-binding protein involved in myelination and oligodendrocyte differentiation [1]. Darbelli et al. [19] conducted a transcriptomic analysis of oligodendrocyte-specific QKI conditional knock-out (KO) mouse brain and found approximately 1,800 genes differentially expressed. The underlying functional annotation of these genes was enriched for axon ensheathment and myelination. Moreover, they detected 810 alternatively spliced genes in the conditional KO animals. These results suggest a potential key role of QKI as a regulator of RNA metabolism and alternative splicing in oligodendrocytes. The comparison of the genes included in the QKI (blue) module with the list from Darbelli et al. [19] showed a significant statistical enrichment across downregulated genes, strengthening our results.

Interestingly, key myelin genes, including MBP, MAG, MOBP, and PLP1 were all included in the QKI module, and also downregulated in the QKI-KO mice. The study by Bettencourt et al., (2019) reported MSA-associated DNA methylation changes in MOBP, suggesting that the observed downregulation of this gene in MSA might be regulated by changes in DNA methylation levels. For these reasons, we propose that QKI is an important candidate gene for MSA. This gene encodes an RNA-binding protein that regulates pre-mRNA splicing, export of mRNAs from the nucleus, protein translation, and mRNA stability. QKI is also a known regulator of oligodendrocyte differentiation and myelination [20, 39, 64], but not of cell death [63]. In a recent study Zhou et al. [82] used a conditional QKI-KO mouse showing that the turnover of the structural lipid components of the mature myelin is controlled by QKI via coactivation of peroxisome proliferator-activated receptor β-retinoid X receptor α (PPARβ-RXRα) complex. Interestingly, they also found PPARβ and RXR agonists (KD3010, bexarotene) alleviate QKI deficiency-induced demyelination. These findings might open new possibilities about exploring potential MSA treatments with the goal of reducing myelin dysfunction via the QKI biological pathway.

As mentioned in the Introduction, the relocalization of p25α from the myelin sheath to the oligodendrocyte soma is one of the earliest molecular events that may trigger α-synuclein aggregation. This process may also slow oligodendrocyte precursor cell maturation by the α-synuclein mediated downregulation of myelin-gene regulatory factor and myelin basic protein [44]. Interestingly, the gene coding for p25α (TPPP), which is expressed in oligodendrocytes, was detected to be significantly downregulated in MSA-C patients in our study (adj p<0.05). Additionally, SNCA was significantly downregulated after p-value combination in MSA-C (adj p<0.05). The same result was found in another study [37], but not confirmed in other work [35, 53]. Other studies based on oligodendrocyte isolation and qPCA analysis described a basal expression and a trend of an increased expression in MSA patients [5, 22].

In the LCM study, relevant genes associated with the myelination process were NF1, PLP1 and ERMN. NF1 (Neurofibromin 1) was downregulated in MSA and it encodes for a protein specialized in the formation of myelin sheaths. Mutations in this gene cause Neurofibromatosis type 1, which is characterized by the growth of tumors along nerves in various parts of the body including the brain. PLP1 (Proteolipid Protein 1) is specifically expressed in oligodendrocytes and it was also downregulated in MSA-C patients in our sample. The protein product is a predominant component of myelin, and it also has a role in the maintenance of the myelin sheath as well as in oligodendrocyte development and axonal maintenance. Groh et al. [31] showed that mice with a loss of function PLP1 mutation exhibit neuroinflammation that leads to axonal degeneration and neuronal cell loss. Finally, ERMN (Ermin), downregulated in MSA-C, is involved in myelinogenesis and in maintenance and stability of the myelin sheath.

It is worth mentioning other genes highly differentially expressed in the LCM study even if not directly functionally associated with myelination: GGCX, and MOCS. GGCX (Gamma-Glutamyl Carboxylase) was upregulated in MSA patients, and it is essential for activating vitamin K-dependent proteins [69]. Mutations in this gene cause the "GGCX Syndrome" (OMIM: 137167). It has been observed in vitro that Vitamin K delays α-synuclein fibrillization through its interaction at specific sites at the N-terminus of α-synuclein [65]. MOCS1 (Molybdenum Cofactor Synthesis 1) was downregulated and it is involved in the biological activation of molybdenum. Mutations in MOCS1 causes molybdenum cofactor deficiency which is characterized by neurodegeneration and seizures [6].

The results of the LCM study were not from two independent cohorts, as in the case of the bulk tissue results. However, since the same samples were also characterized using bulk tissue, we detected a high log 2 FC concordance rate (80%) between the two experiments for oligodendrocyte genes in the top 50% distribution of the FDR values. Additional details of this analysis are reported in our previous study [54].

Neuron Cell-Specific Genes are Upregulated in MSA CWM and are Enriched for Biological Pathways Related to Synaptic Processes Two different analytical approaches suggested significant upregulation of neuronal cell-specific genes in MSA-C and these genes were enriched for biological roles in synaptic and neurogenesis processes. When we classified the DEGs from MSA-C according to our cell-specific gene analysis approach, we detected an upregulation of neuronal genes and an enrichment for synaptic and neuronal processes. Using WGCNA analysis we detected a module of 451 co-expressed genes (brown) significantly upregulated in MSA tissue and enriched for synaptic processes. The genes in this "brown" module demonstrated a higher prevalence of neuronal-specific genes in comparison to the other significant modules. As was the case with the blue QKI module (discussed above), the brown module showed strong model preservation in our independent C2 dataset. The hub gene in the brown module co-expression network was TIAM1 (T Cell Lymphoma Invasion and Metastasis 1). This gene (upregulated in MSA-C CWM) encodes a RACI-specific guanine nucleotide exchange factor that is involved in the control of excitatory synapse development [72]. Interestingly, the green module (significantly upregulated in MSA-C CWM) was correlated with the brown module and showed an enrichment in protein transport and translation. The hub gene in this module was SYNGAP1 (Synaptic Ras GTPase Activating Protein 1, upregulated in MSA-C) which, like TIAM1, is also involved in synaptogenesis [8, 17]. The upregulation of neuron-specific genes and the enrichment for synaptogenesis is surprising in the context of a neurodegenerative disease like MSA. Monomeric a-synuclein is normally located in the presynaptic nerve terminals and is involved in synaptogenesis [80, 81]. Perhaps, the enrichment of the synaptogenesis process in MSA-C CWM in our study might be a consequence of an abnormal accumulation of a-synuclein in the synapse of MSA patients. This elevated synaptic accumulation was previously described to precede the re-localization of a-synuclein from neurons to oligodendrocytes and may represent one of the earliest and ongoing molecular events associated with the disease [68]. Alternatively, this upregulation of synaptogenesis in the context of neurodegeneration in the MSA-C brain may represent a transcriptional attempt by the remaining neurons to compensate for the overall synaptic losses within the CWM.

The Importance of Neuroinflammation in MSA-C

The combined relocalization of p25a and the ectopic presence of a-synuclein in oligodendrocytes are thought to trigger the formation of a-synuclein and p25a inclusions [50, 66]. These inclusions and resulting oligodendrocyte dysfunction, activate microglia and astrocytes contributing to the neurodegenerative process through neuroinflammation [27]. These phenomena may explain our finding of the upregulated yellow module (314 genes). This module includes a large prevalence of astrocyte and microglia genes compared to the other significant modules and it is enriched for inflammatory and tissue/organ developmental processes. We found that astrocyte and endothelial specific genes were significantly upregulated in the DEGs from bulk tissue. The top hub gene in the yellow module was TGFB2 (Transforming Growth Factor Beta 2). This gene encodes a secreted ligand of the TGF-beta (transforming growth factor-beta) superfamily of proteins that are involved in the recruitment and activation of SMAD family transcription factors. Interestingly, the levels of TGFß-2 were previously found to be increased in the neocortex of AD and dementia with Lewy bodies and were positively correlated with neuropathological markers of disease severity [16]. This finding may suggest that TGF-beta is a key regulator of the inflammatory processes that may be more generalizable to neurodegenerative diseases regardless of the underlying causes and resulting neuropathologies. In the yellow module we found also MASP1 (log 2 FC=0.944; adj p 0.380), whose mRNA expression was found upregulated in a separate study conducted using frontal lobe post-mortem brains from MSA patients and controls [36].

Collagen Genes Are Upregulated in MSA

In the combined MSA group after p-value combination we detected 35 genes, most of them upregulated in patients. In both enrichment analyses we detected a key role of collagen genes: COL4A1, COL4A2, and ITGA11; all upregulated. COL4A1 (collagen type IV alpha 1 chain) and COL4A2 (collagen type IV alpha 1 chain) encode respectively for the alpha 1 and alpha 2 chains of type IV collagen which are important components of the basement membrane in all tissues, especially blood vessels. ITGA11 (Integrin Subunit Alpha 11) is functionally related as it is a collagen receptor. Mutations in COL4A1 and COL4A2 have been associated with sporadic brain small vessel disease [56] and porencephaly [12]. Recently Paiva et al., (2018) found COL4A2 upregulated in both A30P aSyn mice and dopaminergic neurons expressing A30P aSyn, suggesting a key role of collagen-related genes in α-synuclein induced toxicity. In the same study, they demonstrated a regulation of COL4A2 expression by miR-29a-3p, known to target COL4A4 mRNA. In a separate study the loss of miR-29a was correlated with increased levels of BACE1 and amyloid-β in sporadic Alzheimer's Disease [34]. Finally, lack of collagen VI has been related to neurodegeneration in mice models [13], and its presence has been related to a neuroprotective role against β-Amyloid toxicity [15].

Beside the collagen related pathway, the top genes detected in the differential expression analysis were: ACTN1 (Actinin Alpha 1), EMP1 (Epithelial Membrane Protein 1), and NFIL3 (Nuclear Factor, Interleukin 3 Regulated). Expression changes of ACTN1 were associated with AD in hippocampus [29], whereas NFIL3 was associated with neuroprotection in models of Amyotrophic Lateral Sclerosis [70]. EMP1 protein was also found upregulated in 5×FAD AD model [25].

MSA-C Shows a Common Transcriptional Background with Alzheimer's Disease

We detected a large functional network in MSA-C patients that included APP and other AD-related genes: PSEN1, CLU, ROCK2, EFNA1 and DYRK1. The module (M1) including these genes was enriched for amyloid-β metabolism. A significant enrichment between MSA-C and AD DEGs was found in the temporal cortex and parahippocampal gyrus (AMP-AD data), but not in the other 5 regions analyzed. Additionally, after intersecting the list of genes between MSA and AD (TCX and PHG), we found a total of 243 dysregulated genes that overlapped in temporal cortex, 166 in parahippocampal gyrus, and 126 shared between both regions and MSA-C. Our results suggest that AD and MSA may share a common transcriptional background.

AD is a neurodegenerative disorder clinically defined by gradual cognitive impairment and alterations in executive function. The symptoms are correlated to the loss of synaptic connections and overall neuronal cell death [11, 24, 71]. The neuropathological hallmarks of AD are the accumulation of amyloid-β plaques (Δβ) and neurofibrillary tau tangles (NFTs) [33]. AD and MSA don't share a common brain pathology, however, it is not unusual to observe the co-occurrence of synuclein, amyloid, and/or tau pathology and in fact several studies have focused on the potential role of α-synuclein in the pathophysiology of AD [71] and it has also been reported that α-synuclein inclusions are found in more than 50% of autopsy-confirmed AD cases [4, 32, 42]. Data from human and mouse cell cultures suggest a role of α-synuclein in the GSK3β-mediated phosphorylation of tau. Additionally, in vivo models suggest Aβ could increase GSK3β activity inducing tau phosphorylation as well as α-synuclein production, leading to a cycle that could produce more Aβ and hyperphosphorylated tau in the process [71]. The presence of dysregulated AD-related genes in the MSA brains in our study might also suggest an involvement of A3 and/or tau species in MSA. It is possible that soluble A3 species may play a role in MSA and therefore might not be manifest as insoluble plaques at autopsy. This could be due to aging effects (due to the typically younger age of onset in MSA patients compared to AD) or the location within the brain that is examined (cerebellum may demonstrate higher resistance to plaque and/or tangle formation compared to medial temporal lobe regions that typically demonstrate high plaque and tangle burden in AD patients). Nonetheless, the finding of gene expression overlap with AD-related genes in the MSA cerebellum is of interest from a mechanistic and perhaps even therapeutic level.

Treatment of MSA with PPARβ and RXR Agonists

We conducted RNA expression profiling in post-mortem brain tissues (cerebellum white matter) from two independent cohorts of neuropathologically confirmed MSA patients and unaffected controls. Network analysis of the genes with the largest variance in expression in the MSA-C sub-type patients and controls showed one co-expression network dysregulated in MSA-C. This network, including 485 genes, was functionally related to myelination and axon ensheathment, and showed a significant overrepresentation of oligodendrocyte-specific genes. QKI (which showed a downregulation of gene expression in MSA-C) was found to be the hub gene for this network, being a potential regulator and upstream effector of myelination and axon ensheathment in MSA.

Previous studies support the role of QKI in oligodendrocyte function. QKI is known as a regulator of oligodendrocyte differentiation and myelination [91, 92, 93] and knocking out QKI in mice causes the dysregulation of 1,899 genes and the alternative splicing of 810 genes [94]. Those genes were also enriched for myelination and axon ensheathment biological processes as we observed in our QKI network in MSA-C. Additionally, a total of 198 genes were shared between the co-expression network from our study, and the differentially expressed genes detected in QKI KO models [94], showing a positive correlation of the expression values. Since myelination dysfunction is a key component of MSA pathogenesis [95], our data indicate for the first time that QKI is the critical regulator of this alteration in MSA. Importantly, QKI is not implicated in other synucleinopathies (like Parkinson's disease) or in other oligodendrocyte-mediated disorders of myelination.

A recent study in a conditional QKI knock-out mouse model showed that turnover of the structural lipid components of the mature myelin sheath is controlled by QKI via coactivation of the peroxisome proliferator-activated receptor β-retinoid X receptor α (PPARβ-RXRα) complex [96]. Additionally, the same study found that PPARβ and RXR agonists, KD3010 and bexarotene, are able to alleviate QKI deficiency-induced demyelination in the mouse. This indicates that these drug classes are useful for treatment of disorders that hinge on the actions of QKI and therefore provides a link to MSA whereby we demonstrate a central role for QKI in the MSA-C patient brain tissue expression network. For these reasons, KD3010 and bexarotene, along with other PPARβ and RXR agonists, can be administered to MSA patients to interfere with MSA progression by slowing or reversing the demyelination effects induced by QKI dysregulation.

Additional details regarding the disclosure provided herein including supplemental data sets are presented in Piras, I. S., Bleul, C., Schrauwen, I. et al. Transcriptional profiling of multiple system atrophy cerebellar tissue highlights differences between the parkinsonian and cerebellar sub-types of the disease. acta neuropathol commun 8, 76 (2020).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth. All publications, patents, and patent publications cited are incorporated by reference herein in their entirety for all purposes.

REFERENCES

1. Aberg K, Saetre P, Jareborg N, Jazin E (2006) Human QKI, a potential regulator of mRNA expression of human oligodendrocyte-related genes involved in schizophrenia. Proc Natl Acad Sci. doi: 10.1073/pnas.0601213103

2. Al-Chalabi A, Dürr A, Wood N W, Parkinson M H, Camuzat A, Hulot J-S, Morrison K E, Renton A, Sussmuth S D, Landwehrmeyer B G, Ludolph A, Agid Y, Brice A, Leigh P N, Bensimon G (2009) Genetic variants of the alpha-synuclein gene SNCA are associated with multiple system atrophy. PLoS One 4:e7114. doi: 10.1371/journal.pone.0007114

3. Allen M, Carrasquillo M M, Funk C, Heavner B D, Zou F, Younkin C S, Burgess J D, Chai H S, Crook J, Eddy J A, Li H, Logsdon B, Peters M A, Dang K K, Wang X, Serie D, Wang C, Nguyen T, Lincoln S, Malphrus K, Bisceglio G, Li M, Golde T E, Mangravite L M, Asmann Y, Price N D, Petersen R C, Graff-Radford N R, Dickson D W, Younkin S G, Ertekin-Taner N (2016) Human whole genome genotype and transcriptome data for Alzheimer's and other neurodegenerative diseases. Sci Data 3. doi: 10.1038/sdata.2016.89

4. Arai Y, Yamazaki M, Mori O, Muramatsu H, Asano G, Katayama Y (2001) α-Synuclein-positive structures in cases with sporadic Alzheimer's disease: Morphology and its relationship to tau aggregation. Brain Res. doi: 10.1016/S0006-8993(00)03082-1

5. Asi Y T, Simpson J E, Heath P R, Wharton S B, Lees A J, Revesz T, Houlden H, Holton J L (2014) Alpha-synuclein mRNA expression in oligodendrocytes in MSA. Glia 62:964-970. doi: 10.1002/glia.22653

6. Atwal P S, Scaglia F (2016) Molybdenum cofactor deficiency. Mol. Genet. Metab. 117:1-4

7. Bennett D A, Schneider J A, Arvanitakis Z, Wilson R S (2012) Overview and findings from the religious orders study. Curr Alzheimer Res 9:628-645. doi: 10.2174/156720512801322573

8. Berryer M H, Chattopadhyaya B, Xing P, Riebe I, Bosoi C, Sanon N, Antoine-Bertrand J, Lévesque M, Avoli M, Hamdan F F, Carmant L, Lamarche-Vane N, Lacaille J C, Michaud J L, Di Cristo G (2016) Decrease of SYNGAP1 in GABAergic cells impairs inhibitory synapse connectivity, synaptic inhibition and cognitive function. Nat Commun. doi: 10.1038/ncomms13340

9. Bettencourt C, Foti S C, Miki Y, Botia J, Chatterjee A, Warner T T, Revesz T, Lashley T, Balazs R, Viré E, Holton J L (2019) White matter DNA methylation profiling reveals deregulation of HIP1, LMAN2, MOBP, and other loci in multiple system atrophy. Acta Neuropathol. doi: 10.1007/s00401-019-02074-0

10. Bhidayasiri R, Ling H (2008) Multiple System Atrophy. Neurologist 14:224-237. doi: 10.1097/NRL.0b013e318167b93f 11. Braak H, Braak E (1991) Demonstration of Amyloid Deposits and Neurofibrillary Changes in Whole Brain Sections. Brain Pathol. doi: 10.1111/j.1750-3639.1991.tb00661.x 12. Breedveld G, De Coo I F, Lequin M H, Arts W F M, Heutink P, Gould D B, John S W M, Oostra B, Mancini G M S (2006) Novel mutations in three families confirm a major role of COL4A1 in hereditary porencephaly. J Med Genet 43:490-495. doi: 10.1136/jmg.2005.035584

13. Cescon M, Chen P, Castagnaro S, Gregorio I, Bonaldo P (2016) Lack of collagen VI promotes neurodegeneration by impairing autophagy and inducing apoptosis during aging. Aging (Albany NY) 8:1083-1101. doi: 10.18632/aging.100924

14. Chen B J, Mills J D, Takenaka K, Bliim N, Halliday G M, Janitz M (2016) Characterization of circular RNAs landscape in multiple system atrophy brain. J Neurochem 139:485-496. doi: 10.1111/jnc.13752

15. Cheng J S, Dubal D B, Kim D H, Legleiter J, Cheng I H, Yu G-Q, Tesseur I, Wyss-Coray T, Bonaldo P, Mucke L (2009) Collagen V I protects neurons against Abeta toxicity. Nat Neurosci 12:119-21. doi: 10.1038/nn.2240

16. Chong J R, Chai Y L, Lee J H, Howlett D, Attems J, Ballard C G, Aarsland D, Francis P T, Chen C P, Lai M K P (2017) Increased transforming growth factor 32 in the neocortex of Alzheimer's disease and dementia with lewy bodies is correlated with disease severity and soluble Aβ 42 load. J Alzheimer's Dis. doi: 10.3233/JAD-160781

17. Clement J P, Ozkan E D, Aceti M, Miller C A, Rumbaugh G (2013) SYNGAP1 Links the Maturation Rate of Excitatory Synapses to the Duration of Critical-Period Synaptic Plasticity. JNeurosci. doi: 10.1523/jneurosci.0765-13.2013

18. Curry-Hyde A, Chen B J, Ueberham U, Arendt T, Janitz M (2017) Multiple System Atrophy: Many Lessons from the Transcriptome. Neurosci 107385841772391. doi: 10.1177/1073858417723915

19. Darbelli L, Choquet K, Richard S, Kleinman C L (2017) Transcriptome profiling of mouse brains with qkI-deficient oligodendrocytes reveals major alternative splicing defects including self-splicing. Sci Rep. doi: 10.1038/s41598-017-06211-1

20. Darbelli L, Vogel G, Almazan G, Richard S (2016) Quaking Regulates Neurofascin 155 expression for myelin and axoglial junction maintenance. J Neurosci. doi: 10.1523/JNEUROSCI.3529-15.2016

21. Dash S K, Stezin A, Takalkar T, George L, Kamble N L, Netravathi M, Yadav R, Kumar K J, Ingalhalikar M, Saini J, Pal P K (2018) Abnormalities of white and grey matter in early multiple system atrophy: comparison of parkinsonian and cerebellar variants. Eur. Radiol. 1-9

22. Djelloul M, Holmqvist S, Boza-Serrano A, Azevedo C, Yeung M S, Goldwurm S, Frisen J, Deierborg T, Roybon L (2015) Alpha-Synuclein Expression in the Oligodendrocyte Lineage: An in Vitro and in Vivo Study Using Rodent and Human Models. Stem Cell Reports. doi: 10.1016/j.stemcr.2015.07.002

23. Dobin A, Davis C A, Schlesinger F, Drenkow J, Zaleski C, Jha S, Batut P, Chaisson M, Gingeras T R (2013) STAR: Ultrafast universal RNA-seq aligner. Bioinformatics 29:15-21. doi: 10.1093/bioinformatics/bts635

24. Dubois B, Feldman H H, Jacova C, Cummings J L, DeKosky S T, Barberger-Gateau P, Delacourte A, Frisoni G, Fox N C, Galasko D, Gauthier S, Hampel H, Jicha G A, Meguro K, O'Brien J, Pasquier F, Robert P, Rossor M, Salloway S, Sarazin M, de Souza L C, Stem Y, Visser P J, Scheltens P (2010) Revising the definition of Alzheimer's disease: A new lexicon. Lancet Neurol.

25. Duran R C D, Wang C Y, Zheng H, Deneen B, Wu J Q (2019) Brain region-specific gene signatures revealed by distinct astrocyte subpopulations unveil links to glioma and neurodegenerative diseases. eNeuro. doi: 10.1523/ENEURO.0288-18.2019

26. Ewels P, Magnusson M, Lundin S, K??ller M (2016) MultiQC: Summarize analysis results for multiple tools and samples in a single report. Bioinformatics 32:3047-3048. doi: 10.1093/bioinformatics/btw354

27. Fanciulli A, Wenning G K (2015) Multiple-System Atrophy. N Engl J Med 372:249-263. doi: 10.1056/NEJMra1311488

28. Goedert M (2001) Alpha-synuclein and neurodegenerative diseases. Nat. Rev. Neurosci. 2:492-501

29. Gómez Ravetti M, Rosso O A, Berretta R, Moscato P (2010) Uncovering molecular biomarkers that correlate cognitive decline with the changes of hippocampus' gene expression profiles in Alzheimer's disease. PLoS One 5. doi: 10.1371/journal.pone.0010153

30. Greene C S, Krishnan A, Wong A K, Ricciotti E, Zelaya R A, Himmelstein D S, Zhang R, Hartmann B M, Zaslavsky E, Sealfon S C, Chasman D I, Fitzgerald G A, Dolinski K, Grosser T, Troyanskaya O G (2015) Understanding multicellular function and disease with human tissue-specific networks. Nat Genet. doi: 10.1038/ng.3259

31. Groh J, Friedman H C, Orel N, Ip C W, Fischer S, Spahn I, Schaffner E, Homer M, Stadler D, Buttmann M, Varallyay C, Solymosi L, Sendtner M, Peterson A C, Martini R (2016) Pathogenic inflammation in the CNS of mice carrying human PLP1 mutations. Hum Mol Genet 25:4686-4702. doi: 10.1093/hmg/ddw296

32. Hamilton R L (2006) Lewy Bodies in Alzheimer's Disease: A Neuropathological Review of 145 Cases Using α-Synuclein Immunohistochemistry. Brain Pathol. doi: 10.1111/j.1750-3639.2000.tb00269.x 33. Hardy J A, Higgins G A (1992) Alzheimer's disease: The amyloid cascade hypothesis. Science (80-.).

34. Hebert S S, Horre K, Nicolai L, Papadopoulou A S, Mandemakers W, Silahtaroglu A N, Kauppinen S, Delacourte A, De Strooper B (2008) Loss of microRNA cluster miR-29a/b-1 in sporadic Alzheimer's disease correlates with increased BACE1/-secretase expression. Proc Natl Acad Sci 105:6415-6420. doi: 10.1073/pnas.0710263105

35. Jin H, Ishikawa K, Tsunemi T, Ishiguro T, Amino T, Mizusawa H (2008) Analyses of copy number and mRNA expression level of the α-synuclein gene in multiple system atrophy. J Med Dent Sci. doi: 10.11480/jmds.550117

36. Kiely A P, Murray C E, Foti S C, Benson B C, Courtney R, Strand C, Lashley T, Holton J L (2018) Immunohistochemical and molecular investigations show alteration in the inflammatory profile of multiple system atrophy brain. J Neuropathol Exp Neurol. doi: 10.1093/jnen/nly035

37. Langerveld A J, Mihalko D, DeLong C, Walbum J, Ide C F (2007) Gene expression changes in postmortem tissue from the rostral pons of multiple system atrophy patients. Mov Disord. doi: 10.1002/mds.21259

38. Langfelder P, Horvath S (2008) WGCNA: an R package for weighted correlation network analysis. BMC Bioinformatics 9:559. doi: 10.1186/1471-2105-9-559

39. Li Z, Zhang Y, Li D, Feng Y (2000) Destabilization and mislocalization of myelin basic protein mRNAs in quaking dysmyelination lacking the QKI RNA-binding proteins. J Neurosci. doi: 10.1523/jneurosci.20-13-04944.2000

40. Liao Y, Smyth G K, Shi W (2014) FeatureCounts: An efficient general purpose program for assigning sequence reads to genomic features. Bioinformatics 30:923-930. doi: 10.1093/bioinformatics/btt656

41. Lin C H, Tan E K, Yang C C, Yi Z, Wu R M (2015) COQ2 gene variants associate with cerebellar subtype of multiple system atrophy in Chinese. Mov. Disord.

42. Lippa C F, Fujiwara H, Mann D M A, Giasson B, Baba M, Schmidt M L, Nee L E, O'Connell B, Pollen D A, St. George-Hyslop P, Ghetti B, Nochlin D, Bird T D, Cairns N J, Lee V M Y, Iwatsubo T, Trojanowski J Q (1998) Lewy bodies contain altered α-synuclein in brains of many familial Alzheimer's disease patients with mutations in presenilin and amyloid precursor protein genes. Am J Pathol. doi: 10.1016/S0002-9440(10)65722-7

43. Love M I, Huber W, Anders S (2014) Moderated estimation of fold change and dispersion for RNA-seq data with DESeq2. Genome Biol 15:550. doi: 10.1186/s13059-014-0550-8

44. May V E L, Ettle B, Poehler A M, Nuber S, Ubhi K, Rockenstein E, Winner B, Wegner M, Masliah E, Winkler J (2014) α-Synuclein impairs oligodendrocyte progenitor maturation in multiple system atrophy. Neurobiol Aging 35:2357-2368. doi: 10.1016/j. neurobiolaging.2014.02.028

45. Mills J D, Kim W S, Halliday G M, Janitz M (2015) Transcriptome analysis of grey and white matter cortical tissue in multiple system atrophy. Neurogenetics 16:107-122. doi: 10.1007/s10048-014-0430-0

46. Mills J D, Ward M, Kim W S, Halliday G M, Janitz M (2016) Strand-specific RNA-sequencing analysis of multiple system atrophy brain transcriptome. Neuroscience 322:234-250. doi: 10.1016/j. neuroscience.2016.02.042

47. Mitsui J, Matsukawa T, Ishiura H, Fukuda Y, Ichikawa Y, Date H, Ahsan B, Nakahara Y, Momose Y, Takahashi Y, Iwata A, Goto J, Yamamoto Y, Komata M, Shirahige K, Hara K, Kakita A, Yamada M, Takahashi H, Onodera O, Nishizawa M, Takashima H, Kuwano R, Watanabe H, I to M, Sobue G, Soma H, Yabe I, Sasaki H, Aoki M, Ishikawa K, Mizusawa H, Kanai K, Hattori T, Kuwabara S, Arai K, Koyano S, Kuroiwa Y, Hasegawa K, Yuasa T, Yasui K, Nakashima K, I to H, Izumi Y, Kaji R, Kato T, Kusunoki S, Osaki Y, Horiuchi M, Kondo T, Murayama S, Hattori N, Yamamoto M, Murata M, Satake W, Toda T, Dirr A, Brice A, Filla A, Klockgether T, Wallner U, Nicholson G, Gilman S, Shults C W, Tanner C M, Kukull W A, Lee V M Y, Masliah E, Low P A, Sandroni P, Trojanowski J Q, Ozelius L, Foroud T, Tsuji S (2013) Mutations in COQ2 in familial and sporadic multiple-system atrophy the multiple-system atrophy research collaboration. N Engl J Med. doi: 10.1056/NEJMoa1212115

48. Nirenberg M J, Libien J, Vonsattel J-P, Fahn S (2007) Multiple system atrophy in a patient with the spinocerebellar ataxia 3 gene mutation. Mov Disord 22:251-254. doi: 10.1002/mds.21231

49. Ordway G A, Szebeni A, Duffourc M M, Dessus-Babus S, Szebeni K (2009) Gene expression analyses of neurons, astrocytes, and oligodendrocytes isolated by laser capture microdissection from human brain: Detrimental effects of laboratory humidity. J Neurosci Res 87:2430-2438. doi: 10.1002/jnr.22078

50. Ota K, Obayashi M, Ozaki K, Ichinose S, Kakita A, Tada M, Takahashi H, Ando N, Eishi Y, Mizusawa H, Ishikawa K (2014) Relocation of p25α/tubulin polymerization promoting protein from the nucleus to the perinuclear cytoplasm in the oligodendroglia of sporadic and COQ2 mutant multiple system atrophy. Acta Neuropathol. Commun.

51. Paiva I, Jain G, Lazaro D F, Jercic K G, Hentrich T, Kerimoglu C, Pinho R, Szego E M, Burkhardt S, Capece V, Halder R, Islam R, Xylaki M, Caldi Gomes L A, Roser A-E, Lingor P, Schulze-Hentrich J M, Borovecki F, Fischer A, Outeiro T F (2018) Alpha-synuclein deregulates the expression of COL4A2 and impairs ER-Golgi function. Neurobiol Dis 119:121-135. doi: 10.1016/j. nbd.2018.08.001

52. Papp M I, Kahn J E, Lantos P L (1989) Glial cytoplasmic inclusions in the CNS of patients with multiple system atrophy (striatonigral degeneration, olivopontocerebellar atrophy and Shy-Drager syndrome). J. Neurol. Sci. 94:79-100

53. Piper D A, Sastre D, Schüle B (2018) Advancing stem cell models of alpha-synuclein gene regulation in neurodegenerative disease. Front. Neurosci.

54. Piras I S, Bleul C, Talboom J S, De Both M D, Schrauwen I, Halliday G, Myers A J, Serrano G E, Beach T G, Huentelman M J (2020) ESHRD: deconvolution of brain homogenate RNA expression data to identify cell-type-specific alterations in Alzheimer's disease. Aging (Albany NY) 12:4124-4162. doi: 10.18632/aging.102840

55. Quinn N, Wenning G (1995) Multiple system atrophy. Curr Opin Neurol 8:323-326

56. Rannikmäe K, Davies G, Thomson P A, Bevan S, Devan W J, Falcone G J, Traylor M, Anderson C D, Battey T W K, Radmanesh F, Deka R, Woo J G, Martin L J, Jimenez-Conde J, Selim M, Brown D L, Silliman S L, Kidwell C S, Montaner J, Langefeld C D, Slowik A, Hansen B M, Lindgren A G, Meschia J F, Fomage M, Bis J C, Debette S, Ikram M A, Longstreth W T, Schmidt R, Zhang C R, Yang Q, Sharma P, Kittner S J, Mitchell B D, Holliday E G, Levi C R, Attia J, Rothwell P M, Poole D L, Boncoraglio G B, Psaty B M, Malik R, Rost N, Worrall B B, Dichgans M, Van Agtmael T, Woo D, Markus H S, Seshadri S, Rosand J, Sudlow C L M (2015) Common variation in COL4A1/COL4A2 is associated with sporadic cerebral small vessel disease. Neurology 84:918-926. doi: 10.1212/WNL.0000000000001309

57. Ritchie M E, Phipson B, Wu D, Hu Y, Law C W, Shi W, Smyth G K (2015) limma powers differential expression analyses for RNA-sequencing and microarray studies. Nucleic Acids Res 43:e47. doi: 10.1093/nar/gkv007

58. Roncevic D, Palma J A, Martinez J, Goulding N, Norcliffe-Kaufmann L, Kaufmann H (2014) Cerebellar and parkinsonian phenotypes in multiple system atrophy: Similarities, differences and survival. J Neural Transm 121:507-512. doi: 10.1007/s00702-013-1133-7

59. Sailer A, Scholz S W, Nalls M A, Schulte C, Federoff M, Price T R, Lees A, Ross O A, Dickson D W, Mok K, Mencacci N E, Schottlaender L, Chelban V, Ling H, O'Sullivan S S, Wood N W, Traynor B J, Ferrucci L, Federoff H J, Mhyre T R, Morris H R, Deuschl G, Quinn N, Widner H, Albanese A, Infante J, Bhatia K P, Poewe W, Oertel W, Höglinger G U, Wüllner U, Goldwurm S, Pellecchia M T, Ferreira J, Tolosa E, Bloem B R, Rascol O, Meissner W G, Hardy J A, Revesz T, Holton J L, Gasser T, Wenning G K, Singleton A B, Houlden H (2016) A genome-wide association study in multiple system atrophy. Neurology 87:1591-1598. doi: 10.1212/WNL.0000000000003221

60. Scholz S W, Houlden H, Schulte C, Sharma M, Li A, Berg D, Melchers A, Paudel R, Gibbs J R, Simon-Sanchez J, Paisan-Ruiz C, Bras J, Ding J, Chen H, Traynor B J, Arepalli S, Zonozi R R, Revesz T, Holton J, Wood N, Lees A, Oertel W, Wüllner U, Goldwurm S, Pellecchia M T, Illig T, Riess O, Fernandez H H, Rodriguez R L, Okun M S, Poewe W, Wenning G K, Hardy J A, Singleton A B, Gasser T (2009) SNCA variants are associated with increased risk for multiple system atrophy. Ann Neurol 65:610-614. doi: 10.1002/ana.21685

61. Schroder M S, Culhane A C, Quackenbush J, Haibe-Kains B (2011) survcomp: an R/Bioconductor package for performance assessment and comparison of survival models. Bioinformatics 27:3206-3208. doi: 10.1093/bioinformatics/btr511

62. Shannon P, Markiel A, Ozier O, Baliga N S, Wang J T, Ramage D, Amin N, Schwikowski B, Ideker T (2003)

Cytoscape: A software Environment for integrated models of biomolecular interaction networks. Genome Res. doi: 10.1101/gr.1239303

63. Shingu T, Ho A L, Yuan L, Zhou X, Dai C, Zheng S, Wang Q, Zhong Y, Chang Q, Homer J W, Liebelt B D, Yao Y, Hu B, Chen Y, Fuller G N, Verhaak R G W, Heimberger A B, Hu J (2017) Qki deficiency maintains stemness of glioma stem cells in suboptimal environment by down-regulating endolysosomal degradation. Nat Genet. doi: 10.1038/ng.3711

64. SIDMAN R L, DICKIE MM, APPEL SH (1964) MUTANT MICE (QUAKING AND JIMPY) WITH DEFICIENT MYELINATION IN THE CENTRAL NERVOUS SYSTEM. Science 65. Da Silva F L, Coelho Cerqueira E, De Freitas M S, Gongalves D L, Costa L T, Follmer C (2013) Vitamins K interact with N-terminus α-synuclein and modulate the protein fibrillization in vitro. Exploring the interaction between quinones and α-synuclein. Neurochem Int 62:103-112. doi: 10.1016/j. neuint.2012.10.001

66. Song Y J C, Lundvig D M S, Huang Y, Wei P G, Blumbergs P C, Hojrup P, Otzen D, Halliday G M, Jensen P H (2007) p25α relocalizes in oligodendroglia from myelin to cytoplasmic inclusions in multiple system atrophy. Am J Pathol. doi: 10.2353/ajpath.2007.070201

67. Stefanova N, Bücke P, Duerr S, Wenning G K (2009) Multiple system atrophy: an update. Lancet Neurol. 8:1172-1178

68. Stefanova N, Wenning G K (2016) Multiple system atrophy: Emerging targets for interventional therapies. Neuropathol. Appl. Neurobiol.

69. Suleiman L, Négrier C, Boukerche H (2013) Protein S: A multifunctional anticoagulant vitamin K-dependent protein at the crossroads of coagulation, inflammation, angiogenesis, and cancer. Crit. Rev. Oncol. Hematol. 88:637-654

70. Tamai S, Imaizumi K, Kurabayashi N, Nguyen M D, Abe T, Inoue M, Fukada Y, Sanada K (2014) Neuroprotective role of the basic leucine zipper transcription factor NFIL3 in models of amyotrophic lateral sclerosis. J Biol Chem 289:1629-38. doi: 10.1074/jbc. M113.524389

71. Twohig D, Nielsen H M (2019) α-synuclein in the pathophysiology of Alzheimer's disease. Mol. Neurodegener.

72. Um K, Niu S, Duman J G, Cheng J X, Tu Y K, Schwechter B, Liu F, Hiles L, Narayanan A S, Ash R T, Mulherkar S, Alpadi K, Smimakis S M, Tolias K F (2014) Dynamic Control of Excitatory Synapse Development by a Rac1 GEF/GAP Regulatory Complex. Dev Cell. doi: 10.1016/j. devcel.2014.05.011

73. Vanacore N (2005) Epidemiological evidence on multiple system atrophy. J Neural Transm 112:1605-12. doi: 10.1007/s00702-005-0380-7

74. Wakabayashi K, Yoshimoto M, Tsuji S, Takahashi H (1998) α-synuclein immunoreactivity in glial cytoplasmic inclusions in multiple system atrophy. Neurosci Lett 249: 180-182. doi: 10.1016/50304-3940(98)00407-8

75. Wang J, Duncan D, Shi Z, Zhang B (2013) WEB-based GEne SeT AnaLysis Toolkit (WebGestalt): update 2013. Nucleic Acids Res 41. doi: 10.1093/nar/gkt439

76. Wang M, Beckmann N D, Roussos P, Wang E, Zhou X, Wang Q, Ming C, Neff R, Ma W, Fullard J F, Hauberg M E, Bendl J, Peters M A, Logsdon B, Wang P, Mahajan M, Mangravite L M, Dammer E B, Duong D M, Lah J J, Seyfried N T, Levey A I, Buxbaum J D, Ehrlich M, Gandy S, Katsel P, Haroutunian V, Schadt E, Zhang B (2018) The Mount Sinai cohort of large-scale genomic, transcriptomic and proteomic data in Alzheimer's disease. Sci data 5:180185. doi: 10.1038/sdata.2018.185

77. Zaykin D V. (2011) Optimally weighted Z-test is a powerful method for combining probabilities in meta-analysis. J Evol Biol 24:1836-1841. doi: 10.1111/j.1420-9101.2011.02297.x 78. Zhang Y, Chen K, Sloan S A, Bennett M L, Scholze A R, O'Keeffe S, Phatnani H P, Guarieri P, Caneda C, Ruderisch N, Deng S, Liddelow S A, Zhang C, Daneman R, Maniatis T, Barres B A, Wu J Q (2014) An RNA-Sequencing Transcriptome and Splicing Database of Glia, Neurons, and Vascular Cells of the Cerebral Cortex. J Neurosci 34:11929-11947. doi: 10.1523/JNEURO-SCI.1860-14.2014

79. Zhao Q Z, Yang X, Tian S J, An R, Zheng J H, Xu Y (2016) Association of the COQ2 V393A variant with risk of multiple system atrophy in East Asians: a case-control study and meta-analysis of the literature. Neurol Sci. doi: 10.1007/s10072-015-2414-8

80. Zhong H, May M J, Jimi E, Ghosh S (2002) The phosphorylation status of nuclear NF-κB determines its association with CBP/p300 or HDAC-1. Mol Cell 9:625-636. doi: 10.1016/S1097-2765(02)00477-X 81. Zhong S C, Luo X, Chen X S, Cai Q Y, Liu J, Chen X H, Yao Z X (2010) Expression and subcellular location of alpha-synuclein during mouse-embryonic development. Cell Mol Neurobiol. doi: 10.1007/s10571-009-9473-4

82. Zhou X, He C, Ren J, Dai C, Stevens S R, Wang Q, Zamler D, Shingu T, Yuan L, Chandregowda C R, Wang Y, Ravikumar V, Rao A U K, Zhou F, Zheng H, Rasband M N, Chen Y, Lan F, Heimberger A B, Segal B M, Hu J (2020) Mature myelin maintenance requires Qki to coactivate PPARβ-RXRα-mediated lipid metabolism. J Clin Invest. doi: 10.1172/jci131800.

83. A. Bennett D, A. Schneider J, Arvanitakis Z, S. Wilson R (2012) Overview and Findings from the Religious Orders Study. Curr Alzheimer Res. doi: 10.2174/156720512801322573

84. Benjamini Y, Hochberg Y (1995) Benjamini Y, Hochberg Y. Controlling the false discovery rate: a practical and powerful approach to multiple testing. J R Stat Soc B 57:289-300. doi: 10.2307/2346101

84. Durinck S, Moreau Y, Kasprzyk A, Davis S, De Moor B, Brazma A, Huber W (2005) BioMart and Bioconductor: A powerful link between biological databases and microarray data analysis. Bioinformatics 21:3439-3440. doi: 10.1093/bioinformatics/bti525

85. Langfelder P, Horvath S (2007) Eigengene networks for studying the relationships between co-expression modules. BMC Syst Biol 1:54. doi: 10.1186/1752-0509-1-54

86. Langfelder P, Luo R, Oldham M C, Horvath S (2011) Is my network module preserved and reproducible? PLoS Comput Biol 7. doi: 10.1371/journal. pcbi.1001057

87. Lee H K, Hsu A K, Sajdak J, Qin J, Pavlidis P (2004) Coexpression analysis of human genes across many microarray data sets. Genome Res 14:1085-94. doi: 10.1101/gr.1910904

88. Okonechnikov K, Conesa A, Garcia-Alcalde F (2015) Qualimap 2: Advanced multi-sample quality control for high-throughput sequencing data. Bioinformatics 32:292-294. doi: 10.1093/bioinformatics/btv566

89. R Core Team (2016) R Development Core Team. R A Lang. Environ. Stat. Comput. 55:275-286

90. Zhang B, Horvath S (2005) A general framework for weighted gene co-expression network analysis. Stat Appl Genet Mol Biol 4: Article17. doi: 10.2202/1544-6115.1128

91. Darbelli, L., Vogel, G., Almazan, G. & Richard, S. Quaking Regulates Neurofascin 155 expression for myelin and axoglial junction maintenance. *J. Neurosci.* (2016) doi:10.1523/JNEUROSCI.3529-15.2016.

92. Li, Z., Zhang, Y., Li, D. & Feng, Y. Destabilization and mislocalization of myelin basic protein mRNAs in quaking dysmyelination lacking the QKI RNA-binding proteins. *J. Neurosci.* (2000) doi:10.1523/jneurosci.20-13-04944.2000.

93. Sidman, R. L., Dickie, M. M. & Appel, S. H. Mutant Mice (Quaking and Jimpy) with Deficient Myelination in the Central Nervous System. *Science* (1964).

94. Darbelli, L., Choquet, K., Richard, S. & Kleinman, C. L. Transcriptome profiling of mouse brains with qkI-deficient oligodendrocytes reveals major alternative splicing defects including self-splicing. *Sci. Rep.* (2017) doi:10.1038/s41598-017-06211-1.

95. Wong, J. H., Halliday, G. M. & Kim, W. S. Exploring myelin dysfunction in multiple system atrophy. *Exp. Neurobiol.* 23, 337-344 (2014).

96. Zhou, X. et al. Mature myelin maintenance requires Qki to coactivate PPARβ-RXRα-mediated lipid metabolism. *J. Clin. Invest.* (2020) doi:10.1172/jci131800.

What is claimed is:

1. A method of diagnosing and treating multiple-system atrophy (MSA) in a subject, the method comprising:
determining in a subject-derived biological sample an expression level of TIAM1;
comparing the subject-derived expression level of TIAM1 with a normal control expression level of TIAM1 obtained from a non-neurodegenerative biological sample;
diagnosing the subject as having MSA by detecting a differential expression of TIAM1 in the subject-derived biological sample as compared to the normal control expression level; and
administering a peroxisome proliferator-activated receptor β (PPARβ) agonist and/or a retinoid X receptor (RXR) agonist to the subject diagnosed as having MSA.

2. The method of claim 1, wherein the expression level of TIAM1 in the subject-derived brain tissue is upregulated as compared to the normal control expression level.

3. The method of claim 2, wherein comparing the subject-derived expression level of the gene with a normal control expression level of the gene provides early detection of MSA in the subject and differentiates diagnosis of MSA from other synucleinopathies.

4. The method of claim 3, wherein the other synucleinopathies comprise Parkinson's disease (PD) and dementia with Lewy bodies (DLB).

5. The method of claim 1, wherein the RXR agonist is a retinoid, a rexinoid, a diarylamine, or an indenoisoquinoline.

6. The method of claim 5, wherein the RXR agonist is selected from the group consisting of: CD3254, SR11237, docosahexaenoic acid, magnolol, retinoic acid, 9-cis-retinoic acid (9cRA), all trans-Retinoic acid (ATRA), retinol, retinal, acyclic retinoid, 13-cis-retinoic acid, bexarotene (also known as LGD1069), fluorobexarotene, LG100268, LG100754, LG101506, LG101305, LG100364, MX-6054, BMS749, AGN194204, UAB 8, 9cUAB30, 4-methyl- UAB30, 5-methyl-UAB30, 6-methyl-UAB30, 7-methyl-UAB30, PA024, HX531, HX630, valerenic acid, dehydroabietic acid, isopimaric acid, AM6-36, and a mimetic or analogue thereof.

7. The method of claim 1, wherein the PPARβ agonist is a PPARβ/δ agonist, PPARα/(β/δ) agonist, PPAR(β/δ)/γ agonist, or pan-PPAR agonist.

8. The method of claim 7, wherein the PPARβ agonist is selected from the group consisting of 95EEAI, GW0742 (also known as GW610742), L165041, picrasidine N, MBX8025, KD3010, retinoic acid, GW501516, γ-mangostin, ertiprotafib, elafibranor (also known as GFT505), punicic acid, bavachinin, CNX-013-B2, GW4148, GW9135, isoflavone, Lyso-7, LY465608, PLX134, ZBH201102, DRL11605, GW625019, IV A337, indeglitazar (also known as PLX204 and PPM204), netoglitazone/isaglitazone (also known as PGX510 and MC555), sipoglitazar, sodelglitazar (also known as GW677954), tetradecylthio-acetic acid (TTA), chiglitazar, bezafibrate, and telmisartan.

9. The method of claim 1, wherein the MSA is cerebellar MSA (MSA-C).

10. The method of claim 1, wherein the biological sample comprises whole blood, red blood cells, plasma, serum, peripheral blood mononuclear cells (PBMCs), urine, saliva, tears, buccal swabs, cerebrospinal fluid (CSF), central nervous system (CNS) microdialysate, or nerve tissue.

11. The method of claim 1, further comprising:
determining in the subject-derived biological sample an expression level of TGFB2;
comparing the subject-derived expression level of TGFB2 with a normal control expression level of TGFB2 obtained from a non-neurodegenerative biological sample; and
further validating that the subject has MSA when the expression level of TGFB2 in the subject-derived biological sample is upregulated as compared to the normal control expression level.

12. The method of claim 1, further comprising:
determining in the subject-derived biological sample an expression level of QKI;
comparing the subject-derived expression level of QKI with a normal control expression level of QKI obtained from a non-neurodegenerative biological sample; and
further validating that the subject has MSA when the expression level of QKI in the subject-derived biological sample is downregulated as compared to the normal control expression level.

13. The method of claim 1, further comprising:
determining in the subject-derived biological sample an expression level of SYNGAP1;
comparing the subject-derived expression level of SYNGAP1 with a normal control expression level of SYNGAP1 obtained from a non-neurodegenerative biological sample; and
further validating that the subject has MSA when the expression level of SYNGAP1 in the subject-derived biological sample is upregulated as compared to the normal control expression level.

* * * * *